(12) United States Patent
Hirose et al.

(10) Patent No.: US 7,600,442 B2
(45) Date of Patent: Oct. 13, 2009

(54) ULTRASONIC PROBING METHOD AND APPARATUS THEREFOR UTILIZING RESONANCE PHENOMENON

(75) Inventors: Masayuki Hirose, Tokyo (JP); Masashi Kameyama, Osaka (JP); Nobuki Dohi, Osaka (JP); Mitsuo Okumura, Tokyo (JP); Hong Zhang, Tokyo (JP)

(73) Assignees: H&B System Co., Ltd., Tokyo (JP); The Kansai Electric Power Co., Inc., Osaka (JP); Kozo Keikaku Engineering Inc., Tokyo (JP)

( * ) Notice: Subject to any disclaimer, the term of this patent is extended or adjusted under 35 U.S.C. 154(b) by 172 days.

(21) Appl. No.: 11/719,194

(22) PCT Filed: Nov. 16, 2004

(86) PCT No.: PCT/JP2004/016982

§ 371 (c)(1),
(2), (4) Date: Nov. 15, 2007

(87) PCT Pub. No.: WO2006/054330

PCT Pub. Date: May 26, 2006

(65) Prior Publication Data

US 2009/0139333 A1 Jun. 4, 2009

(51) Int. Cl.
*G01N 29/12* (2006.01)
*G01N 29/26* (2006.01)

(52) U.S. Cl. ............... 73/865.8; 73/579; 73/598; 73/602; 73/606; 73/624

(58) Field of Classification Search ........... 73/579, 73/584, 587, 589, 592, 598, 602, 606, 618, 73/625, 630, 633, 645, 865.8
See application file for complete search history.

(56) References Cited

U.S. PATENT DOCUMENTS 4,305,294 A * 12/1981 Vasile et al. ............... 73/579

(Continued)

FOREIGN PATENT DOCUMENTS

JP 5340924 12/1993

(Continued)

OTHER PUBLICATIONS

English language Abstract of JP 8-220074.

(Continued)

*Primary Examiner*—David A. Rogers
(74) *Attorney, Agent, or Firm*—Greenblum & Bernstein, P.L.C.

(57) ABSTRACT

A flaw Z with a long probing length inside a probing target is allowed to be probed. The waves other than the probing target waves are removed or reduced, so that the individual difference in the sizing result due to the ability of the measuring personnel is eliminated to improve the precision of the probing. A transmission probe 31 and a receiving probe 32 for transmitting and receiving a wide band ultrasonic wave are included. Each time the positions of the probes 31 and 32 are moved, a received wave $G_j(t)$ is obtained. From a spectrum $F_j(f)$ corresponding to the received wave $G_j(t)$, a narrowband spectrum $FA_j(f)$ is extracted. A component wave $GA_j(t)$ corresponding to the narrow band spectrum $FA_j(f)$ is obtained by inverse Fourier transformation. The component wave $GA_j(t)$ is provided for a comparative display using a predetermined sizing coefficient. The position of a flaw Z is determined inside a probing target 30 right below the line segment connecting the centers of the transmission probe 31 and the receiving probe 32, based on at which of the measurement points a wave is generated on the comparative display screen.

20 Claims, 46 Drawing Sheets

U.S. PATENT DOCUMENTS

| | | | | |
|---|---|---|---|---|
| 4,452,082 A | * | 6/1984 | Miwa | 73/599 |
| 4,522,064 A | * | 6/1985 | McMillan | 73/592 |
| 5,351,544 A | * | 10/1994 | Endo et al. | 73/588 |
| 5,675,085 A | * | 10/1997 | Hayashi et al. | 73/628 |
| 5,786,535 A | * | 7/1998 | Takeuchi et al. | 73/624 |
| 5,894,092 A | * | 4/1999 | Lindgren et al. | 73/598 |
| 5,955,669 A | * | 9/1999 | Egami | 73/579 |
| 6,301,967 B1 | * | 10/2001 | Donskoy et al. | 73/579 |
| 6,380,516 B1 | | 4/2002 | Kodama et al. | |
| 6,386,037 B1 | * | 5/2002 | Kepler et al. | 73/579 |
| 6,423,943 B1 | | 7/2002 | Kodama et al. | |
| 6,672,162 B2 | * | 1/2004 | Hirose | 73/579 |
| 2002/0005399 A1 | | 1/2002 | Kodama et al. | |

FOREIGN PATENT DOCUMENTS

| | | |
|---|---|---|
| JP | 6118068 | 4/1994 |
| JP | 8220074 | 8/1996 |
| JP | 2001133444 | 5/2001 |
| JP | 2001221784 | 8/2001 |

OTHER PUBLICATIONS

English language Abstract of JP 6-118068.
English language Abstract of JP 5-340924.
English language Abstract of JP 2001-221784.
English language Abstract of JP 2001-133444.

* cited by examiner

FIG. 8

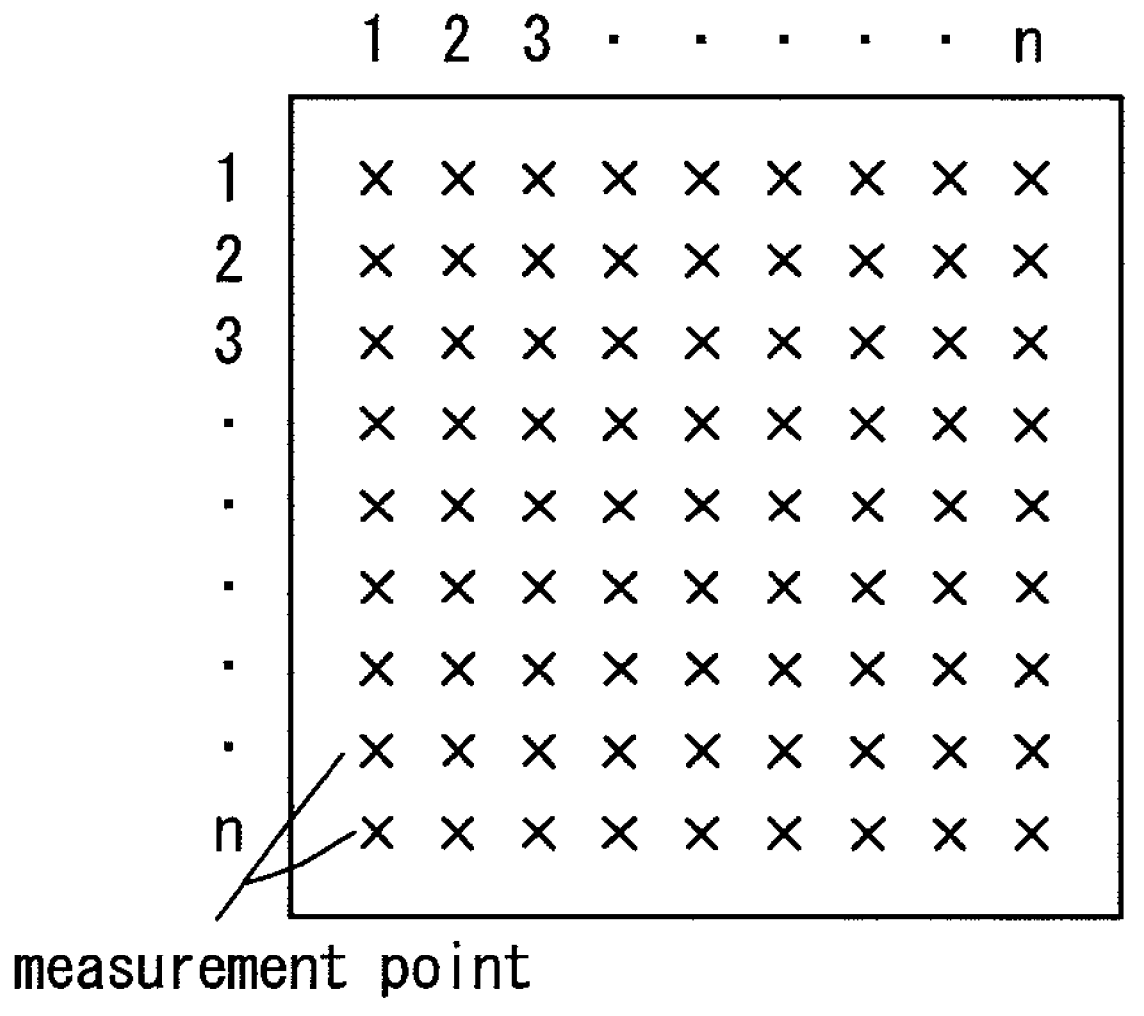

```
        1  2  3  ·  ·  ·  ·  ·  n
      ┌─────────────────────────────┐
    1 │ ×  ×  ×  ×  ×  ×  ×  ×  ×  │
    2 │ ×  ×  ×  ×  ×  ×  ×  ×  ×  │
    3 │ ×  ×  ×  ×  ×  ×  ×  ×  ×  │
    · │ ×  ×  ×  ×  ×  ×  ×  ×  ×  │
    · │ ×  ×  ×  ×  ×  ×  ×  ×  ×  │
    · │ ×  ×  ×  ×  ×  ×  ×  ×  ×  │
    · │ ×  ×  ×  ×  ×  ×  ×  ×  ×  │
    · │ ×  ×  ×  ×  ×  ×  ×  ×  ×  │
    n │ ×  ×  ×  ×  ×  ×  ×  ×  ×  │
      └─────────────────────────────┘
measurement point
```

FIG. 31
(a) 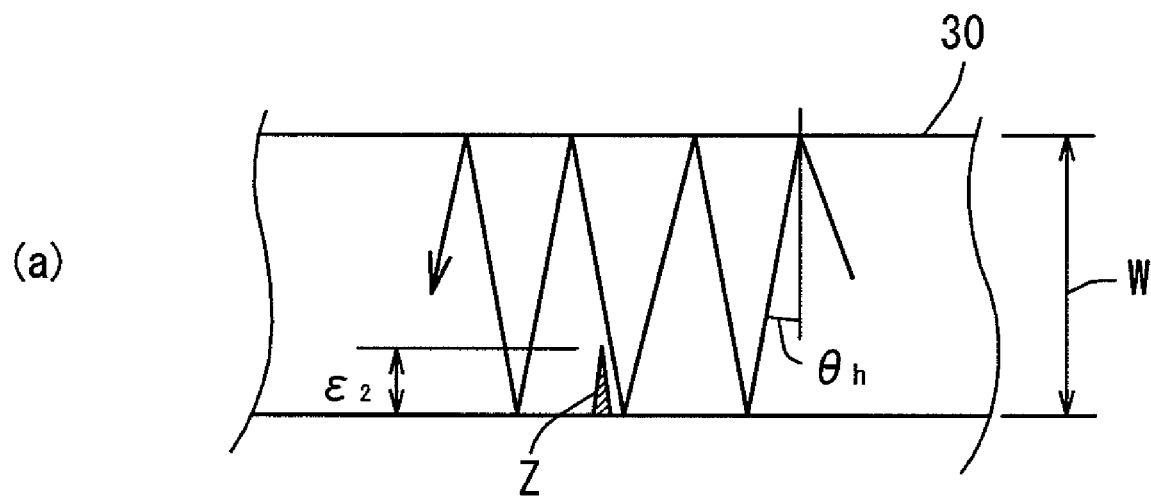
(b) 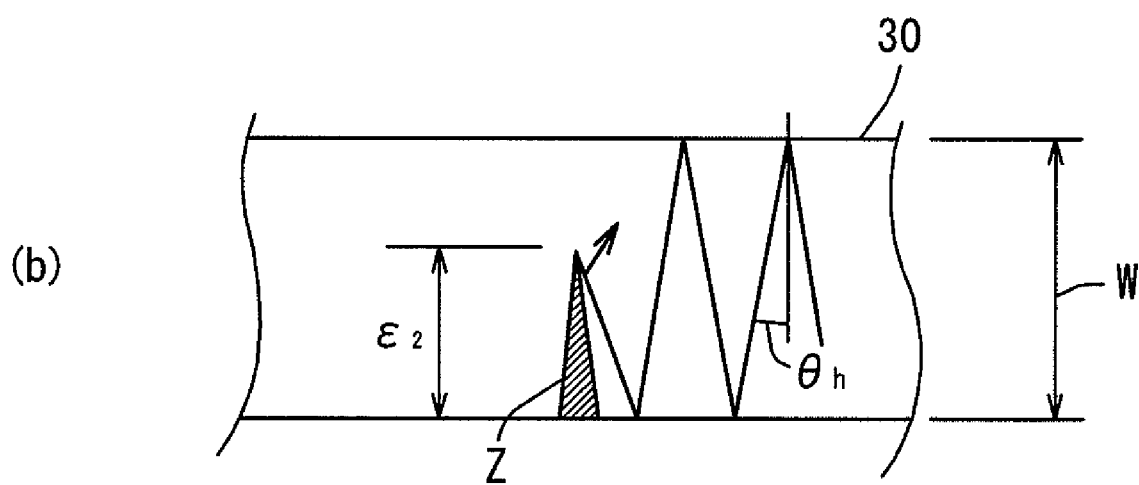

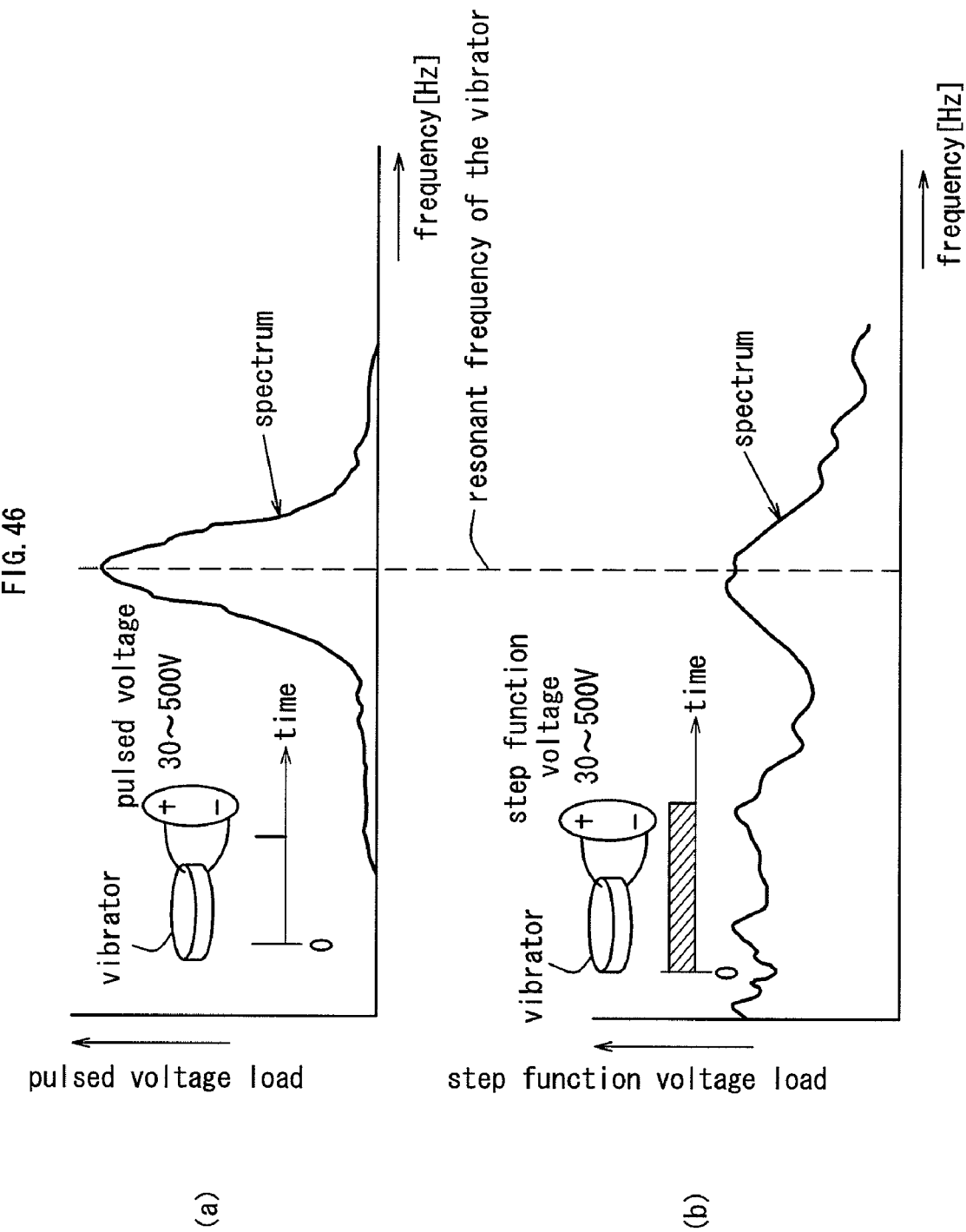

ULTRASONIC PROBING METHOD AND APPARATUS THEREFOR UTILIZING RESONANCE PHENOMENON

TECHNICAL FIELD

The present invention relates to an ultrasonic probing method and an apparatus there for utilizing a resonance phenomenon, by which presence/absence of a flaw inside a metal device formed of stainless steel, inconel (nickel-based corrosion resistant and heat-resistant alloy containing chrome and iron), cast iron or the like or in a nuclear reactor pipe, a turbine blade or the like, or a flaw in a welded section of an architecture or construction structure of steel is checked by probing, or sizing of such a flaw is performed by probing.

BACKGROUND ART

According to a conventional ultrasonic probing method (see patent document 1), a flaw in a probing target, for example, a steel material, is probed as follows. A narrowband wave having a high frequency of 1.0 MHz, 1.5 MHz or 2.0 MHz is input to a surface of the steel material in an oblique direction into a position right below the surface using an oblique probe usable both for transmission and receiving. Based on whether or not a reflected wave is received by the probe from the defect (so-called flaw) in the steel material in the vicinity of the pole, it is evaluated whether or not there is a flaw.

According to another ultrasonic probing method (see patent document 2), a transmission probe and a receiving probe are used instead of the oblique probe usable both for transmission and receiving, and it is evaluated whether or not there is a flaw by a so-called dual probe method.

However, both of the conventional methods only utilize the properties of the ultrasonic wave that the ultrasonic wave runs straight in the input direction thereof with a high directivity and that the ultrasonic wave is reflected, refracted or converted in mode at, for example, a border between different materials based on the Huygens' principle and the Snell's law. Therefore, these methods have the following problems.

1) According to the conventional methods, a high frequency vibration is used. Therefore, it is relatively difficult to probe a flaw in a probing target formed of a material having a large scattering attenuation such as cast iron or the like.

2) According to the conventional methods, probing is easily performed when a probing area is limited, for example, when a flaw in a welded section is to be probed. However, when a probing area is large, the ultrasonic wave transmission and receiving probes need to be moved for scanning in the entire probing area to each measurement point. This requires a huge number of measurement steps.

3) According to the conventional methods, when it is found whether there is a flaw or not, the determination on the sizing (detection of the width, height, size and the like of the flaw) relies on the ability of the measuring personnel. For this reason, individual differences are generated in sizing.

4) According to the conventional methods, a high frequency vibration is used. Therefore, the amount of vibration attenuated and lost inside the probing target is large. Although being effective for probing a flaw with a short probing length of about 100 mm, the methods are not usable to probe a defect (flaw) located at a long probing length.

Patent document 1: Japanese Laid-Open Patent Publication No. 2001-221784

Patent document 2: Japanese Laid-Open Patent Publication No. 2001-133444

DISCLOSURE OF THE INVENTION

Problems to be Solved by the Invention

The present invention has an object of providing an ultrasonic probing method and apparatus, by which a wide band ultrasonic wave (ultrasonic wave with a wide band; including a low frequency range) is input to a probing target by a transmission probe, and a wide band ultrasonic wave is received by a receiving probe; a narrow band spectrum of a specified frequency range is extracted from the received wide band wave, so that even a flaw causing a large scattering attenuation can be probed; the sizing coefficients are set for performing the probing with a high precision, and by setting the sizing coefficients to appropriate values, the waves other than the probing target waves are removed or reduced, so that the individual difference in the sizing result due to the ability of the measuring personnel can be eliminated to improve the precision of the probing; a flaw with a long probing length can be probed; and thus the number of probing steps can be significantly reduced from the conventional art.

Means for Solving the Problems

By an ultrasonic probing method, according to the present invention, utilizing a resonance phenomenon, a step function voltage is applied to a vibrator in a transmission probe; and a wide band ultrasonic wave is continuously transmitted from the transmission probe and a wide band ultrasonic wave from the probing target is received by a receiving probe. A measurement is performed in the state where the transmission probe and the receiving probe are located away from each other on a surface of the probing target. The method has a receiving function of obtaining a received wave $G_j(t)$ each time the position of each of the probes is changed; an arithmetic operation function of obtaining a spectrum $F_j(f)$ corresponding to the received wave $G_j(t)$ by Fourier transformation; a display function of providing a comparative display of the received wave $G_j(t)$ and the spectrum $F_j(f)$ at measurement points j; a function of generating longitudinal cursors $f_1$, $2f_1, 3f_1, \ldots, n_A f_1$ on a screen of the comparative display of the spectrum $F_j(f)$, and changing the positions of the longitudinal cursors to match each of all the cursors to a rising spectrum peak having a large value; and a function of performing an arithmetic operation/display of a thickness W of the probing target from the values of the longitudinal cursors and a sonic velocity $V_P$ of the probing target. The method comprises a first step of extracting a narrow band spectrum $FA_j(f)$ of a frequency of $n_B \cdot f_1$ from the spectrum $F_j(f)$ using an integer $n_B$ of 1 or greater ($n_B \leqq n_A$), and obtaining a component wave $GA_j(t)$ corresponding to the narrow band spectrum $FA_j(f)$ by inverse Fourier transformation; a second step of providing a comparative display of the component wave $GA_j(t)$ using predetermined sizing coefficients $n_{s1}$, $n_{s2}$ and $n_{s3}$; and a third step of determining the position of a flaw inside the probing target right below a line segment connecting the center of the transmission probe and the center of the receiving probe, based on at which of the measurement points a wave is generated on the screen of the comparative display of the component wave $GA_j(t)$.

According to the above-described structure, a wide band ultrasonic wave is input to a probing target by a transmission probe, and a wide band ultrasonic wave is received by a receiving probe. From a spectrum $F_j(f)$ corresponding to the wide band received wave $G_j(t)$, a narrow band spectrum $FA_j(f)$ of a specified frequency range of $n_B \cdot f_1$ frequency (especially, a flow frequency range) is extracted. A component wave $GA_j(t)$ corresponding to this is obtained by inverse Fourier transformation (especially, a narrow band component wave is extracted from the longitudinal resonant spectrum).

Since the wide band ultrasonic wave is transmitted and received and the received wave is analyzed as described above, a flaw causing a large scattering attenuation can be probed.

In addition, the sizing coefficients are set for performing the probing with a high precision. By setting the sizing coefficients to appropriate values, the waves other than the probing target waves are removed or reduced. Therefore, the precision of the probing can be improved.

Since the wide band ultrasonic wave which is input to the probing target contains a low frequency component which is attenuated only very little inside the probing target 30, a flaw with a long probing length can be probed.

By an ultrasonic probing method, according to the present invention, utilizing a resonance phenomenon, a step function voltage is applied to a vibrator in a transmission probe; and a wide band ultrasonic wave is continuously transmitted from the transmission probe and a wide band ultrasonic wave from the probing target is received by a receiving probe. A measurement is performed in the state where the transmission probe and the receiving probe are located away from each other on a surface of the probing target. The method has a receiving function of obtaining a received wave $G_j(t)$ each time the position of each of the probes is changed; an arithmetic operation function of obtaining a spectrum $F_j(f)$ corresponding to the received wave $G_j(t)$ by Fourier transformation; a display function of providing a comparative display of the received wave $G_j(t)$ and the spectrum $F_j(f)$ at measurement points j; a function of generating longitudinal cursors $f_1$, $2f_1, 3f_1, \ldots, n_A f_1$ on a screen of the comparative display of the spectrum $F_j(f)$, and changing the positions of the longitudinal cursors to match each of all the cursors to a rising spectrum peak having a large value; a function of performing an arithmetic operation/display of a thickness W of the probing target from the values of the longitudinal cursors and a sonic velocity $V_P$ of the probing target; and a function of obtaining a longitudinal cursor $f_{S1}$ by an arithmetic operation of $f_{S1}=\gamma_1 \cdot f_1$ using a sonic ratio $\gamma_1$ between a transverse wave and a longitudinal wave of the probing target, generating longitudinal cursors $f_{S1}, f_{S2}, f_{S3}, \ldots, n_A f_{S1}$ on the screen of the comparative display of the spectrum $F_j(f)$, and changing the positions of the longitudinal cursors by a small amount to match the cursors, which are obtained by multiplying the longitudinal cursor $f_{S1}$ by an integer, to a rising spectrum peak having a relatively small value. The method comprises a first step of extracting a narrow band spectrum $FA_j(f)$ of a frequency of $n_B \cdot f_{S1}$ from the spectrum $F_j(f)$ using an integer $n_B$ of 1 or greater ($n_B \leq n_A$), and obtaining a component wave $GA_j(t)$ corresponding to the narrow band spectrum $FA_j(f)$ by inverse Fourier transformation; a second step of providing a comparative display of the component wave $GA_j(t)$ using predetermined sizing coefficients $n_{S1}$, $n_{S2}$ and $n_{S3}$; and a third step of determining the position of a flaw inside the probing target right below a line segment connecting the center of the transmission probe and the center of the receiving probe, based on at which of the measurement points a wave can be confirmed to be generated on the screen of the comparative display of the component wave $GA_j(t)$.

According to the above-described structure, a wide band ultrasonic wave is input to a probing target by a transmission probe, and a wide band ultrasonic wave is received by a receiving probe. From a spectrum $F_j(f)$ corresponding to the wide band received wave $G_j(t)$, a narrow band spectrum $FA_j(f)$ of a specified frequency range of $n_B \cdot f_1$ frequency (especially, a flow frequency range) is extracted. A component wave $GA_j(t)$ corresponding to this is obtained by inverse Fourier transformation (especially, a narrow band component wave is extracted from the longitudinal resonant spectrum).

Since the wide band ultrasonic wave is transmitted and received and the received wave is analyzed as described above, a flaw causing a large scattering attenuation can be probed.

In addition, the sizing coefficients are set for performing the probing with a high precision. By setting the sizing coefficients to appropriate values, the waves other than the probing target waves are removed or reduced. Therefore, the precision of the probing can be improved.

Since the wide band ultrasonic wave which is input to the probing target contains a low frequency component which is attenuated only very little inside the probing target 30, a flaw with a long probing length can be probed.

In one embodiment of the present invention, the positions of the transmission probe and the receiving probe are changed by translating the positions in units of a predetermined amount in a direction perpendicular to the line segment connecting the centers of the probes, or by fixing the position of either one probe and moving the other probe by a predetermined amount in a circumferential direction with the fixed position as the center.

Thus, the number of measurement steps is reduced to shorten the time required for probing. Namely, since the measurement can be performed line by line, as opposed to the conventional point by point measurement, the number of probing steps can be significantly reduced.

In one embodiment of the present invention, a function $\sin\{(\pi/2)(f/f_{HL})\}$ defined by the spectrum $F_j(f)$ and a predetermined $f_{HL}$ is used to calculate $$\tilde{F}_j(f) = \sin\frac{\pi}{2}\left(\frac{f}{f_{HL}}\right) \times F_j(f);$$

$$\tilde{G}_j(t) = \int_{-\infty}^{\infty} (\tilde{F}_j(f) \cdot e^{i\omega t}) df$$

is calculated by Fourier transformation; $F_j(f)$ is replaced with $\tilde{F}_j(f)$; and $G_j(f)$ is replaced with $\tilde{G}_j(f)$ (where $\tilde{F}_j(f)$ and $\tilde{G}_j(f)$ represent a state where "~" is provided above $F_j$ and $G_j$ in the expression; i is an imaginary number; the same is applied to the following).

In one embodiment of the present invention, the narrow band spectrum $FA_j(f)$ is extracted by: obtaining a combination function $S(f)$ of an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater; setting the frequency $f_0$ to a value of $n_B \times f_1$ or a value of $n_B \times f_{S1}$; and obtaining $FA_j(f)$ by an arithmetic operation of: $FA_j(f) = S(f)^{n_{S4}} \times F_j(f)$, using the function $S(f)$ and a sizing coefficient $n_{S4}$.

According to the above-described structure, the narrow band spectrum $FA_j(f)$ is obtained using the combination function $S(f)$ and the sizing coefficient $n_{S4}$ ($n_{S4}$ is an integer of 1 or greater). Therefore, the narrow band spectrum can be obtained simply and appropriately. By increasing the value of $n_{S4}$, the bandwidth of the narrow band spectrum $FA_j(f)$ can be decreased.

In one embodiment of the present invention, the narrow band spectrum $FA_j(f)$ is extracted by performing an arithmetic operation of:

$$FA_j(f) = S(f) \cdot F_j(f),$$

or band pass processing,
in the state where:
a predetermined value $\Delta f_a$ which is preset or an externally input is used;
the longitudinal cursor $f_1$ or $f_{S1}$ is represented as $\tilde{f}_1$, (where $\tilde{f}_1$ represents a state where "~" is provided above $f_1$ in the expression; the same is applied to the following); and
a function S(f) which is:
0.0 at a frequency of $0 \leq f < \tilde{f}_1 - \Delta f_a$,
1.0 at a frequency of $\tilde{f}_1 - \Delta f_a \leq f \leq \tilde{f}_1 + \Delta f_a$, and
0.0 at a frequency of $f > \tilde{f}_1 + \Delta f_a$,
and the spectrum $F_j(f)$ are used.

According to the above-described structure, the narrow band spectrum $FA_j(f)$ is extracted using the combination function S(f) and the spectrum $F_j(f)$ corresponding to the received wave $G_j(t)$. Therefore, the narrowband spectrum can be obtained simply and appropriately.

In one embodiment of the present invention, the component wave $GA_j(t)$ is provided for the comparative display using the predetermined sizing coefficients $n_{S1}$, $n_{S2}$ and $n_{S3}$ by:
setting the maximum amplitude of each of the measurement points j of the component wave $GA_j(t)$ to $A_j$;
setting the maximum value in $A_j$ to $A_{max}$;
replacing $A_j$ which is $A_j = (1/n_{S1})A_{max}$ with $A_{max}$ using the sizing coefficient $n_{S1}$;
obtaining $\tilde{GA}_j(t)$ by an arithmetic operation of $\tilde{G}A_j(t) = (A_j/A_{max})GA_j(t)$;
replacing $GA_j(t)$ with $\tilde{GA}_j(t)$;
then creating a wave of $n_{S3} \times \tilde{GA}_j^{nS2}(t)$ using the other sizing coefficients $n_{S2}$ and $n_{S3}$; and
providing a comparative display of $n_{S3} \times \tilde{GA}_j^{nS2}(t)$ as the comparative display of the component wave $GA_j(t)$.

Substantially the same comparative display is provided regarding the narrowband spectrum $FA_j(f)$. ($\tilde{G}$ represents a state where "~" is provided above G in the expression; the same is applied to the following.)

Therefore, the comparative display of the component wave $GA_j(t)$ is provided appropriately, and the difference in amplitude between the waves to be provided for the comparative display is clarified.

In one embodiment of the present invention, the narrow band spectrum $FA_j(f)$ is extracted by:
obtaining the narrow band spectrum $FA_j(f)$ by the arithmetic operation of:

$$FA_j(f) = S(f)^{nS4} \cdot F_j(f)$$

each time the calculation of:

$$f_0 = f_0 + \Delta f_H$$

is performed;
repeating the first through third steps each time $FA_j(f)$ is obtained; and
stopping the arithmetic operation of $f_0 = f_0 + \Delta f_H$, the arithmetic operation of $FA_j(f) = S(f)^{nS4} \times F_j(f)$, and the first through third steps by an external instruction or automatically,
in the state where:
a combination function S(f) is obtained by an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater;
the function S(f), a sizing coefficient $n_{S4}$, and a predetermined value $\Delta f_0$ are used; and
where the longitudinal cursor $f_1$ or $f_{S1}$ is represented as $\tilde{f}_1$,
the initial value of the frequency $f_0$ is $f_0 = n_B \cdot \tilde{f}_1 - \Delta f_0$,
the final value of the frequency $f_0$ is $f_0 = n_B \cdot \tilde{f}_1 + \Delta f_0$;
the change amount of the frequency is $\Delta f_H$.

Therefore, the narrow band spectrum $FA_j(f)$ can be obtained simply and appropriately. By increasing the value of the sizing coefficient $n_{S4}$ ($n_{S4}$ is an integer of 1 or greater), the bandwidth of the narrow band spectrum $FA_j(f)$ obtained by the arithmetic operation of $FA_j(f) = S(f)^{nS4} \cdot F_j(f)$ can be decreased.

In one embodiment of the present invention, the narrow band spectrum $FA_j(f)$ is extracted by:
obtaining the narrow band spectrum $FA_j(f)$ by the arithmetic operation of:

$$FA_j(f) = S(f) \times F_j(f)$$

or band pass processing each time the calculation of:

$$f_0 = f_0 + \Delta f_H$$

is performed;
repeating the first through third steps each time $FA_j(f)$ is obtained; and
stopping the arithmetic operation of $f_0 = f_0 + \Delta f_H$, the arithmetic operation of $FA_j(f) = S(f) \cdot F_j(f)$, and the first through third steps by an external instruction or automatically,
in the state where:
the predetermined value $\Delta f_a$ is used;
a function S(f) which is
0.0 at a frequency of $0 \leq f < f_0 - \Delta f_a$,
1.0 at a frequency of $f_0 - \Delta f_a \leq f \leq f_0 + \Delta f_a$, and
0.0 at a frequency of $f > f_0 + \Delta f_a$,
is used, and the predetermined value $\Delta f_0$ is used; and
where the longitudinal cursor $f_1$ or $f_{S1}$ is represented as $\tilde{f}_1$,
the initial value of the frequency $f_0$ is $f_0 = n_B \cdot \tilde{f}_1 - \Delta f_0$,
the final value of the frequency $f_0$ is $f_0 = n_B \cdot \tilde{f}_1 + \Delta f_0$, and
the change amount of the frequency is $\Delta f_H$.

Therefore, the narrow band spectrum $FA_j(t)$ can be obtained simply and appropriately.

In one embodiment of the present invention,
either one of a combination function FiLT(t) obtained by combining a sin function which is 0.0 at time 0, 1.0 at time $t_g$, and 0.0 at time $2t_g$, and a function which is 0.0 at time $2 t_g$ or greater;
a combination function FiLT(t) obtained by combining a function which is 0.0 at time 0 to $t_g - \Delta t$, a sin function which is 0.0 at time $t_g - \Delta t$, 1.0 at time $t_g$, and 0.0 at time $t_g + \Delta t$, and a function which is 0.0 at time $t_g + \Delta t$ or greater using the predetermined value $\Delta t$; and
a combination function FiLT(t) obtained by combining an increase function which is 0.0 at time 0 and 1.0 at time $t_g$ and a function which is 1.0 at time $t_g$ or greater is selected;
a predetermined value $\Delta t_g$ and a predetermined coefficient n5 are used;
the initial value of time $t_g$ is set to 0.0;
each time the arithmetic operation of:

$$t_g = t_g + \Delta t_g$$

is performed, a component wave $GB_j(t)$ is obtained by the arithmetic operation of:

$$GB_j(t) = FiLT^{n5}(t) \cdot GA_j(t);$$

each time $GB_j(t)$ is obtained, $GA_j(t)$ in the second and third steps is replaced with $GB_j(t)$; and
the arithmetic operation of $t_g = t_g + \Delta t_g$, the arithmetic operation of $GB_j(t) = FiLT^{n5}(t) \cdot GA_j(t)$, and the second and third steps are stopped by an external instruction or automatically.

According to the above-described structure, the component wave GBj(t) is calculated using the combination function, i.e., the so-called time history filter FiLT (t). Therefore, presence/absence of a flaw can be more clearly shown by the comparative display of the component wave.

In an ultrasonic probing apparatus, according to the present invention, utilizing a resonance phenomenon, a step function voltage is applied to a vibrator in a transmission probe; and a wide band ultrasonic wave is continuously transmitted from the transmission probe and a wide band ultrasonic wave from the probing target is received by a receiving probe. A measurement is performed in the state where the transmission probe and the receiving probe are located away from each other on a surface of the probing target. The apparatus has a receiving function of obtaining a received wave $G_j(t)$ each time the position of each of the probes is changed; an arithmetic operation function of obtaining a spectrum $F_j(f)$ corresponding to the received wave $G_j(t)$ by Fourier transformation; a display function of providing a comparative display of the received wave $G_j(t)$ and the spectrum $F_j(f)$ at measurement points j; a function of generating longitudinal cursors $f_1$, $2f_1, 3f_1, \ldots, n_A f_1$ on a screen of the comparative display of the spectrum $F_j(f)$, and changing the positions of the longitudinal cursors to match each of all the cursors to a rising spectrum peak having a large value; and a function of performing an arithmetic operation/display of a thickness W of the probing target from the values of the longitudinal cursors and a sonic velocity $V_P$ of the probing target. The apparatus comprises an inverse transformation section for extracting a narrow band spectrum $FA_j(f)$ of a frequency of $n_B \cdot f_1$ from the spectrum $F_j(f)$ using an integer $n_B$ of 1 or greater, and obtaining a component wave $GA_j(t)$ corresponding to the narrow band spectrum $FA_j(f)$ by inverse Fourier transformation; a comparative display section for providing a comparative display of the component wave $GA_j(t)$ using predetermined sizing coefficients $n_{S1}$, $n_{S2}$ and $n_{S3}$; and a determination section for determining the position of a flaw inside the probing target right below a line segment connecting the center of the transmission probe and the center of the receiving probe, based on at which of the measurement points a wave is generated on the screen of the comparative display of the component wave $GA_j(t)$.

According to the above-described structure, a wide band ultrasonic wave is input to a probing target by a transmission probe, and a wide band ultrasonic wave is received by a receiving probe. From a spectrum $F_j(f)$ corresponding to the wide band received wave $G_j(t)$, a narrow band spectrum $FA_j(f)$ of a specified frequency range of $n_B \cdot f_1$ frequency (especially, a flow frequency range) is extracted. A component wave $GA_j(t)$ corresponding to this is obtained by inverse Fourier transformation (especially, a narrow band component wave is extracted from the longitudinal resonant spectrum).

Since the wide band ultrasonic wave is transmitted and received and the received wave is analyzed as described above, a flaw causing a large scattering attenuation can be probed.

In addition, the sizing coefficients are set for performing the probing with a high precision. By setting the sizing coefficients to appropriate values, the waves other than the probing target waves are removed or reduced. Therefore, the precision of the probing can be improved.

Since the wide band ultrasonic wave which is input to the probing target contains a low frequency component which is attenuated only very little inside the probing target 30, a flaw with a long probing length can be probed.

In an ultrasonic probing apparatus, according to the present invention, utilizing a resonance phenomenon, a step function voltage is applied to a vibrator in a transmission probe; and a wide band ultrasonic wave is continuously transmitted from the transmission probe and a wide band ultrasonic wave from the probing target is received by a receiving probe. A measurement is performed in the state where the transmission probe and the receiving probe are located away from each other on a surface of the probing target. The apparatus has a receiving function of obtaining a received wave $G_j(t)$ each time the position of each of the probes is changed; an arithmetic operation function of obtaining a spectrum $F_j(f)$ corresponding to the received wave $G_j(t)$ by Fourier transformation; a display function of providing a comparative display of the received wave $G_j(t)$ and the spectrum $F_j(f)$ at measurement points j; a function of generating longitudinal cursors $f_1$, $2f_1, 3f_1, \ldots, n_A f_1$ on a screen of the comparative display of the spectrum $F_j(f)$, and changing the positions of the longitudinal cursors to match each of all the cursors to a rising spectrum peak having a large value; a function of performing an arithmetic operation/display of a thickness W of the probing target from the values of the longitudinal cursors and a sonic velocity $V_P$ of the probing target; and a function of obtaining a longitudinal cursor $f_{S1}$ by an arithmetic operation of $f_{S1} = \gamma_1 \cdot f_1$ using a sonic ratio $\gamma_1$ between a transverse wave and a longitudinal wave of the probing target, generating longitudinal cursors $f_{S1}, 2f_{S1}, 3f_{S1}, \ldots, n_A f_{S1}$ on the screen of the comparative display of the spectrum $F_j(f)$, and changing the positions of the longitudinal cursors by a small amount to match the cursors, which are obtained by multiplying the longitudinal cursor $f_{S1}$ by an integer, to a rising spectrum peak having a relatively small value. The apparatus comprises an inverse transformation section for extracting a narrow band spectrum $FA_j(f)$ of a frequency of $n_B \cdot f_{S1}$ from the spectrum $F_j(f)$ using an integer $n_B$ of 1 or greater, and obtaining a component wave $GA_j(t)$ corresponding to the narrow band spectrum $FA_j(f)$ by inverse Fourier transformation; a comparative display section for providing a comparative display of the component wave $GA_j(t)$ using predetermined sizing coefficients $n_{S1}$, $n_{S2}$ and $n_{S3}$; and a determination section for determining the position of a flaw inside the probing target right below a line segment connecting the center of the transmission probe and the center of the receiving probe, based on at which of the measurement points a wave can be confirmed to be generated on the screen of the comparative display of the component wave $GA_j(t)$.

According to the above-described structure, a wide band ultrasonic wave is input to a probing target by a transmission probe, and a wide band ultrasonic wave is received by a receiving probe. From a spectrum $F_j(f)$ corresponding to the wide band received wave $G_j(t)$, a narrow band spectrum $FA_j(f)$ of a specified frequency range of $n_B \cdot f_1$ frequency (especially, a flow frequency range) is extracted. A component wave $GA_j(t)$ corresponding to this is obtained by inverse Fourier transformation (especially, a narrow band component wave is extracted from the longitudinal resonant spectrum).

Since the wide band ultrasonic wave is transmitted and received and the received wave is analyzed as described above, a flaw causing a large scattering attenuation can be probed.

In addition, the sizing coefficients are set for performing the probing with a high precision. By setting the sizing coefficients to appropriate values, the waves other than the probing target waves are removed or reduced. Therefore, the precision of the probing can be improved.

Since the wide band ultrasonic wave which is input to the probing target contains a low frequency component which is attenuated only very little inside the probing target 30, a flaw with a long probing length can be probed.

In one embodiment of the present invention, the positions of the transmission probe and the receiving probe are changed by translating the positions in units of a predetermined amount in a direction perpendicular to the line segment connecting the centers of the probes, or by fixing the position of either one probe and moving the other probe by a predetermined amount in a circumferential direction with the fixed position as the center.

Thus, the number of measurement steps is reduced to shorten the time required for probing. Namely, since the measurement can be performed line by line, as opposed to the conventional point by point measurement, the number of probing steps can be significantly reduced.

In one embodiment of the present invention, a function $\sin\{(\pi/2)(f/f_{HL})\}$ defined by the spectrum $F_j(f)$ and a predetermined $f_{HL}$ is used to calculate $$\tilde{F}_j(f) = \sin\frac{\pi}{2}\left(\frac{f}{f_{HL}}\right) \times F_j(f);$$

$$\tilde{G}_j(t) = \int_{-\infty}^{\infty} (F_j(f) \cdot e^{i\omega t}) df$$

is calculated by Fourier transformation; $F_j(f)$ is replaced with $\tilde{F}_j(f)$; and $G_j(f)$ is replaced with $\tilde{G}_j(f)$ (where $\tilde{F}_j$ and $\tilde{G}_j$ represent a state where "~" is provided above $F_j$ and $G_j$ in the expression; is an imaginary number; the same is applied to the following).

In one embodiment of the present invention, the narrow band spectrum $FA_j(f)$ is extracted by: obtaining a combination function $S(f)$ of an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater; setting the frequency $f_0$ to a value of $n_B \times f_1$ or a value of $n_B \times f_{S1}$; and obtaining $FA_j(f)$ by an arithmetic operation of:

$$FA_j(f) = S(f)^{nS4} \times F_j(f),$$

using the function $S(f)$ and a sizing coefficient $n_{S4}$.

According to the above-described structure, the narrow band spectrum $FA_j(f)$ is obtained using the combination function $S(f)$ and the sizing coefficient $n_{S4}$ ($n_{S4}$ is an integer of 1 or greater). Therefore, the narrow band spectrum can be obtained simply and appropriately. By increasing the value of $n_{S4}$, the bandwidth of the narrow band spectrum $FA_j(f)$ can be decreased.

In one embodiment of the present invention, the narrow band spectrum $FA_j(f)$ is extracted by performing an arithmetic operation of:

$$FA_j(f) = S(f) \cdot F_j(f),$$

or band pass processing,
in the state where:
a predetermined value $\Delta f_a$ which is preset or an externally input is used;
the longitudinal cursor $f_1$ or $f_{S1}$ is represented as $\tilde{f}_1$ (where $\tilde{f}_1$ represents a state where "~" is provided above $f_1$ in the expression; the same is applied to the following); and
a function $S(f)$ which is:
0.0 at a frequency of $0 \leq f < \tilde{f}_1 - \Delta f_a$,
1.0 at a frequency of $\tilde{f}_1 - \Delta f_a \leq f \leq \tilde{f}_1 + \Delta f_a$, and
0.0 at a frequency of $f > \tilde{f}_1 + \Delta f_a$,
and the spectrum $F_j(f)$ are used.

According to the above-described structure, the narrow band spectrum $FA_j(f)$ is extracted using the combination function $S(f)$ and the spectrum $F_j(f)$ corresponding to the received wave $G_j(t)$. Therefore, the narrowband spectrum can be obtained simply and appropriately.

In one embodiment of the present invention, the component wave $GA_j(t)$ is provided for the comparative display using the predetermined sizing coefficients $n_{S1}$, $n_{S2}$ and $n_{S3}$ by:
setting the maximum amplitude of each of the measurement points j of the component wave $GA_j(t)$ to $A_j$;
setting the maximum value in $A_j$ to $A_{max}$;
replacing $A_j$ which is $A_j = (1/n_{S1})A_{max}$ with $A_{max}$ using the sizing coefficient $n_{S1}$;
obtaining $\tilde{G}A_j(t)$ by an arithmetic operation of $\tilde{G}A_j(t) = (A_j/A_{max})GA_j(t)$;
replacing $\tilde{G}A_j(t)$ with $GA_j(t)$;
then creating a wave of $n_{S3} \times GA_j^{nS2}(t)$ using the other sizing coefficients $n_{S2}$ and $n_{S3}$; and
providing a comparative display of $n_{S3} \times GA_j^{nS2}(t)$ as the comparative display of the component wave $GA_j(t)$
(where $\tilde{G}$ represents a state where "~" is provided above G in the expression; the same is applied to the following).

Therefore, the comparative display of the component wave $GA_j(t)$ is provided appropriately, and the difference in amplitude between the waves to be provided for the comparative display is clarified.

In one embodiment of the present invention, the narrow band spectrum $FA_j(f)$ is extracted by:
obtaining the narrow band spectrum $FA_j(f)$ by the arithmetic operation of:

$$FA_j(f) = S(f)^{nS4} \times F_j(f)$$

each time the calculation of:

$$f_0 = f_0 + \Delta f_H$$

is performed;
repeating the processing by the inverse transformation section, the comparative display section and the determination section each time $FA_j(f)$ is obtained; and
stopping the arithmetic operation of $f_0 = f_0 + \Delta f_H$, the arithmetic operation of $FA_j(f) = S(f)^{nS4} \times F_j(f)$, and the processing by the inverse transformation section, the comparative display section and the determination section by an external instruction or automatically,
in the state where:
a combination function $S(f)$ is obtained by an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater;
the function $S(f)$, a sizing coefficient $n_{S4}$, and a predetermined value $\Delta f_0$ are used; and
where the longitudinal cursor $f_1$ or $f_{S1}$ is represented as $f_1$,
the initial value of the frequency $f_0$ is $f_0 = n_B \cdot f_1 - \Delta f_0$,
the final value of the frequency $f_0$ is $f_0 = n_B \cdot f_1 + \Delta f_0$;
the change amount of the frequency is $\Delta f_H$.

Therefore, the narrow band spectrum $FA_j(f)$ can be obtained simply and appropriately. By increasing the value of the sizing coefficient $n_{S4}$ ($n_{S4}$ is an integer of 1 or greater), the bandwidth of the narrow band spectrum $FA_j(f)$ obtained by the arithmetic operation of $FA_j(f) = S(f)^{nS4} \cdot F_j(f)$ can be decreased.

In one embodiment of the present invention, the narrow band spectrum $FA_j(f)$ is extracted by:
obtaining the narrow band spectrum $FA_j(f)$ by the arithmetic operation of:

$$FA_j(f) = S(f) \times F_j(f),$$

or band pass processing each time the calculation of:

$$f_0 = f_0 + \Delta f_H$$

is performed;

repeating the processing by the inverse transformation section, the comparative display section and the determination section each time $FA_j(f)$ is obtained; and stopping the arithmetic operation of $f_0=f_0+\Delta f_H$, the arithmetic operation of $FA_j(f)=S(f)\times F_j(f)$, and the processing by the inverse transformation section, the comparative display section and the determination section by an external instruction or automatically, in the state where:

the predetermined value $\Delta f_a$ is used;

a function $S(f)$ which is 0.0 at a frequency of $0 \leq f < f_0 - \Delta f_a$, 1.0 at a frequency of $f_0 - \Delta f_a \leq f \leq f_0 + \Delta f_a$, and 0.0 at a frequency of $f > f_0 + \Delta f_a$, is used, and the predetermined value $\Delta f_0$ is used; and where the longitudinal cursor $f_1$ or $f_{S1}$ is represented as $f_1$, the initial value of the frequency $f_0$ is $f_0 = n_B \cdot f_1 - \Delta f_0$, the final value of the frequency $f_0$ is $f_0 = n_B \cdot f_1 + \Delta f_0$, and the change amount of the frequency is $\Delta f_H$.

Therefore, the narrow band spectrum $FA_j(t)$ can be obtained simply and appropriately.

In one embodiment of the present invention, either one of a combination function FiLT (t) obtained by combining a sin function which is 0.0 at time 0, 1.0 at time $t_g$, and 0.0 at time $2t_g$, and a function which is 0.0 at time $2 t_g$ or greater;

a combination function FiLT(f) obtained by combining a function which is 0.0 at time 0 to $t_g - \Delta t$, a sin function which is 0 at time $t_g - \Delta t$, 1.0 at time $t_g$, and 0.0 at time $t_g + \Delta t$, and a function which is 0.0 at time $t_g + \Delta t$ or greater using the predetermined value $\Delta t$; and a combination function FiLT(t) obtained by combining an increase function which is 0.0 at time 0 and 1.0 at time $t_g$ and a function which is 1.0 at time $t_g$ or greater is selected;

the predetermined value $\Delta t_g$ and the predetermined coefficient n5 are used;

the initial value of time $t_g$ is set to 0.0;

each time the arithmetic operation of:

$$t_g = t_g + \Delta t_g$$

is performed, the component wave $GB_j(t)$ is obtained by the arithmetic operation of:

$$GB_j(t) = FiLT^{n5}(t) \cdot GA_j(t);$$

each time $GB_j(t)$ is obtained, $GA_j(t)$ in the processing by the comparative display section and the determination section is replaced with $GB_j(t)$; and the arithmetic operation of $t_g = t_g + \Delta t_g$, the arithmetic operation of $GB_j(t) = FiLT^{n5}(t) \cdot GA_j(t)$, and the processing by the comparative display section and the determination section are stopped by an external instruction or automatically.

According to the above-described structure, the component wave $GB_j(t)$ is calculated using the combination function, i.e., the so-called time history filter FiLT(t). Therefore, presence/absence of a flaw can be more clearly shown by the comparative display of the component wave.

According to the present invention, a flaw causing a large scattering attenuation can be probed; the precision of the probing can be improved; and a flaw with a long probing length can be probed.

BEST MODE FOR CARRYING OUT THE INVENTION

One embodiment of the present invention will be described in detail with reference to the figures.

The figures show an ultrasonic probing method and an apparatus therefor. First, with reference to FIG. 1, a structure of an ultrasonic probing apparatus usable for the method will be described.

On a surface of a probing target, a transmission probe 31 and a receiving probe 32 are provided in contact with the surface.

The transmission probe 31 transmits a wide band ultrasonic wave (e.g., 0 to 2.5 MHz), and the receiving probe 32 receives a wide band ultrasonic signal.

The transmission probe 31 is supplied with an electric current from a current supply circuit 33 of an ultrasonic transmission device, and the transmission probe 31 transmits an ultrasonic signal to be incident on the probing target 30.

An ultrasonic wave signal received by the receiving probe 32 is input to an analysis device 34 and analyzed.

In the analysis device 34, the signal received by the receiving probe 32 is amplified by an amplification circuit 35 and then filtered by a filtering circuit 36. The resultant signal is converted into a digital signal by an A/D conversion circuit (analog/digital conversion circuit) 37 and input to a CPU 40 via a gate array 38.

On a hard disc 39, analysis processing application software and time-series data processed by an operation by the CPU 40 are stored. The CPU 40 is an inverse transformation section for obtaining a component wave $GA_j(t)$ by Fourier transformation as described later.

The result of the analysis is input to, and displayed on, a display device 41. The display device 41 is a comparative display section usable for a display of a narrow band spectrum $FA_j(f)$ or for a comparative display of a component wave $GA_j(t)$ or a component wave $GB_j(t)$ as described later.

The ultrasonic probing apparatus is further structured such that necessary information is input from a keyboard 42 as input means to the CPU 40. A memory 43 is used for temporarily storing data used by the CPU 40 for operations. The CPU 40 outputs a control signal to a control circuit 44, and the control circuit 44 outputs an operation instruction signal to the amplification circuit 35, the filtering circuit 36, the A/D conversion circuit 37, the gate array 38, and the current supply circuit 33.

The current supply circuit 33 is connected to the transmission probe 31 via a coaxial cable 45. As shown in FIG. 2, the transmission probe 31 includes a step voltage generator 46 as a part of a substrate of the transmission probe 31 and a vibrator 47 built therein.

As shown in FIG. 3, the step voltage generator 46 includes a step voltage driving circuit 47 and a step voltage generation circuit 48. A step function voltage generated by the step voltage driving circuit 47 is applied to the vibrator 47.

Each time a wide band ultrasonic wave is input to the probing target 30, a received wave is obtained by the receiving probe 32. The received wave is transmitted to the amplification circuit 35 of the analysis device 34 via a coaxial cable 49 as time-wise fluctuation data of the voltage. The time-wise fluctuation data transmitted to the amplification circuit 35 reaches the A/D conversion circuit 37 via the filtering circuit 36, and an analog value of the voltage is converted into a digital value by the A/D conversion circuit 37 and transferred to the CPU 40 via the gate array 38. Thus, a time history of voltage digital value is displayed on the display device 41.

An instruction to amplify or damp the voltage and to perform low pass/high pass filtering is transferred to the CPU 40 automatically or by an external instruction using the keyboard 42. The CPU 40 controls the amplification circuit 35 and the filtering circuit 36 via the control circuit 44.

As shown in FIG. 4, the receiving probe 32 includes a gradual reducing high pass filter circuit 50, an amplification circuit 51 and a vibrator 52 built therein at a characteristic frequency in the range of 100 kHz to 300 kHz.

The current supply circuit 33 is controlled by the control circuit 44 to operate at an interval of a predetermined time period.

Thus, an ultrasonic wave is incident on the probing target 30 from the vibrator 47 (see FIG. 2) built in the transmission probe 31 at an interval of a predetermined time period.

The vibration of the vibrator 52 (see FIG. 4) built in the receiving probe 32 is excited by a sound pressure change of the probing target 30 each time the ultrasonic wave is input. The time-wise change of the voltage caused to the vibrator 52 by the excitation receives the first-order processing by the filtering circuit 50 and the amplification circuit 51 in the receiving probe 32.

When the control on the amplification circuit 35 and the filtering circuit 36 in FIG. 1 is terminated, the control circuit 44 is operated by an instruction of the CPU 40 to instruct the gate array 38 to add the received waves.

The gate array 38 adds the digital value of the time history regarding the voltage obtained by the A/D conversion circuit 37 by a designated number of times each time the time history is obtained. Under the control by the CPU 40, the gate array 44 creates an addition average time history and displays the time history in real time on the display device 41.

The filtering circuits 50 and 36 and the amplification circuits 51 and 35 are respectively built in the receiving probe 32 and the analysis device 34. The high pass filtering circuit 50 and the amplification circuit 51 built in the receiving probe 32 execute first-order processing on the received waves. The amplification circuit 35 and the filtering circuit 36 built in the analysis device 34 fine-tune the first-order-processed received waves under the control of the CPU 40. Since this fine tuning is required for improving the function of the apparatus, the amplification circuit 35 and the filtering circuit 36 may be omitted.

Next, with reference to FIG. 46, the difference between an ultrasonic wave by a pulsed voltage load and an ultrasonic wave by a step function voltage load will be described.

FIG. 46(a) shows a spectrum in the case where a pulsed voltage (30 to 500 V) is applied to a vibrator. In this case, as shown in the figure, a transmission ultrasonic wave having a relatively narrow band with the central frequency at the thickness direction resonant frequency of the vibrator is obtained (corresponding to the narrow band frequency of the conventional art).

FIG. 46(b) shows a spectrum in the case where a step function voltage (30 to 500 V) is applied to the vibrator 47 in the transmission probe 31. In this case, as shown in the figure, a spectrum in which the resonant frequency and also components lower than the resonant frequency are excited. The wide range ultrasonic wave in this embodiment is the ultrasonic wave shown in FIG. 46(b).

Next, the sizing coefficients ($n_{S1}$, $n_{S2}$, $n_{S3}$, $n_{S4}$) used in the following description will be described.

Here, $n_{S1}$ is a real number of 1.0 or greater, and $n_{S2}$, $n_{S3}$, $n_{S4}$ are each a real number of 1 or greater.

Regarding sizing coefficient $n_{S1}$:

The sizing coefficient $n_{S1}$ is for performing the sizing of a probing target flaw Z (see FIG. 6) at a high precision. A target wave for analysis (component wave) is represented as $GA_j(t)$ (j is a measurement order number) and is provided for a comparative display. The maximum amplitude of the component wave $GA_j(t)$ at each measurement is $A_j$ and the maximum value of $A_j$ is $A_{max}$. Thus, the sizing coefficient $n_{S1}$ is defined. Using the sizing coefficient $n_{S1}$ to replace $A_j$ which is $A_j \geq (1/n_{S1})A_{max}$ with the value of $A_{max}$, and a $\tilde{G}A_j(t)$ wave calculated by the following expression 1 is created.

$$\tilde{G}A_j(t) = (A_j/A_{max})GA_j(t) \quad \text{[Expression 1]}$$

Then, the $GA_j(t)$ wave is changed to a $\tilde{G}A_j(t)$ wave. $GA_j(t) \cdot \tilde{G}A_j(t)$ The sizing coefficient $n_{S1}$ is a coefficient for the above-described processing.

Regarding sizing coefficient $n_{S2}$:

In the comparative display of the component wave $GA_j(t)$, the coefficient $n_{S2}$ is defined and $GA_j^{nS2}(t)$ is displayed. This clarifies the wave amplitude difference. The sizing coefficient $n_{S2}$ is a coefficient for clarifying the wave amplitude difference.

Regarding sizing coefficient $n_{S3}$:

In the comparison of $GA_j^{nS2}(t)$, the coefficient $n_{S3}$ is defined and $n_{S3}GA_j^{nS2}(t)$ is provided for a comparative display. The sizing coefficient $n_{S3}$ is a coefficient for this comparison.

Regarding sizing coefficient $n_{S4}$:

By Fourier transformation of the received origin wave (so-called received wave) $G_j(t)$, a spectrum $F_j(f)$ shown in FIG. 5(a) is obtained. According to one method for sampling out a spectrum at the horizontal axis $f_0$ position ($f_0$ is the central frequency for extracting the spectrum), the arbitrary function $S(f)$ shown in FIG. 5(a) (the horizontal axis position at the maximum value 1.0 is aligned to $f_0$, such that $S(f)$ is 0.0 at f=0 and $S(f)$ is 0.0 at a frequency of $2f_0$ or greater) is multiplied by the function $F_j(f)$. As a result, a narrow band spectrum $S(f)^{nS4} \cdot f_j(f)$ as shown in the following expression 2 and in FIG. 5(b) is obtained.

$$FA_j(f) = S(f)^{nS4} \cdot F_j(f) \quad \text{[Expression 2]}$$

At this point, the sizing coefficient $n_{S4}$ is an integer of 1 or greater. When the value of $n_{S4}$ is greater, the band width of the spectrum $FA_j(f)$ (narrow band spectrum) obtained by the arithmetic operation of expression 2 can be smaller.

EXAMPLE 1

With reference to FIG. 6 through FIG. 17, Example 1 in which a longitudinal 12th-order resonant spectrum of $n_B \cdot f_1$ frequency=1420 kHz is sampled out and the component wave is compared at measurement points will be described.

FIG. 6 shows a measurement model of the probing target 30. The measurement model has a planar size of length X=120 mm and width Y=120 mm, and a thickness W=25 mm, and is formed of stainless steel. A line-like flaw Z is made as shown in the figure.

The transmission probe 31 and the receiving probe 32 respectively including the vibrators 47 and 52 (see FIG. 2 and FIG. 4) each having a diameter of 15 mmφ are located, such that the distance "a" between the centers of the probes 31 and 32 is fixed at 90 mm and a line segment connecting the probes 31 and 32 is perpendicular to the flaw Z. The line segment is translated by an interval of a moving amount ΔX=9 mm. Thus, a multi-point measurement, by which a plurality of received waves $G_j(t)$ are measured and compared, is performed (multi-point measurement step). In this example, ten received waves $G_j(t)$ at measurement points 1 through 10 in FIG. 6 are measured and compared.

FIG. 7 is a schematic view of FIG. 6. FIG. 8 shows a comparative example (conventional method). By the conventional method, the number of the measurement points is n×n (when n=100, the number of the measurement points is 10,000). By contrast, in Example 1, the line segment connecting the center of the transmission probe 31 and the center of the receiving probe 32 is translated by a predetermined amount (ΔX) in a direction perpendicular to the line segment, and thus the probing of the flaw Z in the probing target 30 right below the line segment is performed in one operation. Therefore, when n=100, the number of the measurement points is 100. In this manner, the number of probing steps can be significantly reduced.

Referring to FIG. 6, a wide band ultrasonic wave of 0 to 2.5 MHz is input from the transmission probe 31 to right below the surface of the probing target 30 to obtain the received wave $G_j(t)$. The received wave $G_j(t)$ obtained by the receiving probe 32 contains a great amount of multi-reflected waves with respect to the thickness W of the measurement model formed of stainless steel. The multi-reflected waves cause a resonance phenomenon to become a stronger wave than the other waves propagated in the stainless steel probing target.

The received wave $G_j(t)$ obtained by the measurement of FIG. 6 is processed with Fourier transformation by the following expression 3, and a spectrum $F_j(f)$ is obtained. FIG. 9 shows a comparative display of the spectrum $F_j(f)$. FIG. 10 is a schematic view of FIG. 9.

$$F_j(f) = \int_{-\infty}^{\infty} (G_j(t) \cdot e^{-i\omega t}) dt \quad \text{[Expression 3]}$$

Longitudinal cursors $f_1, 2f_1, 3f_1, \ldots$ are generated on the screen of the comparative display of the spectrum $F_j(f)$ in FIG. 9 and FIG. 10. The position of the longitudinal cursor $f_1$ is changed, such that all the cursors $f_1, 2f_1, 3f_1, \ldots$ each match a rising spectrum peak having a large value (cursor matching step).

Namely, the leftmost cursor position of FIG. 9 and FIG. 10 is set as $f_1$, and cursors are displayed at positions obtained by multiplying $f_1$ by an integer, i.e., positions $2f_1, 3f_1, \ldots, n_A f_1$.

At $f_1$=118.4 kHz (first-order resonant frequency with respect to the thickness of the stainless steel probing target), all the cursors at and after $3f_1$ match the generated spectrum peaks.

$f_1$ of 118.4 kHz is the first-order resonant frequency with respect to the thickness of the probing target 30 formed of stainless steel. When the longitudinal sonic velocity of stainless steel is $V_P$=5.9 mm/μsec, the relation ship represented by the following expression 4 is obtained.

$$f_1 = 10^6/(2W \div V_P) \quad \text{[Expression 4]}$$

When the sonic velocity is $V_P$, the thickness W of the probing target 30 is obtained by $W = 0.5 V_P \cdot 10^6 \div f_1$.

Since the thickness of the stainless steel probing target is W=25 mm, $$f_1 = 10^6/(2 \times 25 \div 5.9) = 118 \times 10^3 \approx 118.4 \text{ kHz}.$$

The following functions are defined:
Increase Function I(f)
f=0 I(0)=0
f=2.5 MHz I(f)=1.0
Decrease Function D(f)
f=0 D(0)=1.0
f=2.5 MHz D(f)=0

The narrow band spectrum $FA_j(f)$ is obtained by the following expression 5 by multiplying the spectrum $F_j(f)$ by the increase function I(f) and the decrease function D(f).

$$FA_j(f) = I^{n4_1}(f) \cdot D^{n4_2}(f) \cdot F_j(f) \quad \text{[Expression 5]}$$

where $n4_1$ and $n4_2$ are each an integer of 1 or greater.

The narrow band spectrum $FA_j(f)$ obtained by expression 5 is shown in FIG. 11. FIG. 12 corresponds to FIG. 11.

In FIG. 12, a spectrum $F_j(f)$, obtained by performing frequency processing on the spectrum $FA_j(f)$ in FIG. 11, specifically by decreasing the low frequency spectrum values and increasing the high frequency spectrum values, is provided for a comparative display.

Specifically, the spectrum $F_j(f)$ is obtained by replacing $FA_j$ in expression 5 with $F_j(f)$, with a predetermined value $n4_2$ being set to 0 and the integer $n4_1$ being set to 1 or greater.

The increase function I(f) and the decrease function D(f) used for obtaining FIG. 11 are specifically represented by the following expressions 6 and 7.

$$I(f) = \sin\frac{\pi}{2}\left(\frac{f}{f_{HL}}\right) \quad \text{[Expression 6]}$$

$$D(f) = \cos\frac{\pi}{2}\left(\frac{f}{f_{HL}}\right) \quad \text{[Expression 7]}$$

A predetermined value $f_{HL}$ is set to 2.5 MHz, and the integer $n4_1$=4, the integer $n4_2$=2. By substituting these values into expression 5, the arithmetic operation of the following expression 8 is performed.

$$FA_j(f) = \sin^{n4_1}\frac{\pi}{2}\left(\frac{f}{2.5 \times 10^6}\right) \cdot \cos^{n4_2}\frac{\pi}{2}\left(\frac{f}{2.5 \times 10^6}\right) \cdot F_j(f) \quad \text{[Expression 8]}$$

In FIG. 11, the narrow band spectrum $FA_j(f)$ and the component wave $GA_j(t)$ corresponding thereto (in which the horizontal axis represents the time, and the vertical axis represents the amplitude) are shown side by side.

The component wave $GA_j(t)$ (time history) and the narrow band spectrum $FA_j(f)$ have the relationship represented by the following expression 9.

$$GA_j(t) = \int_{-\infty}^{\infty} (FA_j(f) \cdot e^{i\omega t}) df \quad \text{[Expression 9]}$$

According to the comparison of the component wave $GA_j(t)$ in FIG. 11, the component wave has a smaller amplitude at measurement points 4, 5, 6, 7 and 8 with the flaw Z (see FIG. 6) than at measurement points 1, 2, 3, 9 and 10 with no flaw Z. This phenomenon occurs because the line segment connecting the transmission probe 31 and the receiving probe 32 is perpendicular to the flaw Z at measurement points 4 through 8. The component wave $GA_j(t)$ in FIG. 11 can be understood as containing a great number of resonant waves overlapping each other.

The process of sampling out only the spectrum corresponding to the position of $n_B \cdot f_1$ frequency ($n_B$ is an integer of 1 or greater) from the spectrum $F_j(f)$ in FIG. 12 is shown as a change from FIG. 13(*a*) to FIG. 13(*b*).

FIG. 14 shows the comparison at measurement points 1 through 10. FIG. 14 is obtained as follows. The integer is set as $n_B$=12, and only the spectrum of $n_B f_1$=12×118.4=1420 kHz is sampled out by band pass filtering (bandwidth: 1400 kHz to 1440 kHz). The component wave $GA_j(t)$ is calculated (first step) by expression 9 using the sampled out spectrum as the narrow band spectrum $FA_j(f)$, and then provided for a comparative display (second step).

Now, the comparative display of the component wave $GA_j(t)$ shown in FIG. 11 at measurement points 1 through 10, and the comparative display of the component wave $GA_j(t)$ shown in FIG. 14 at measurement points 1 through 10, will be compared. The latter presents the difference between the generation of the component wave $GA_j(t)$ at measurement points 4 through 8 with the flaw Z (see FIG. 6) and the generation of the component wave $GA_j(t)$ at measurement points 1, 2, 3, 9 and 10 with no flaw Z (see FIG. 6) more clearly (third step).

FIG. 15 is obtained as follows. Using the time history filter FiLT(t) shown in FIG. 16 at the cursor position $t_g$ (see FIG. 16), the component wave $GB_j(t)$ is calculated from the component wave $GA_j(t)$ in FIG. 14 by the following expression 10 (first step). The component wave $GB_j(t)$ at measurement points 1 through 10 is provided for a comparative display (second step)

$$GB_j(t)=FiLT^{n5}(t)\cdot GA_j(t) \qquad \text{[Expression 10]}$$

where $t_g=84$ μsec, $\Delta t=400$ μsec, and n5=3. As is clear from FIG. 15, the generation of the component wave $GB_j(t)$ can be confirmed at measurement points 1, 2, 3, 9 and 10 with no flaw Z (see FIG. 6) (third step).

The sizing coefficients in the comparative display in FIG. 14 and FIG. 15 are $n_{S1}=1.7$, $n_{S2}=4.0$, and $n_{S3}=1.0$, and the band width is $\Delta f_B=40$ kHz (the passband of 1440 kHz-1400 kHz).

In summary, the determination is performed as follows. FIG. 17 schematically shows the component wave $GA_j(t)$ at measurement points 1 through 10 in FIG. 14. As understood from FIG. 17, at measurement points 4 through 8, the generation of the resonant wave cannot be confirmed at any time by the comparative display of the component wave $GA_j(t)$ (second step). It is determined (third step) that there is a flaw Z in the probing target 30 right below the line segment connecting the probes 31 and 32 at measurement points 4 through 8. FIG. 17 only shows the component wave $GA_j(t)$ corresponding to FIG. 14, but substantially the same determination can be made regarding the component wave $GB_j(t)$ corresponding to FIG. 15.

In this manner, a wide band ultrasonic wave is input to the probing target 30 by the transmission probe 31, and a wide band ultrasonic wave is received by the receiving probe 32. A spectrum $F_j(f)$ corresponding to the wide band received wave $G_j(t)$ is obtained by Fourier transformation. From the spectrum $F_j(f)$, a narrow band spectrum $FA_j(f)$ of a specified frequency range of $n_B \cdot f_1$ frequency ($n_B=12$, $n_B \cdot f_1=1420$ kHz) is extracted. A component wave $GA_j(t)$ corresponding to this is obtained by inverse Fourier transformation and provided for a comparative display and determination. Therefore, a flaw Z inside the probing target with a large scattering attenuation can be probed. In addition, the sizing coefficients $n_{S1}$, $n_{S2}$ and $n_{S3}$ are set for performing the probing with a high precision. By setting the sizing coefficients to appropriate values, the waves other than the probing target waves are removed or reduced. Therefore, the individual difference in the sizing result due to the ability of the measuring personnel can be eliminated to improve the precision of the probing.

EXAMPLE 2

With reference to FIG. 18 through FIG. 26, Example 2 in which a transverse 8th-order resonant spectrum of $n_B \cdot f_1$ frequency=664 kHz is sampled out and the component wave is compared at measurement points will be described.

FIG. 18 shows a measurement model of the probing target 30. The measurement model has a planar size of length X=300 mm and width Y=400 mm, and a thickness W=20 mm, and is formed of stainless steel. A line-like flaw Z is made as shown in the figure. The width of the flaw Z is $\epsilon_1=18$ mm.

The transmission probe 31 including the vibrator 47 (see FIG. 2) having a diameter of 15 mmφ is located at a fixed position. A receiving probe 32 is located on a circumference having a constant radius R=160 mm and having the central point of the transmission probe 31 as the center. (The radius of the circumference corresponds to the distance "a" between the centers of the transmission probe 31 and the receiving probe 32.) The receiving probe 32 is moved in the circumferential direction by predetermined amounts ΔS1 and ΔS2. Thus, a multi-point measurement, by which a plurality of received waves are measured and compared, is performed (multi-point measurement step). The fixed probe and the moving probe may be the opposite.

In this case, a total of six received waves at measurement points 1 through 6 are obtained, and the received waves and the analysis waves are provided for a comparative display. A line segment connecting the probes 31 and 32 at measurement point 4 crosses the flaw Z. Hence, the interval between the measurement points on the circumference, i.e., the predetermined amounts ΔS1 and ΔS2 are set as ΔS1=16 mm and ΔS2=24 mm.

The spectrum $F_j(f)$ of the received wave $G_j(t)$ obtained in substantially the same manner as in Example 1 is provided for a comparative display (see FIG. 19). For the spectrum $F_j(f)$, a plurality of cursors are displayed. The leftmost cursor position (the solid line in FIG. 19) is set as $f_1$, and a function of generating cursors are at positions obtained by multiplying $f_1$ by an integer, i.e., positions $2f_1, 3f_1, \ldots, n_A f_1$ is used. When the cursor position $f_1$ which is automatically or manually changed becomes 150.7 kHz, all the cursors each match a rising spectrum peak having a large value (cursor matching step).

Namely, the received wave $G_j(t)$ is processed with Fourier transformation to obtain the spectrum $F_j(f)$, and the spectrum $F_j(f)$ is provided for a comparative display (spectrum comparative display step; see FIG. 19).

As the values of the spectrum $F_j(f)$, the low frequency components dominate and the high frequency components disappear on appearance.

Referring to FIG. 19, the cursors $f_1, 2f_1, 3f_1, \ldots$ are generated, and the value of $f_1$ is changed automatically or manually, such that all the cursors each match a rising spectrum peak having a large value.

The cursor $f_1$ of 150.7 kHz is applied to the following expression 11 to calculate the thickness W of the probing target 30.

$$W=0.5 V_P \times 10^6 \div f_1 \qquad \text{[Expression 11]}$$

The longitudinal sonic velocity is $V_P=5.9$ mm/μsec and $f_1=150.7$ kHz. These numerals are substituted into expression 11.

$$W=0.5 \times 5.9 \times 10^6 \div (150.7 \times 10^3)=19.5 \approx 20 \text{ mm (actual value)}$$

The increase function I(f) of expressions 5 and 6 and the decrease function D(f) of expression 7 described above are used. The integer $n4_1=2$, the predetermined value $n4_2=1$, and predetermined value $f_{HL}=2.5$ MHz are substituted into expression 5 to perform the arithmetic operation of by the following expression 12 to obtain the narrow band spectrum FAj(t).

$$FA_j(f) = \sin^{n4_1}\frac{\pi}{2}\left(\frac{f}{2.5\times 10^6}\right)\cdot \cos^{n4_2}\frac{\pi}{2}\left(\frac{f}{2.5\times 10^6}\right)\cdot F_j(f) \quad \text{[Expression 12]}$$

FIG. 20 provides a comparative display of the narrow band spectrum $FA_j(f)$ calculated by expression 12. In the right part of FIG. 20, the component wave (time history) $GA_j(t)$ calculated by expression 9 described above is also provided.

In FIG. 20, it can be confirmed that all the cursors $f_1$, $2f_1$, $3f_1$, . . . each match a spectrum peak having a large value (represented with in FIG. 20). At in FIG. 20, the generation of a spectrum peak is confirmed.

The spectrum peak represented with is generated by the following physical phenomenon.

FIG. 21 schematically shows the probing target 30 formed of stainless steel. When the probing target has a flaw Z inside thereof, a longitudinal ultrasonic wave with respect to the thickness W is multi-reflected. When the multi-reflected wave 53 reaches the flaw Z, a transverse wave 54 is generated at that position.

The spectrum $FA_j(f)$ at the cursor positions $f_1$, $2f_1$ . . . , $nf_1$ (see FIG. 20) is a resonant spectrum of the longitudinal multi-reflected wave 53. When this longitudinal resonant wave reaches the flaw Z, the transverse wave 54 is generated at this position.

The transverse wave 54 also has a resonant component. It is confirmed by many measurements that the first-order resonant frequency $f_{S1}$ of the transverse wave 54 and the cursor $f_1$ has the relationship represented by the following expression 13.

$$\frac{f_{S1}}{f_1} = \frac{V_S}{V_P} \quad \text{[Expression 13]}$$

where $V_s$ is the transverse sonic velocity, and $V_p$ is the longitudinal sonic velocity.

In other words, $f_{S1}=\gamma_1\cdot f_1$. $\gamma_1$ is the sonic velocity ratio between the transverse wave and the longitudinal wave.

The relationship in the sonic velocity and the frequency between the longitudinal wave and the transverse wave represented by expression 13 is not an existing universal law. According to the conventional ultrasonic theory, when a longitudinal wave is changed to a transverse wave by mode conversion (or vice versa), the wave velocity is changed by the conversion but the frequency is kept the same. However, while examining the states where waves are generated in many experiments of the same kind (iron, concrete, etc.), the present inventors always encountered a component wave generation state which cannot be explained only by this conventional ultrasonic theory.

It was found that the component wave generation state can be properly explained by assuming the presence of a mode-converted wave generated under the new relationship represented by expression 13.

This will be described in detail assuming the presence of a new mode-converted wave generated under the relationship represented by expression 13.

FIG. 22 shows a comparative spectrum in which the left most cursor position $f_1$ in FIG. 20 is changed to the transverse first-order resonant frequency $f_{S1}$.

By applying the longitudinal sonic velocity $V_P$ of 5.9 mm/μsec and the transverse sonic velocity $V_S$ of 0.54 to 0.55 $V_P$ of the probing target 30 formed of stainless steel to expression 13, $f_{S1}$=81.5 to 83.1 kHz is obtained.

The specific settings of the cursor positions shown in FIG. 22 are made such that the cursor positions match the generation of spectrum peaks represented with in FIG. 20 while $f_{S1}$ is finely changed in the range of 81.5 to 83.1 kHz.

When $f_{S1}$=83 kHz, $8f_{S1}$, $10f_{S1}$, $11f_{S1}$, $12f_{S1}$, $13f_{S1}$ and $14f_{S1}$ match the rising spectrum peaks represented with in FIG. 20. Even the position $9f_{S1}$, at which the spectrum peak is represented with in FIG. 20 and cannot be determined as a peak, matches a peak. By comparing FIG. 20 and FIG. 22, $9f_{S1}\approx 5f_1$.

FIG. 23 shows $F_j(f)$ obtained by using an expression in which $FA_j(f)$ in expression 5 is replaced with $F_j(f)$ and setting $n4_2$ to 0 and $n4_1$ to an integer of 1 or greater. $FA_j(f)$ in FIG. 24 is obtained by sampling out a spectrum of $n_B\times f_{S1}$ frequency from the resonant spectrum $F_j(f)$ in FIG. 23 with $n_B$ being set to an integer of 1 or greater.

Specifically, a spectrum of $8f_{S1}$=8×83=664 kHz is sampled out from the narrow band spectrum $FA_j(f)$ in FIG. 22 using a band pass filter (passband: 659 to 680 kHz) (corresponding to the first half of the first step). FIG. 25 shows the result of this processing as a comparative display of the component wave $GA_j(t)$ (first step and second step) ($\Delta f_B$=680−659=21 kHz).

According to the measurement diagram of FIG. 18, the line segment connecting the probes 31 and 32 is perpendicular to the flaw Z at only measurement point 4. Because of this, the analysis result shown in FIG. 25 indicates that the transverse wave 54 generated by the presence of the flaw Z in FIG. 21 is large only at measurement point 4.

The sizing coefficients used in the display in FIG. 25 are $n_{S1}$=1, $n_{S2}$=2, and $n_{S3}$=3.

In this measurement example, the spectrum at the position of the $8\times f_{S1}$ frequency is sampled out by performing band pass filtering (passband: 659 to 680 kHz) instead of performing an arithmetic operation of $S(f)^{nS4}\cdot FA_j(f)$ using the function $S(f)$ by which $f_0=8\times f_{S1}$ as shown in FIG. 5.

In summary, in the comparative display of the component wave $GA_j(t)$ shown in FIG. 26 (second step), the generation of the wave can be confirmed at measurement points 1, 2, 3, 5 and 6 at an earlier stage of the time axis (the horizontal axis), and the generation of the wave can be confirmed at measurement point 4 at a later earlier stage of the time axis.

It is determined that there is no flaw Z in the former case and that there is a flaw Z in the latter case, inside the probing target 30 right below the line segment connecting the probes 31 and 32 (third step).

As described above, a wide band ultrasonic wave is input to the probing target 30 by the transmission probe 31, and a wide band ultrasonic wave is received by the receiving probe 32. A spectrum $F_j(f)$ corresponding to the wide band received wave $G_j(t)$ is obtained by Fourier transformation. From the spectrum $F_j(f)$, a narrow band spectrum $FA_j(f)$ of a specified frequency range of $n_B\cdot f_1$ frequency ($n_B$=8, $n_B\cdot f_{S1}$=664 kHz) is extracted. A component wave $GA_j(t)$ corresponding to this is obtained by inverse Fourier transformation and provided for a comparative display and determination. Therefore, a flaw Z inside the probing target with a large scattering attenuation can be probed. In addition, the sizing coefficients $n_{S1}$, $n_{S2}$ and $n_{S3}$ are set for performing the probing with a high precision. By setting the sizing coefficients to appropriate values, the waves other than the probing target waves are removed or reduced. Therefore, the individual difference in the sizing result due to the ability of the measuring personnel can be eliminated to improve the precision of the probing. A wide band ultrasonic wave is input to the probing target 30. Since the wide band ultrasonic wave contains a low frequency component which is attenuated only very little inside the probing target 30, a flaw Z with a long probing length can be probed.

EXAMPLE 3

With reference to FIG. 27 through FIG. 41, Example 3 in which a flaw is probed inside cast iron having an especially large scattering attenuation will be described.

In Example 1, the measurement is performed on a stainless steel probing target having a thickness W of 25 mm. A longitudinal 12th-order resonant spectrum of 1420 kHz ($n_B \cdot f_{S1} = 12 \times 118.4 = 1420$ kHz) is sampled out by an arithmetic operation or band pass filtering, and the obtained component wave $GA_j(t)$ at measurement points is provided for a comparative display (see FIG. 14).

In Example 2, the measurement is performed on a stainless steel probing target having a thickness W of 20 mm. A transverse 8th-order resonant spectrum of 664 kHz ($n_B \cdot f_{S1} = 8 \times 83 = 664$ kHz) is sampled out by an arithmetic operation or band pass filtering, and the obtained component wave $GA_j(t)$ at measurement points is provided for a comparative display. In both of Examples 1 and 2, analysis is performed in a relatively high frequency band.

When the thickness of the probing target 30 formed of stainless steel is greater, or when the scattering attenuation is larger as in the case of cast iron, the flaw Z may not be probed in a superb manner in the relative high frequency band as described above.

In Example 3, a probing method for such a case where the probing is difficult will be described.

FIG. 27 shows a nuclear reactor pipe mockup model as the probing target used in Example 3.

In FIG. 27, a memory position 55 is at the side of 270 degrees for the convenience of drawing. In actuality, as shown in FIG. 28, the corresponding position on the side of 90 degrees is set as a measurement range C.

FIG. 29 is an enlarged cross-sectional view of the measurement range C. The transmission probe 31 is located in section A, and the receiving probe 32 is located in section B. The distance "a" between the centers of the probes 31 and 32 is 100 mm. A method for probing to find whether or not there is a flaw Z in the cast iron probing target right below a line segment connecting the probes 31 and 32 will be shown as an example. In the figure, reference numeral 56 is a welded section.

FIG. 30 schematically shows the ultrasonic wave propagation inside the pipe in the case where the probes 31 and 32 are located as shown in FIG. 29.

First, with reference to FIG. 30, the characteristics of the generation of a longitudinal wave 57 and a transverse wave 58 in the case where there is a flaw Z right below the line segment connecting the probes 31 and 32 will be described.

A longitudinal ultrasonic wave is input by the transmission probe 31 to right below the surface of the probing target 30 formed of cast iron. There is an ultrasonic component in an oblique direction right below the surface (the inclination $\theta_h$). A longitudinal ultrasonic wave having the inclination $\theta_h$ propagates toward the receiving probe 32 while being repeatedly reflected by the rear surface and the front surface of the plate. When the longitudinal ultrasonic wave is shielded by the flaw Z, the mode conversion phenomenon occurs at the position of shielding to generate the transverse wave 58. Then, the transverse wave 58 is released from the tip of the flaw Z and received by the receiving probe 32.

There are an infinite number of values for the inclination $\theta_h$ (directional angles). The state in which the longitudinal ultrasonic wave is shielded greatly varies in accordance with the value of the inclination $\theta_h$. This phenomenon will be described with reference to FIGS. 31(a) and (b).

As shown in FIG. 31, with an identical value of the inclination $\theta_h$, the probability at which the longitudinal ultrasonic wave is shielded is low when the flaw height $\epsilon_2$ is small as shown in FIG. 31(a). When the flaw height $\epsilon_2$ is large, the probability at which the longitudinal ultrasonic wave is shielded is high as shown in FIG. 31(b).

Even when the flaw height $\epsilon_2$ is small as shown in FIG. 31(a), the probability of shielding is increased as the inclination $\theta_h$ is decreased. In this case, the strength of the transverse wave 58 released from the tip of the flaw Z is increased.

As described above, when there is a flaw Z, the state in which the transverse wave 58 is generated at the tip of the flaw Z varies in accordance with the combination of the value of the inclination $\theta_h$ and the flaw height $\epsilon_2$.

FIG. 32 shows the time when the transverse wave 58 is generated, which changes in accordance with the flaw height $\epsilon_2$.

The change amount of the probing length $\Sigma l$ and the change amount of the flaw height $\epsilon_2$ have a linear relationship which is represented by the following expression 14.

$$\Sigma l = n_h \times (2 \times W) \quad \text{[Expression 14]}$$

W: thickness (plate thickness)

$n_h$: number of times that the wave is multi-reflected in correspondence with $\theta_h$ $\theta_h$: the inclination of the multi-reflected wave (longitudinal wave) when the wave is shielded by the flaw while the inclination is gradually reduced In order to cause the longitudinal wave 57 in FIG. 30 to be shielded by the flaw Z having a small height $\epsilon_2$, the number of times that the wave is multi-reflected needs to be increased (the inclination $\theta_h$ needs to be decreased). In this manner, as the flaw height $\epsilon_2$ is decreased, the time when the transverse wave 58 released from the tip of the flaw Z shown in FIG. 32 is received becomes later (hereinafter, referred to as "phenomenon 1").

Thus, according to the probing method of Example 3 utilizing the resonance phenomenon regarding the plate thickness (the thickness W), the length necessary for probing (the probing length $\Sigma l$) becomes long when the thickness W is large and the height $\epsilon_2$ of the flaw Z to be probed is small, as shown in FIG. 32.

One of the general physical phenomena in the ultrasonic wave propagation is scattering attenuation. Especially in a material such as cast iron or concrete, the scattering attenuation is very large. Therefore, when the probing length is increased, the ultrasonic wave propagated inside is attenuated and lost. The only way to solve the phenomenon that the probing is made impossible due to the loss of the ultrasonic wave is to use an ultrasonic wave of a frequency as low as possible (including a sonic wave, a quasi-ultrasonic wave) for analysis.

An example of such analysis will be described.

Referring to FIG. 29, the measurement point is moved in the circumferential direction of the pipe by an interval of $\Delta L = 10$ mm, and thus a multi-point measurement is performed to obtain the received wave at a total of 20 measurement points (see FIG. 30) (multi-point measurement step).

The transmission probe 31 and the receiving probe 32 respectively including the vibrators 47 and 52 (see FIG. 2 and FIG. 4) having a diameter of 15 mm$\phi$ are located as shown in FIG. 29. A step function voltage of 350 V is applied to the vibrator 47 at a time interval of 70 Hz, 200 times in total. Each time the voltage is applied, the received wave is added on the time history and averaged. The resultant wave is used as the received wave $G_j(t)$ in the analysis. Here, j is the number of the measurement point (so-called measurement point number).

This measurement is performed in a blind test. The result of processing performed without clarifying whether or not there is a flaw Z at each measurement point is shown below.

Thickness of the model of the probing target 30 formed of cast iron is W=70 mm. In this case, the longitudinal first-order resonant frequency with respect to the thickness W can be obtained by expression 4 with the cast iron longitudinal sonic velocity $V_P$ being set to 5.0 mm/µsec. Namely, $$f_1=10^6/(2\times70\div5.0)=35.7 \text{ kHz}$$

As in Example 1, a very narrow band component wave, in which the central frequency is the 4th-order longitudinal resonant frequency, i.e., $4\times f_1=4\times35.7=142.8$ kHz, is extracted. The component wave $GA_j(t)$ corresponding to this is provided as a comparative example in FIG. 33.

With the component wave shown as the comparison example of FIG. 33, the presence of the flaw Z cannot be confirmed. It is understood that in the band in the vicinity of the central frequency of 142.8 kHz, the analysis is impossible due to the scattering phenomenon.

FIG. 34 is obtained as follows. The received wave $G_j(t)$ is processed with Fourier transformation, and the obtained narrow band spectrum $FA_j(f)$ is provided for a comparative display. Using the value of $f_1=35.7$ kHz, a plurality of cursors $f_1$, $2f_1$, $3f_1$, . . . $n_4f_1$ are generated. Processing is performed automatically or manually by an external instruction, such that the leftmost cursor $f_1$ matches a rising spectrum peak having a large value in the vicinity of the longitudinal resonant frequency 35.7 kHz with respect to the cast iron plate thickness W. In the right part of FIG. 34, the component wave $GA_j(t)$ calculated by expression 9 described above is also provided.

The cursor $f_1$ is set in the vicinity of the longitudinal resonant frequency 35.7 kHz with respect to the cast iron plate thickness W. The other plurality of cursors are set at positions obtained by multiplying $f_1$ by an integer. In FIG. 34, the generation of a relatively small spectrum peak is confirmed as represented with forward to the cursor position $f_1$. This is a spectrum of the transverse wave 58 generated from the tip of the flaw Z in FIG. 30. The value of the rising frequency $f_{S1}$ at which the transverse wave 58 (first-order resonant frequency of the transverse wave) is 19.5 kHz.

Now, expression 13 is used for checking. The longitudinal sonic velocity $V_P$ of cast iron is 5.0 mm/µsec and the transverse sonic velocity $V_S$ of cast iron is 2.8 mm/µsec. Therefore, the left term of expression 13 is $f_{S1}/f_1=19.5/35=0.557$. The right term of expression 13 is $V_S/V_P=2.8/5=0.56$. It is confirmed that the values of the cursor $f_1$ and the rising frequency $f_{S1}$ of the transverse wave 58 in FIG. 34 fulfill expression 13.

Next, $f_{S1}=\gamma_1\cdot f_1$ is calculated where $\gamma_1$ is the sonic velocity ratio between the transverse wave and the longitudinal wave of the pipe. In the spectrum comparison diagram of FIG. 35 which schematically shows FIG. 34, a group of dashed line cursors $f_{S1}$, $2f_{S1}$, $3f_{S1}$, . . . are shown.

The value of $f_{S1}$ is slightly adjusted such that all the plurality of dashed line cursors $f_{S1}$, $2f_{S1}$, $3f_{S1}$, . . . match a rising spectrum peak in the narrow band spectrum $FA_j(f)$. The adjustment may be performed automatically, or manually while visually checking FIG. 35 on the computer display screen (the display device 41 shown in FIG. 1).

The value of the rising frequency $f_{S1}$ or $2f_{S1}$ of the transverse wave spectrum, the predetermined value $f_a$ and the predetermined value $\Delta f_0$ are used to perform an arithmetic operation of $f_0=f_0+\Delta f_0$, with the initial value of $f_0$ being set to $f_1-f_a$ or $2f_{S1}-f_a$. Each time the value of $f_0$ is changed, a narrow band spectrum is sampled out with the value of $f_0$, and thus the $FA_j(t)$ shown in FIG. 36 is obtained.

The component wave $GA_j(t)$ is obtained by expression 9 (first step) and provided for a comparative display (second step) as shown in FIG. 37.

The specific processing performed to obtain FIG. 37 is as follows. An arbitrary function $S(f)$ for sampling out the spectrum $FA_j(t)$ is obtained as the following expression 15.

$$0 \leq f \leq 2f_0 \quad \text{[Expression 15]}$$
$$S(f) = \sin\frac{\pi}{2}\left(\frac{f}{2f_0}\right)\cdot\cos\frac{\pi}{2}\left(\frac{f}{2f_0}\right)$$
$$f > 2f_0$$
$$S(f) = 0.0$$

$FA_j(f)=S(f)^{nS4}\cdot F_j(f)$ is obtained by expression 2. $FA_j(f)$ is applied to expression 9 to calculate the component wave $GA_j(t)$ (first step). The component wave $GA_j(t)$ is provided for a comparative display, with the sizing coefficients $n_{S1}$, $n_{S2}$, $n_{S3}$ and $n_{S4}$ being set as $n_{S1}=1.4$, $n_{S2}=8$, $n_{S3}=1.0$ and $n_{S4}=300$ (second step). With FIG. 37, the generation of the component wave is confirmed only at measurement points 7, 8, 9, 10 and 11 (third step).

The analysis processing of FIG. 37 will be described in more detail. FIG. 37 is obtained with central frequency $f_0$ for spectrum extraction being set to the vicinity of the transverse first-order resonant frequency $f_{S1}$ of 19.5 kHz, more precisely to 20.4 kHz. Because the frequency is low, there is a possibility of error in the recognition of the width of the flaw due to the phenomenon shown in FIG. 38.

Namely, in FIG. 38, the line segment connecting the probes 31 and 32 crosses the flaw Z at the measurement j. The line segment does not cross the flaw Z at the measurement point j+1. As the frequency becomes lower, the amplitude of the wave propagated from a path 59 to a path 60 increases. As a result, the measurement j+1 is incorrectly recognized as a tip of the flaw Z. The wrong measurement regarding the sizing of the flaw Z due to this phenomenon can be eliminated by extracting the spectrum $FA_j(t)$ in a higher frequency range.

FIG. 39 shows a spectrum $FA_j(f)$ extracted with the central frequency $f_0$ being set to the vicinity of the transverse second-order resonant frequency ($2f_{S1}=40$ kHz), more precisely to 42 kHz.

The sizing coefficients are the same as in the extraction shown in FIG. 37 ($n_{S1}=1.4$, $n_{S2}=8$, $n_{S3}=1.0$ and $n_{S4}=300$).

Now, FIG. 37 and FIG. 39 will be compared. In FIG. 37, it is analyzed that there is a flaw Z at measurement points 7, 8, 9, 10 and 11, whereas in FIG. 39, it is analyzed that there is a flaw Z at measurement points 8, 9,10 and 11. FIG. 39 indicates that there is no flaw Z right below the line segment connecting the probes 31 and 32 at measurement point 7, but there is a tip of the flaw Z in the vicinity thereof for the reason described with reference to FIG. 38.

The extraction of the component wave $GA_j(t)$ in FIG. 37 is performed as follows. From the longitudinal first-order resonant frequency ($f_1=35.7$ kHz) in the case where the thickness of the target probe 30 formed of cast iron is W=70 mm, the transverse first-order resonant frequency is obtained as $f_{S1}=0.56\times35.7=20$ kHz, using the sonic velocity ratio $\gamma_1$ of 0.56 between the transverse wave and the longitudinal wave (in the case of cast iron). As a result, the central frequency of the spectrum is $f_0=f_{S1}$. Thus, it may be determined that the component wave $GA_j(t)$ at measurement point 7 is the wave in the paths 59 and 60 shown in FIG. 38. In this manner, it is determined that there is a flaw Z at measurement points 8, 9, 10 and 11 as a result of comparing the generation states of the component wave $GA_j(t)$ in FIG. 37 and FIG. 39.

The time when the component wave $GA_j(t)$ is generated in FIG. 39 at measurement points 8, 9, 10 and 11 linearly changes.

According to the above explanation on the phenomenon 1, the height $\epsilon_2$ of the flaw Z to be probed changes at measurement points 8 through 11.

Example 3 summaries the results of the blind probing. Since these probing results match the actual state of the flaw Z, this analysis method has been proven to be correct.

Important points in the extraction of the component wave in FIG. 39 will be described.

The nominal thickness W of the cast iron plate used in Example 3 is 70 mm. In general, the longitudinal sonic velocity $V_P$ of cast iron is 5.0 mm/µsec, and the sonic velocity ratio (sonic velocity ratio $\gamma_1$) between a transverse wave and a longitudinal wave is 0.56.

The transverse second-order resonant frequency which is generated at the tip of the flaw Z in FIG. 39 is, as described above, $$f_{S2}=2\times\{10^6/(2\times70\div0.56V_P)\}=40 \text{ kHz}.$$

On the other hand, the accurate central position of the frequency of the extracted component wave $GA_j(t)$ in FIG. 39, i.e., the central frequency ($f_0$) thereof is 42 kHz. The cause of the difference between the frequency 40 kHz and 42 kHz will be described.

The thickness of the cast iron plate W of 70 mm, the longitudinal sonic velocity $V_P$ of 5.0 mm/µsec, the sonic velocity $\gamma_1$ of 0.56 are nominal. If the actual values are appreciated as being offset from the nominal values, it is understandable there is a change amount of the frequency $\Delta f = 42-40 = 2$ kHz.

The change amount $\Delta f$ can be easily specified by the following automatic processing.

In the above explanation on the sizing coefficient $n_{S4}$, the function $S(f)$ is defined. Where the received wave spectrum is $F_j(f)$, one method for extracting the spectrum $FA_j(f)$ having the central frequency $f_0$ is the following. A combination function $S(f)$ of a sine (sin) function which is 0.0 at a frequency of 0.0 and at a frequency of $2f_0$ and is 1.0 at a frequency of $f_0$, and a function which is 0.0 at a frequency of $2f_0$ or greater, is obtained as $S(f)$. Then, the calculation of $FA_j(f)=S(f)^{nS4}\cdot F_j(f)$ is performed as described above.

$n_{S4}$ is an integer of 1 or greater. As $n_{S4}$ is greater, the band of the extracted narrow band spectrum $FA_j(f)=S(f)^{nS4}\cdot F_j(f)$ is smaller. Specifically, the component wave $GA_j(t)$ in FIG. 39 is obtained as follows. The following expression 16 is performed with the initial value of $f_0$ being set to 37 kHz, and the predetermined value $\Delta f_H$ being set to 0.1 kHz.

$$f_0=f_0+\Delta f_H \quad \text{[Expression 16]}$$

Each time the value of $f_0$ is increased by 0.1 kHz, the calculation of $FA_j(f)=S(f)^{nS4}\cdot F_j(f)$ is performed. The component wave $GA_j(t)$ in this case is calculated using the following expression 17 (first step).

$$GA_j(t) = \int_{-\infty}^{\infty} (S(f)^{nS4} \cdot F_j(f) \cdot e^{i\omega t}) df \quad \text{[Expression 17]}$$

The comparative display of the component wave $GA_j(t)$ (second step) is visually checked.

The value of $f_0$ when the component wave $GA_j(t)$ of FIG. 39 is obtained is recognized as the frequency at which the wave to be probed (transverse wave generated by the presence of the flaw Z) is generated with a large amplitude, and is defined as $f_{DR}$. The sizing coefficients are $n_{S1}=1.4$, $n_{S2}=8$, $n_{S3}=1.0$ and $n_{S4}=300$.

How important it is to accurately select the value of $f_{DR}$ (frequency at which the transverse wave is generated with a large amplitude) will be described.

FIG. 40 shows a part of the component wave $GA_j(t)$ of expression 9 which is obtained each time expression 16 is applied. As is clear from FIG. 40, only the generation of a scattering wave can be confirmed but the presence of the flaw Z is not clearly shown. When the central frequency $f_0$ is increased from that of the component wave comparative display of FIG. 39 which specifies the presence of the flaw Z (from $f_0=42$ kHz) (third step), the component wave comparative display of FIG. 39 is changed to FIG. 40, which shows the generation of the scattering wave. Therefore, it is important to accurately select the value of $f_{DR}$.

FIG. 39 is obtained by multiplying the component wave $GA_j(t)$ by the TGC (time gate control) function as shown here at the position of time $t_g=914$ µsec. FIG. 40 is obtained by the same multiplication performed at the position of time $t_g=713$ µsec. This processing is performed in order to apparently eliminate the waves generated at an earlier point in time.

FIG. 41 shows a component comparative display obtained by eliminating the results of TGC processing from the analysis results shown in FIG. 39 in which the presence/absence of the flaw Z is confirmed. As is clear from comparing FIG. 39 and FIG. 41, the presence/absence of the flaw Z can be confirmed more clearly in FIG. 39 with the TGC processing.

As described above, a wide band ultrasonic wave is input to the probing target 30 by the transmission probe 31, and a wide band ultrasonic wave is received by the receiving probe 32. A spectrum $F_j(f)$ corresponding to the wide band received wave $G_j(t)$ is obtained by Fourier transformation. From the spectrum $F_j(f)$, a narrow band spectrum $FA_j(f)$ of a specified frequency range of $n_B \cdot f_1$ frequency ($n_B=2$, $n_B \cdot f_1=40$ kHz which is in the vicinity of 42 kHz) is extracted. A component wave $GA_j(t)$ corresponding to this is obtained by inverse Fourier transformation and provided for a comparative display and determination. Therefore, a flaw Z inside the probing target with a large scattering attenuation can be probed. In addition, the sizing coefficients $n_{S1}$, $n_{S2}$ and $n_{S3}$ are set for performing the probing with a high precision. By setting the sizing coefficients to appropriate values, the waves other than the probing target waves are removed or reduced. Therefore, the individual difference in the sizing result due to the ability of the measuring personnel can be eliminated to improve the precision of the probing. A wide band ultrasonic wave is input to the probing target 30. Since the wide band ultrasonic wave contains a low frequency component which is attenuated only very little inside the probing target 30, a flaw Z with a long probing length can be probed.

EXAMPLE 4

With reference to FIG. 42 through FIG. 45, Example 4 regarding a probing method for extracting a longitudinal wave generated at a tip of the flaw Z will be described.

In the schematic view of ultrasonic wave propagation descried above with reference to FIG. 30, the wave generated at the tip of the flaw Z is not limited to the transverse wave 58, but may be a longitudinal wave needless to say. In Example 4, the longitudinal wave is extracted.

FIG. 42 schematically shows multi-reflection regarding the probing target 30 formed of cast iron. Two propagation paths are shown with a solid line and a dashed line. The thickness W=70 mm, and the distance a=100 mm. The solid line directional angle is represented with $\theta_A$, and the dashed line directional angle is represented with $\theta_B$, while $\theta_A$ and $\theta_B$ are slightly changed ($\theta_A < \theta_B$).

It is shown here that in the propagation path represented with the solid line, the fourth multi-reflected wave is received by the receiving probe 32, whereas in the propagation path represented with the dashed line, the fourth multi-reflected wave not is received by the receiving probe 32.

FIG. 43 shows that among the waves in the above two propagation path, the wave in the propagation path which is represented with the dashed line and is not received by the receiving probe is shielded by the flaw Z. In this case, a scattering phenomenon occurs at the position of shielding, and a fan-like scattering wave is generated as shown in FIG. 43. A part of such a fan-like scattering wave is received by the receiving probe 32. The scattering wave includes a longitudinal wave 61 and a transverse wave 62. In Example 4, the longitudinal wave 61 is used for analysis.

In the schematic view of longitudinal wave propagation in FIG. 42, only the wave propagated in the solid line path is received, and the wave propagated in the dashed line path is not received.

In FIG. 43, both of the wave propagated in the solid line path and the scattering wave (the longitudinal wave 61) generated by the flaw Z are received by the receiving probe 32. Thus, the form and amplitude of the received waves obtained by the receiving probe 32 vary depending on whether or not there is a flaw Z in the cast iron right below the line segment connecting the probes 31 and 32.

An example of probing for a flaw utilizing this phenomenon will be described using the received wave $G_j(t)$.

The thickness W of the cast iron pipe as the probing target 30 used in Example 4 is 70 mm as in Example 3. Therefore, the frequency of the longitudinal multi-reflected wave is obtained as follows. The cast iron longitudinal sonic velocity $V_P$=5.0 mm/μsec is substituted into expression 4, i.e., $f_1 = 10^6 / (2W \div V_P)$. As a result, $$f_1 = 10^6/(2 \times 70 \div 5.0) = 35.7 \text{ kHz}.$$

The analysis is performed in substantially the same manner as the analysis for obtaining the component wave comparative display in FIG. 39 and FIG. 40 in Example 3. The initial value of the central frequency $f_0$ for spectrum extraction of expression 16 is set as $f_0$=35 kHz (a value slightly smaller than 35.7 kHz, which is the theoretical value of resonant frequency), and the increase of the frequency, i.e., the predetermined value $\Delta f_H$ is set to 0.5 kHz. Each time the calculation of expression 16, $$f_0 = f_0 + \Delta f_H \text{ is}$$

is performed, the narrowband spectrum $FA_j(f)$ is calculated using expression 2, $$FA_j(f) = S(f)^{nS4} \cdot F(f).$$

Then, the component wave $GA_j(f)$ is calculated (first step) using expression 9.

$$GA_j(t) = \int_{-\infty}^{\infty} (FA_j(f) \cdot e^{i\omega t}) df$$

Then, the resultant component wave $GA_j(f)$ is visually checked. Component wave comparative displays obtained during this process are shown in FIG. 44 and FIG. 45. The sizing values used for obtaining the component waves in FIG. 44 and FIG. 45 are $n_{S1}$=1.0, $n_{S2}$=8, $n_{S3}$=1.0 and $n_{S4}$=500 (second step).

FIG. 44 shows a component wave comparative display at $f_0$=36.5 kHz obtained by adding $\Delta f_H$=0.5×3=1.5 kHz to $f_0$=35 kHz. FIG. 45 (comparative example) shows a component wave comparative display at $f_0$=38.5 kHz obtained by adding $\Delta f_H$=0.5×7=3.5 kHz to $f_0$=35 kHz.

Although not shown, component wave comparison was performed for $f_0$=35 kHz. With $f_0$=35 kHz (not shown; the wave is generated in substantially the same manner as in the comparative example in FIG. 45), the flaw Z was not confirmed.

When the value of $f_0$ slightly exceeds 35.7 kHz, the generation of a large component wave $GA_j(t)$ is confirmed at measurement points 7, 8, 9, 10 and 11 as shown in FIG. 44 (in this case, $f_0$=36.5 kHz). Thus, the presence of the flaw Z was confirmed (third step).

When the value of $f_0$ is increased more (farther from the resonant frequency of 35.7 kHz), the generation state of the component wave $GA_j(t)$ is disturbed as shown in FIG. 45.

As described above, a wide band ultrasonic wave is input to the probing target 30 by the transmission probe 31, and a wide band ultrasonic wave is received by the receiving probe 32. A spectrum $F_j(f)$ corresponding to the wide band received wave $G_j(t)$ is obtained by Fourier transformation. From the spectrum $F_j(f)$, a narrow band spectrum $FA_j(f)$ of a specified frequency range of $n_B \cdot f_1$ frequency ($n_B$=1, $n_B \cdot f_1$=36.5 kHz, which is in the vicinity of 35.7 kHz; in more detail, the central frequency for spectrum extraction $f_0 = f_0 + \Delta f_H$) is extracted. A component wave $GA_j(t)$ corresponding to this is obtained by inverse Fourier transformation and provided for a comparative display and determination. Therefore, a flaw Z inside the probing target with a large scattering attenuation can be probed. In addition, the sizing coefficients $n_{S1}$, $n_{S2}$ and $n_{S3}$ are set for performing the probing with a high precision. By setting the sizing coefficients to appropriate values, the waves other than the probing target waves are removed or reduced. Therefore, the individual difference in the sizing result due to the ability of the measuring personnel can be eliminated to improve the precision of the probing. A wide band ultrasonic wave is input to the probing target 30. Since the wide band ultrasonic wave contains a low frequency component which is attenuated only very little inside the probing target 30, a flaw Z with a long probing length can be probed.

The component waves $GA_j(t)$ and $GB_j(t)$ shown in FIG. 14 and FIG. 15 in Example 1 and the component wave $GA_j(t)$ shown in FIG. 44 in Example 4 are both obtained by extracting a longitudinal resonant spectrum with respect to the thickness of the stainless steel or cast iron probing targets. In FIG. 14 and FIG. 15, the component wave is generated at measurement points with no flaw Z; whereas in FIG. 44, the component wave is generated at measurement points with a flaw Z. Namely, the presence/absence of the generation of the component wave is opposite. This phenomenon is considered to have occurred for the following difference between Example 1 and Example 4.

1) In Example 1, the component wave $GA_j(t)$ is extracted at the frequency obtained by the expression regarding the longitudinal resonant frequency $f_1$ where $n_B$ is 12 (12×118.4=1420 kHz). In Example 4, the component wave $GA_j(t)$ is extracted at 36.5 kHz, which is in the vicinity of the frequency obtained by the expression regarding the longitudinal resonant frequency $f_1$ where $n_B$ is 1 (35.7 kHz). At 1420 kHz and 35.7 kHz, the scattering state and the scattering attenuation degree of the ultrasonic wave are significantly different. Especially in the case of the longitudinal ultrasonic wave generated by the flaw Z, the difference in the scattering state and the scattering attenuation degree is expected to be doubled.

2) In Example 1, the flaw Z is linear; whereas in Example 4, the flaw Z is planar. The state in which the longitudinal resonant wave is shielded with respect to the thickness W of the plate is different.

The above phenomenon that the presence/absence of the generation of the component wave $GA_j(t)$ is opposite is considered to have occurred for the reasons 1) and 2).

In Example 1 and Example 2 also, each time the calculation of expression 16 ($f_0 = f_0 + \Delta f_H$) is performed, the narrow band spectrum $FA_j(f)$ may be calculated by expression 2 and the component wave $GA_j(t)$ may be calculated by expression 9.

According to another example, the narrow band spectrum $FA_j(f)$ may be obtained as follows. A combination function $S(f)$ is obtained by an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater. The function $S(f)$, the sizing coefficient $n_{S4}$ (the value of $n_{S4}$ may be preset or externally input via the keyboard 42 or the like), and a predetermined value $\Delta f_0$ are used for the following processing. The longitudinal cursor $f_1$ or $f_{S1}$ is represented as $f_1$.

The initial value of the frequency $f_0$ is set as $f_0 = n_B \cdot f_1 - \Delta f_0$, the final value of the frequency $f_0$ is set as $f_0 = n_B \cdot f_1 + \Delta f_0$, and the change amount of the frequency is set to $\Delta f_H$.

Each time the calculation of, $$f_0 = f_0 + \Delta f_H$$

is performed, the narrow band spectrum $FA_j(f)$ is obtained by the arithmetic operation of, $$FA_j(f) = S(f)^{nS4} \times F_j(f).$$

Each time $FA_j(f)$ is obtained, the first through third steps described above are repeated.

The arithmetic operation of $f_0 = f_0 + \Delta f_H$, the arithmetic operation of $FA_j(f) = S(f)^{nS4} \times F_j(f)$, and the first through third steps are stopped by an external instruction or automatically.

According to still another example, the narrow band spectrum $FA_j(f)$ may be obtained as follows. A predetermined value $\Delta f_a$ (the value of $\Delta f_a$ may be preset or externally input via the keyboard 42 or the like) is used for the following processing. The longitudinal cursor $f_1$ or $f_{S1}$ is represented as $f_1$.

A function $S(f)$ which is 0.0 at a frequency of $0 \leq f < f_0 - \Delta f_a$, 1.0 at a frequency of $f_0 - \Delta f_a \leq f < f_0 + \Delta f_a$, and 0.0 at a frequency of $f > f_0 + \Delta f_a$, and a predetermined value $\Delta f_0$ are used.

The initial value of the frequency $f_0$ is set as $f_0 = n_B \cdot f_1 - \Delta f_0$, the final value of the frequency $f_0$ is set as $f_0 = n_B \cdot f_1 + \Delta f_0$, and the change amount of the frequency is set to $\Delta f_H$.

Each time the calculation of, $$f_0 = f_0 + \Delta f_H$$

is performed, the narrow band spectrum $FA_j(f)$ is obtained by the operation of, $FA_j(f) = S(f) \times F_j(f)$ or band pass processing. Each time $FA_j(f)$ is obtained, the first through third steps described above are repeated. The arithmetic operation of $f_0 = f_0 + \Delta f_H$, the arithmetic operation of $FA_j(f) = S(f) \cdot F_j(f)$, and the first through third steps are stopped by an external instruction or automatically.

According to still another example, the narrow band spectrum $FA_j(f)$ may be obtained as follows. Either one of a combination function $FiLT(t)$ obtained by combining a sin function which is 0.0 at time 0, 1.0 at time $t_g$, and 0.0 at time $2t_g$, and a function which is 0.0 at time $2t_g$ or greater; a combination function $FiLT(t)$ obtained by combining a function which is 0.0 at time 0 to $t_g - \Delta t$, a sin function which is 0.0 at time $t_g - \Delta t$, 1.0 at time $t_g$, and 0.0 at time $t_g + \Delta t$, and a function which is 0.0 at time $t_g + \Delta t$ or greater using the predetermined value $\Delta t$; and a combination function $FiLT(t)$ obtained by combining an increase function which is 0.0 at time 0 and 1.0 at time $t_g$ and a function which is 1.0 at time $t_g$ or greater is selected by an external instruction via the keyboard 42 or the like. The predetermined value $\Delta t_g$ and the predetermined coefficient n5 are used. The initial value of time $t_g$ is 0.0. Each time the arithmetic operation of, $$t_g = t_g + \Delta t_g$$

is performed, the component wave $GB_j(t)$ is obtained by the arithmetic operation of, $$GB_j(t) = FiLT^{n5}(t) \cdot GA_j(t).$$

Each time $GB_j(t)$ is obtained, $GA_j(t)$ in the second and third steps is replaced with $GB_j(t)$.

The arithmetic operation of $t_g = t_g + \Delta t_g$, the arithmetic operation of $GB_j(t) = FiLT^{n5}(t) \cdot GA_j(t)$, and the second and third steps are stopped by an external instruction or automatically.

The elements of the present invention and the elements in the above-described embodiment correspond as follows.

The inverse transformation section of the present invention corresponds to the CPU 40 of the embodiment; and the comparative display section and the determination section of the present invention correspond to the display device 41 of the embodiment.

The invention is not limited to the above-described embodiment.

INDUSTRIAL APPLICABILITY

The present invention is applicable to probing of a flaw inside a probing target such as a metal pipe formed of stainless steel, inconel, cast iron or the like, an architecture or construction structure of steel or the like.

BRIEF DESCRIPTION OF THE DRAWINGS

[FIG. 8] A view illustrating a comparative example of multi-point measurement.
[FIG. 31] A view illustrating a state where a longitudinal wave is shielded by a flaw.
[FIG. 46] A view illustrating the difference between a narrow band ultrasonic wave and a wide band ultrasonic wave.

DESCRIPTION OF THE REFERENCE NUMERALS

Figure 1:
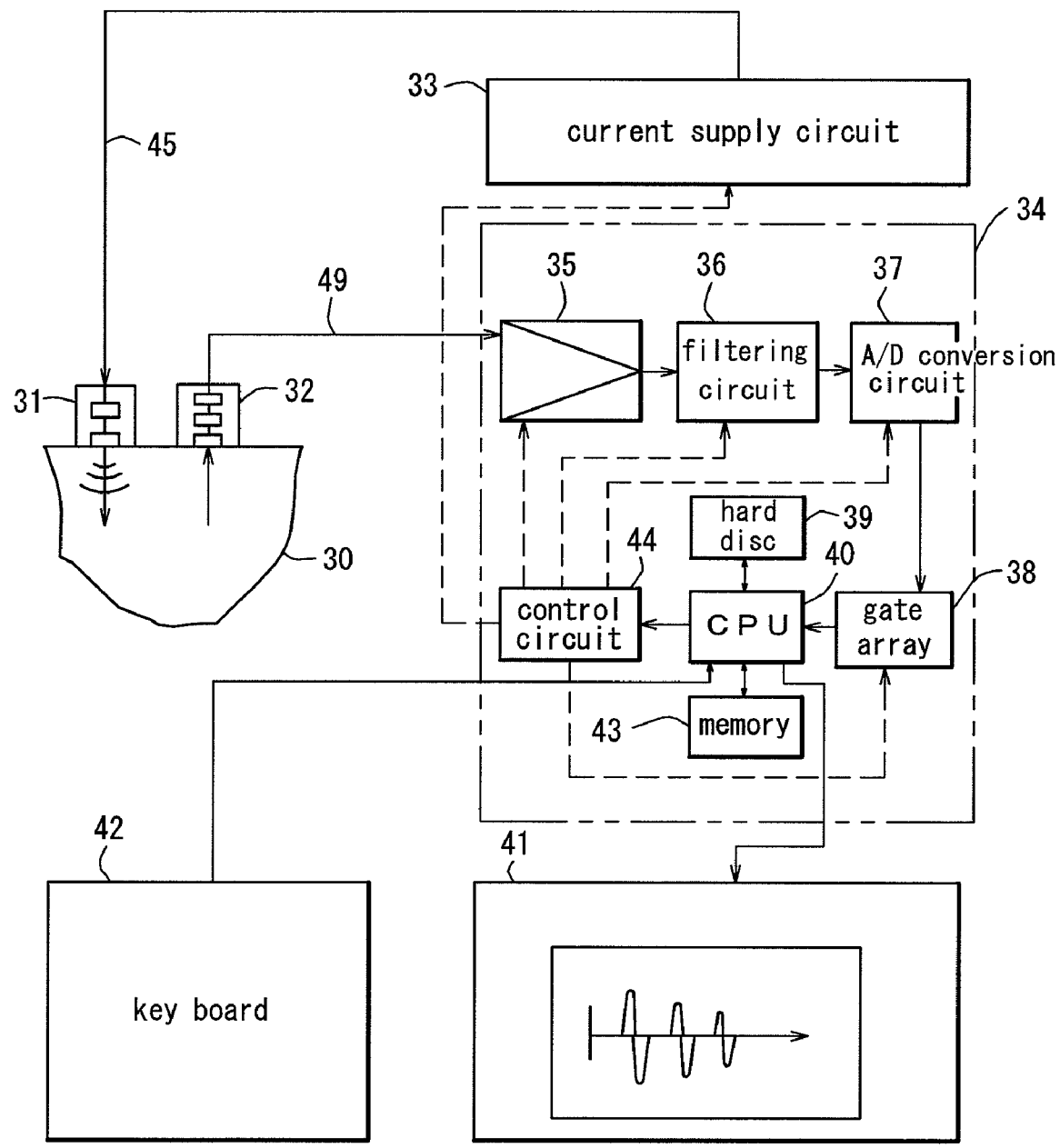
[FIG. 1] A block diagram of an ultrasonic probing apparatus usable for an ultrasonic probing method according to the present invention.
Figure 2:
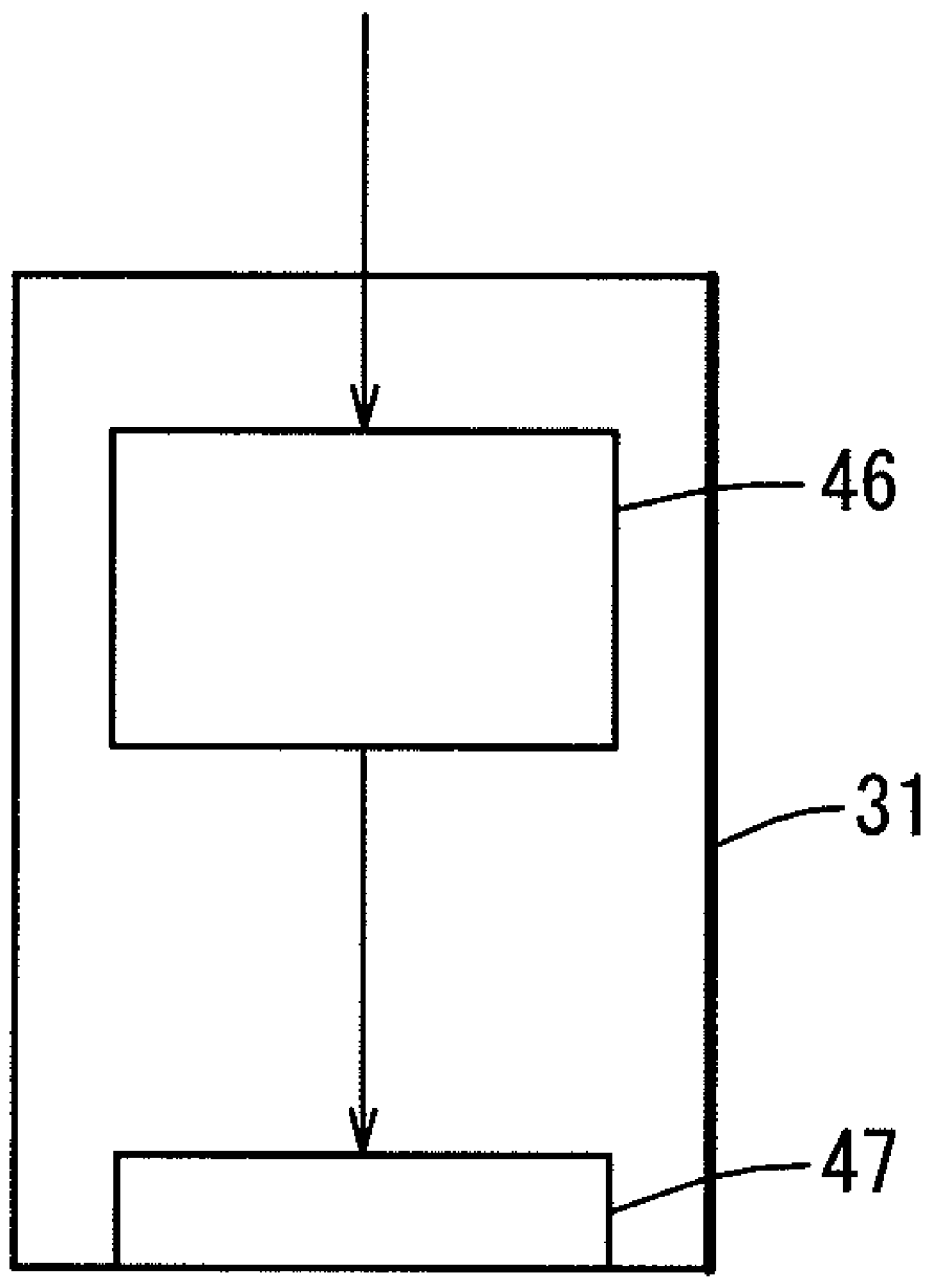
[FIG. 2] A block diagram of a transmission probe.
Figure 3:
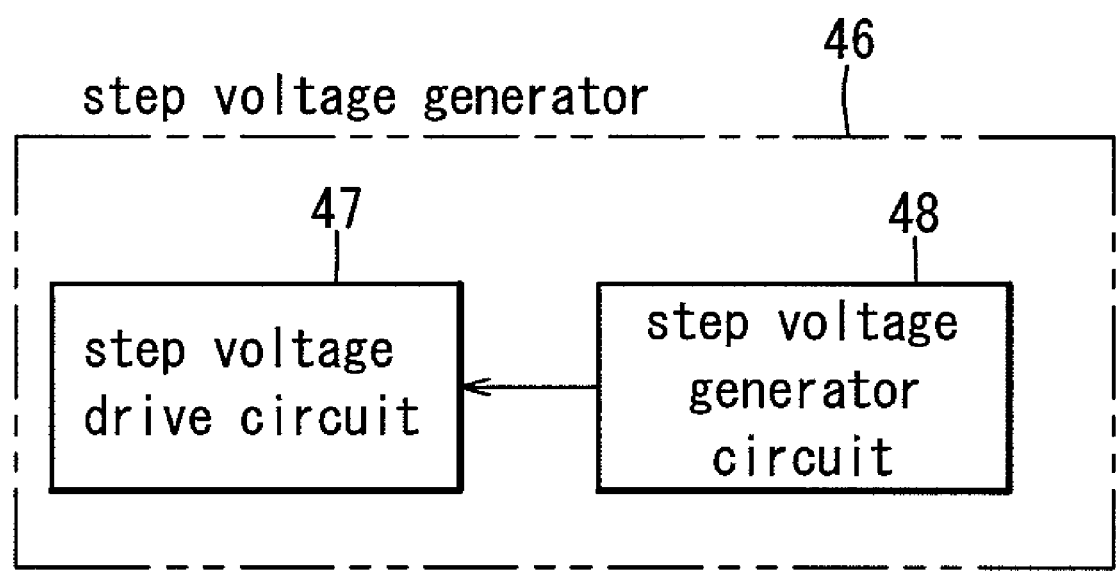
[FIG. 3] A block diagram of a step voltage generator.
Figure 4:
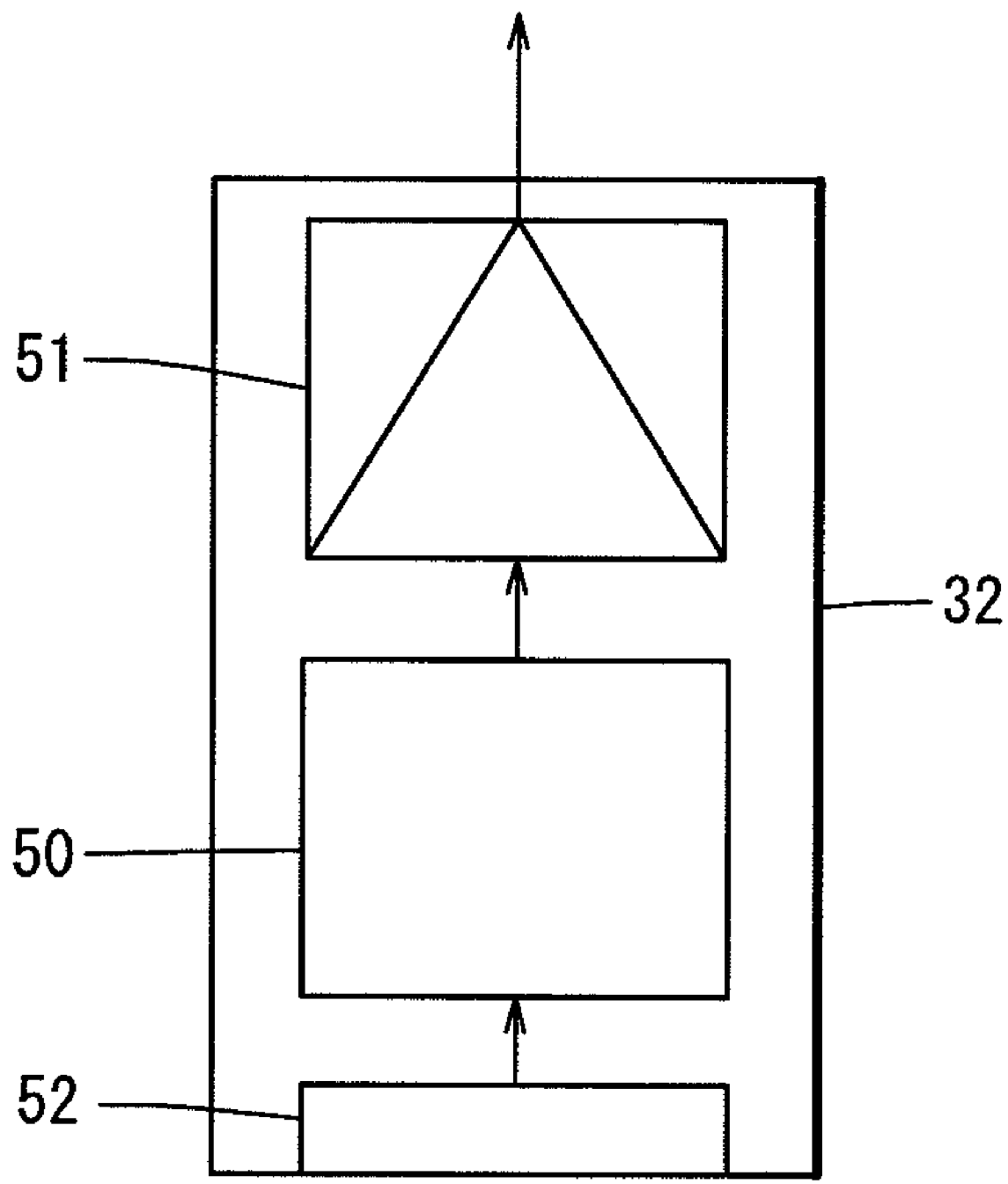
[FIG. 4] A block diagram of a receiving probe.
Figure 5:
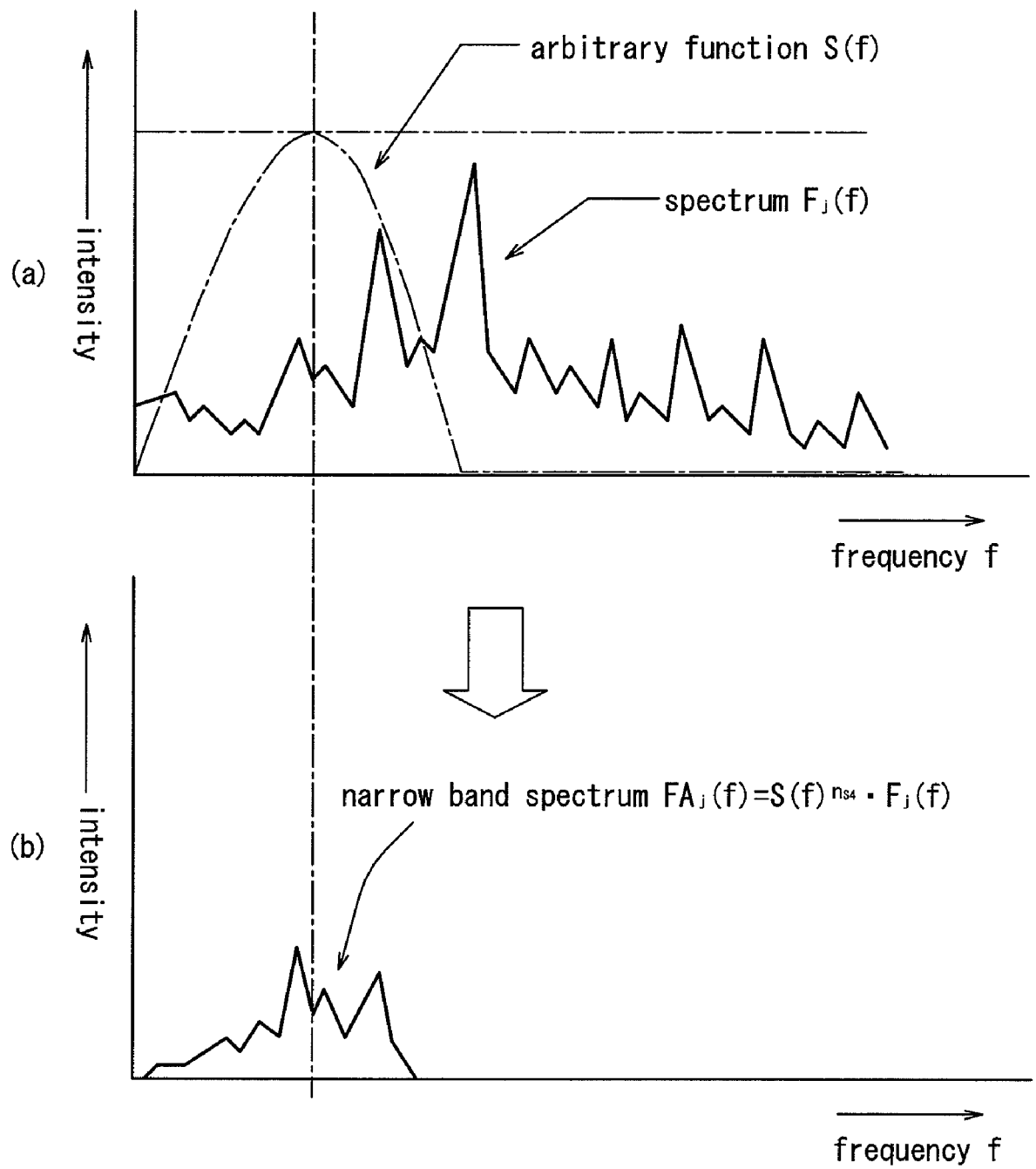
[FIG. 5] A view illustrating sampling-out of a narrow band spectrum.
Figure 6:
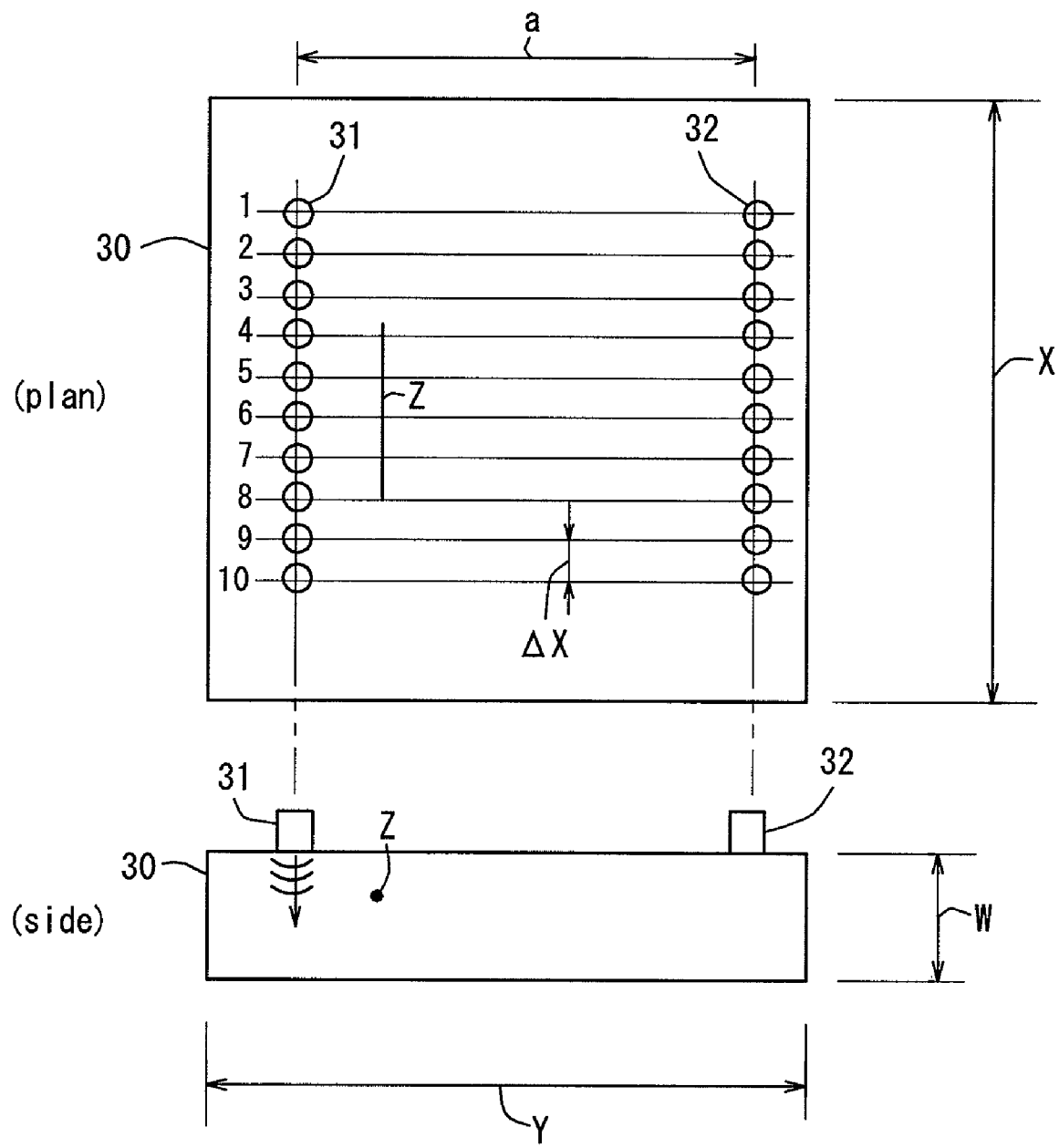
[FIG. 6] A view illustrating an example of a probing target.
Figure 7:
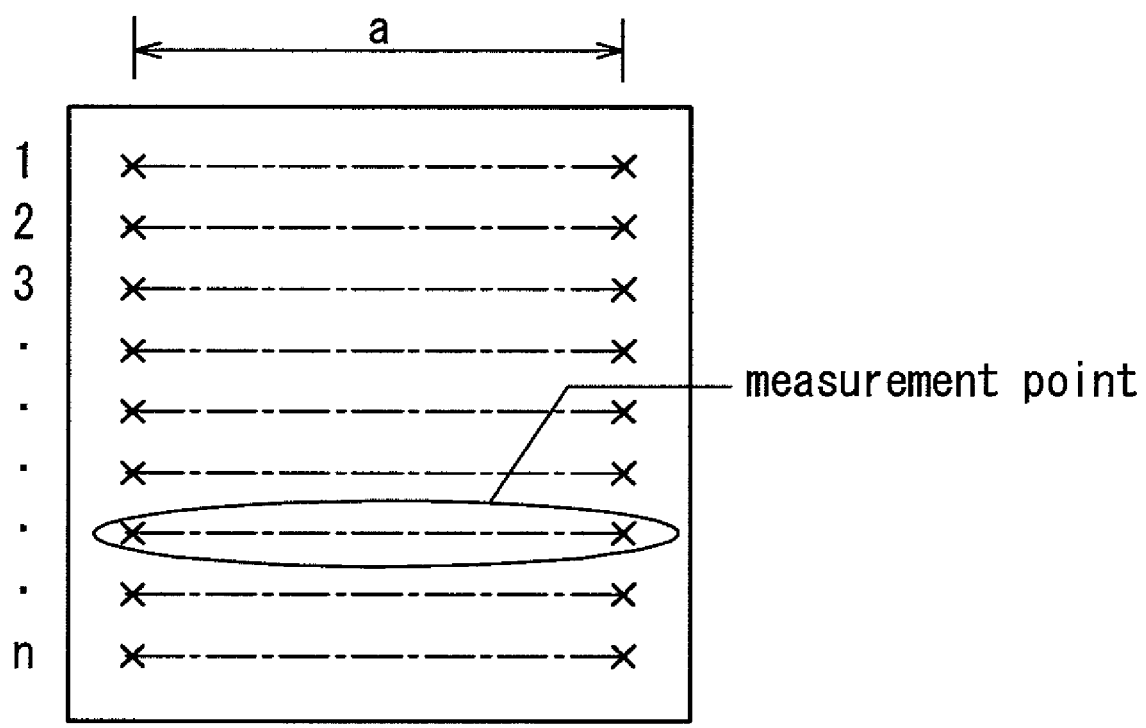
[FIG. 7] A view illustrating an example of multi-point measurement.
Figure 9:
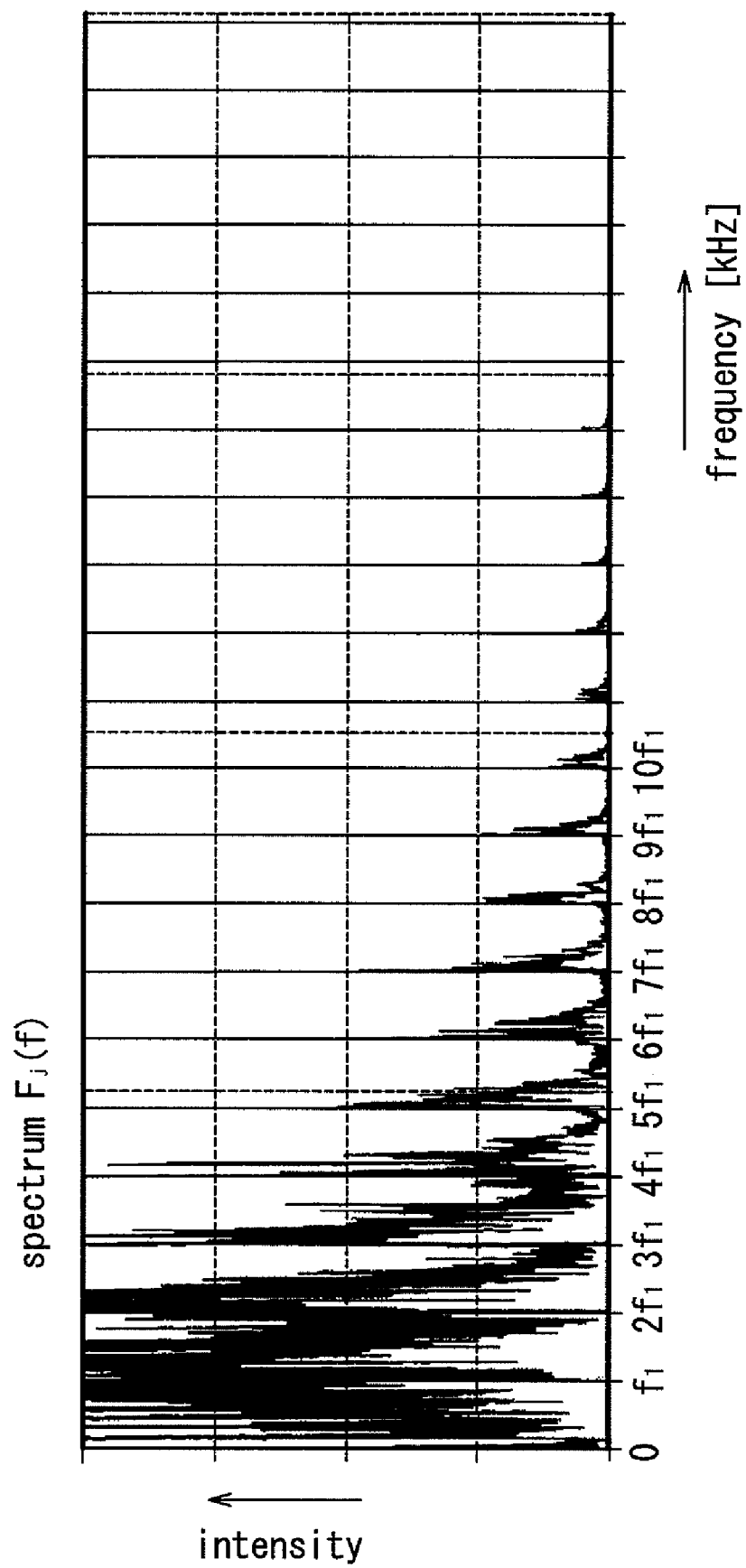
[FIG. 9] A comparative display of spectrum $F_j(f)$.
Figure 10:
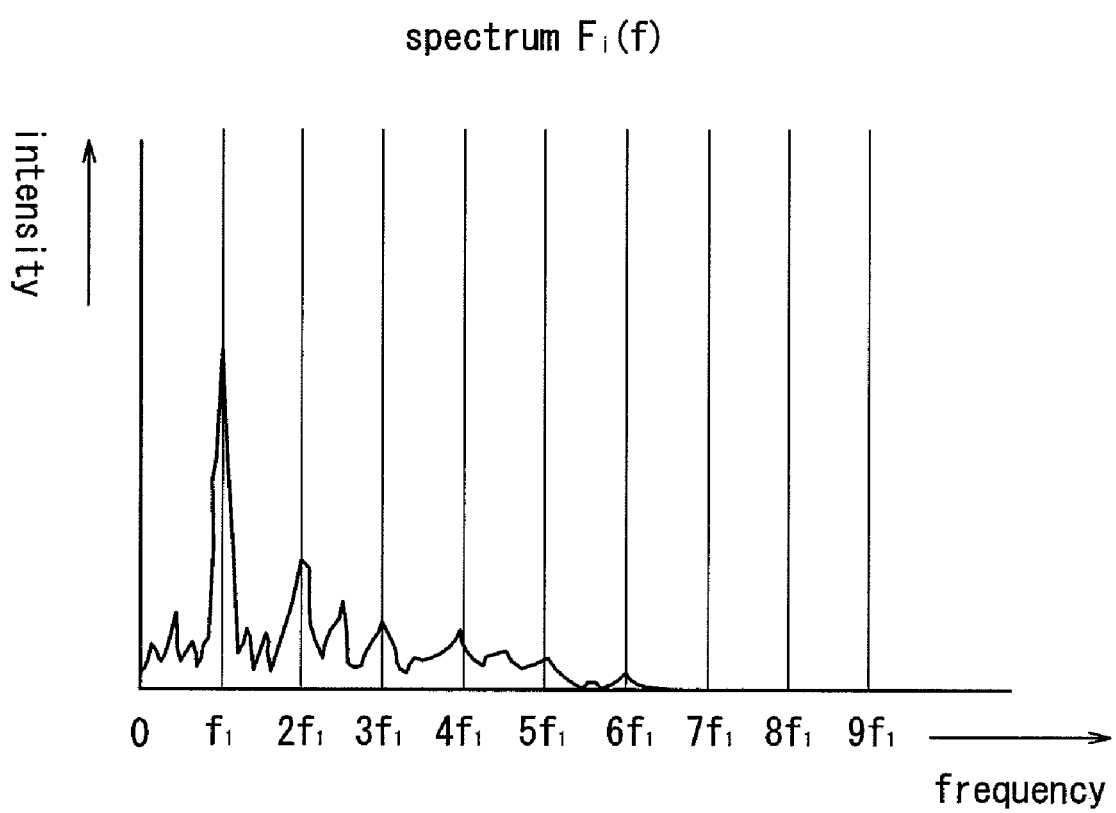
[FIG. 10] A schematic view of the comparative display of FIG. 9.
Figure 11:
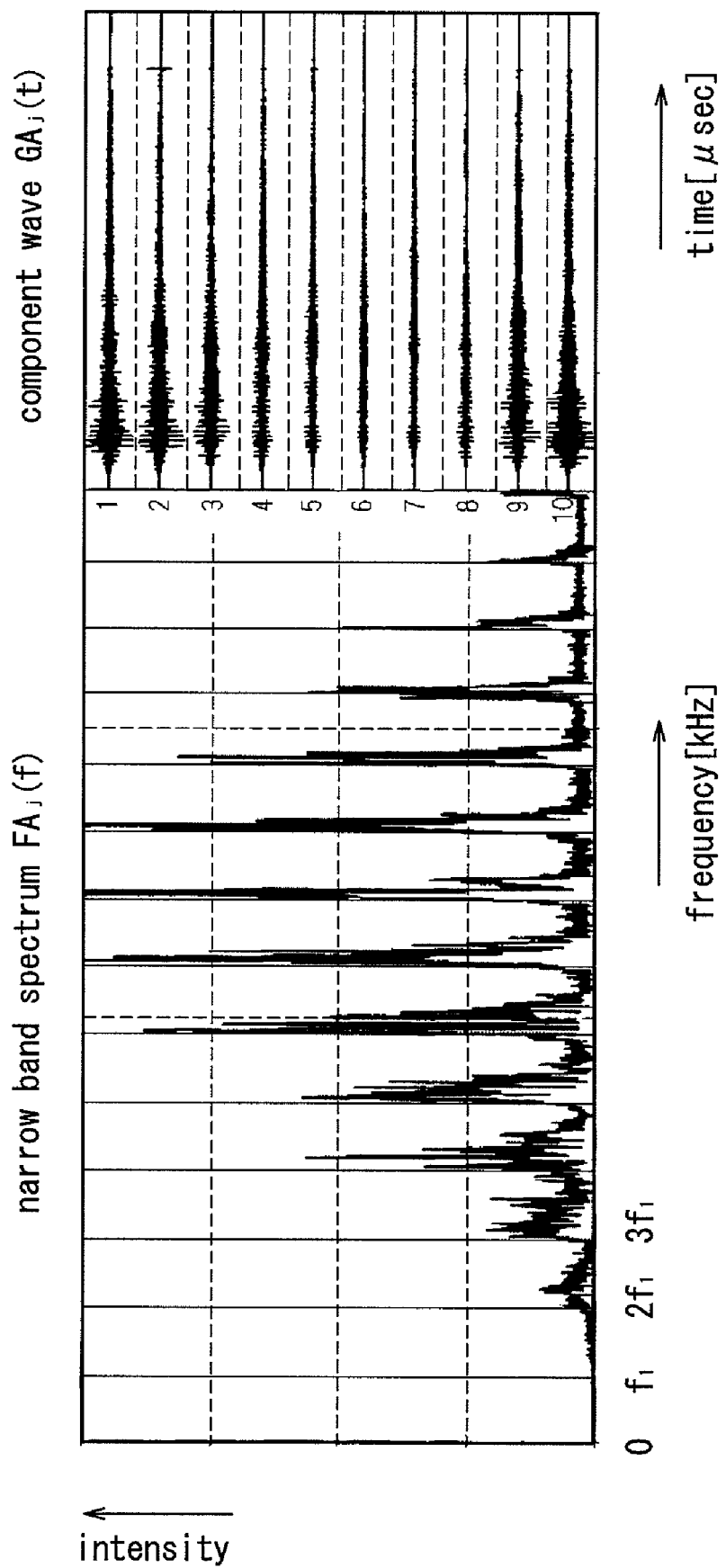
[FIG. 11] A comparative display of a narrowband spectrum and a component wave.
Figure 12:
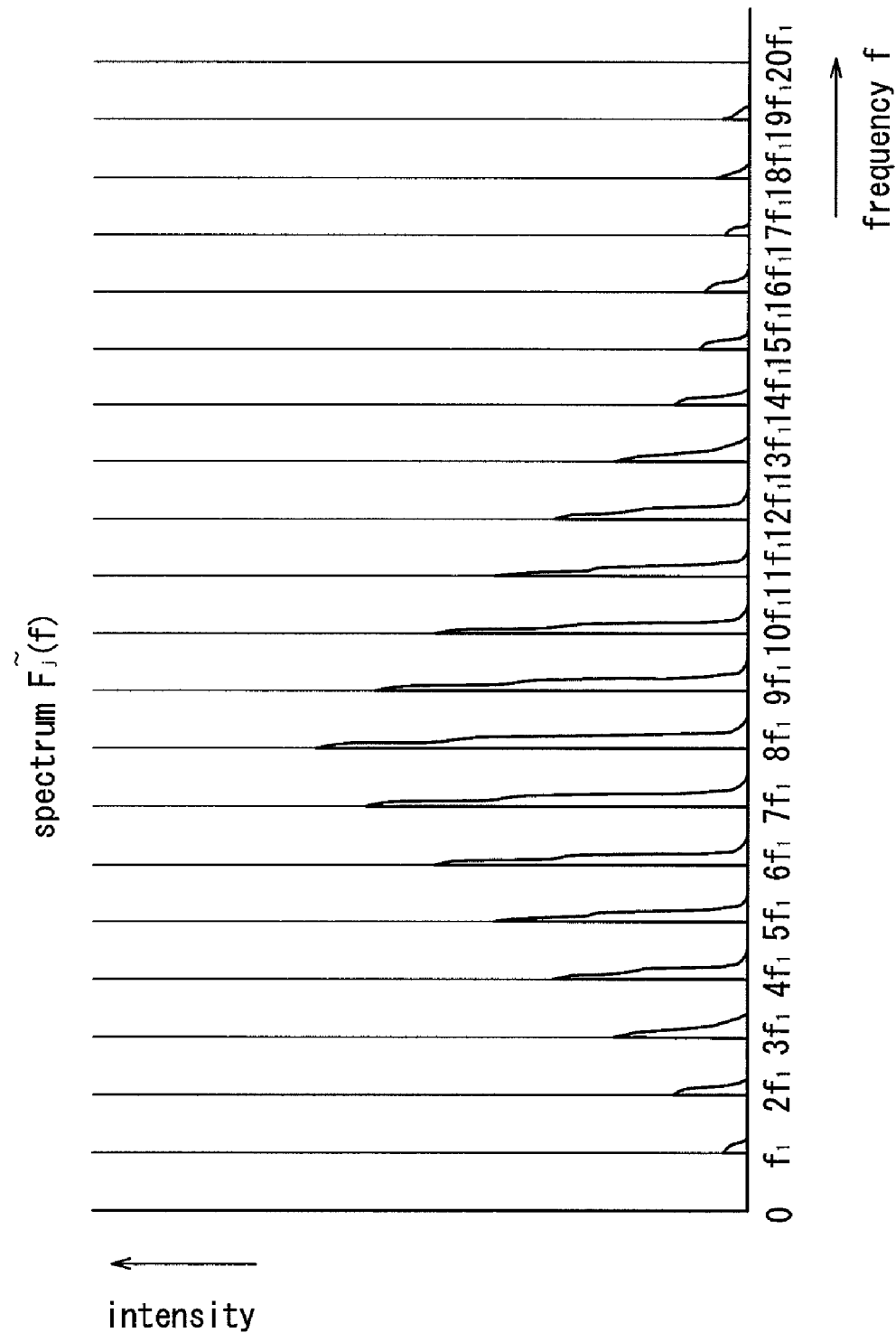
[FIG. 12] A comparative display of a narrow band spectrum.
Figure 13:
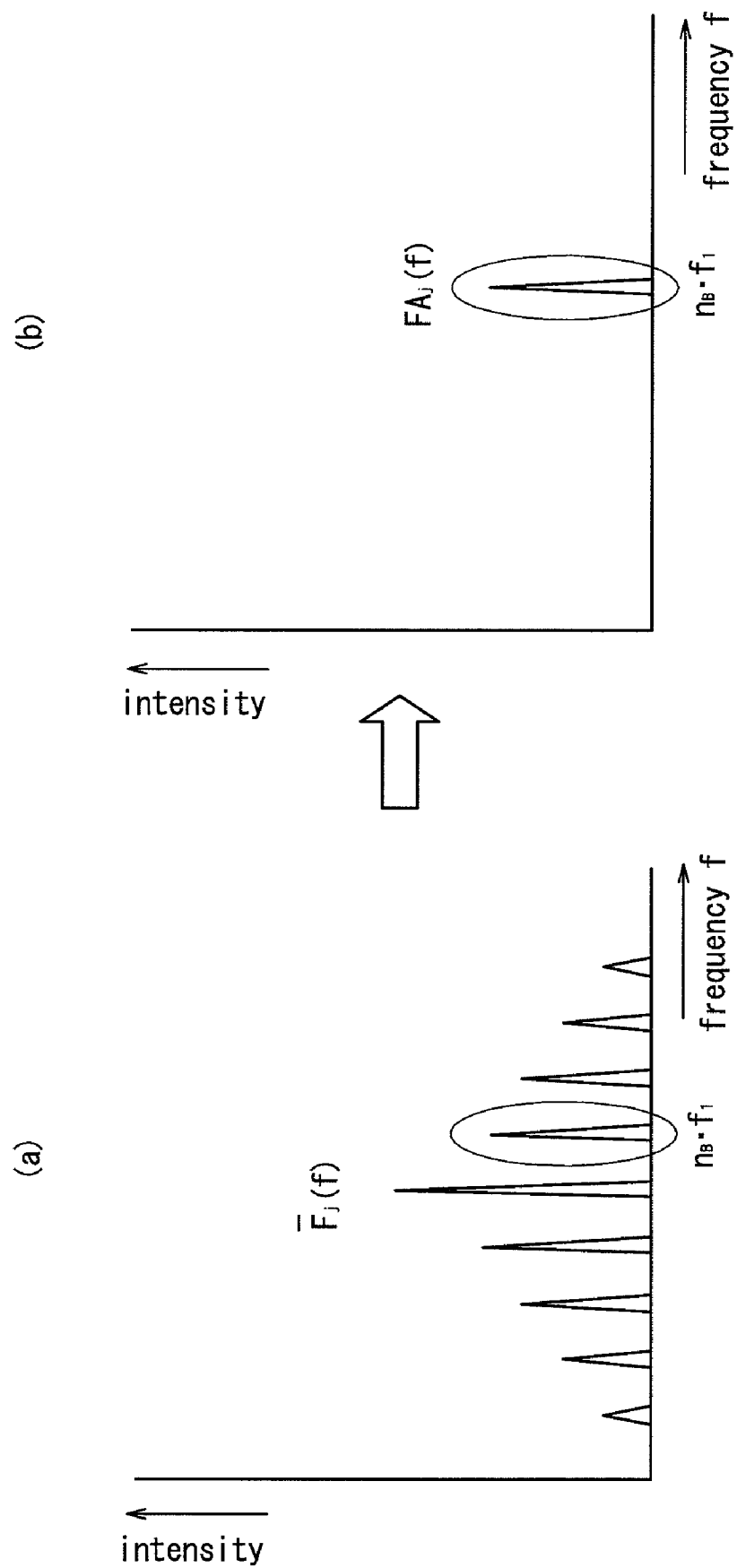
[FIG. 13] A view illustrating sampling-out of a narrow band spectrum.
Figure 14:
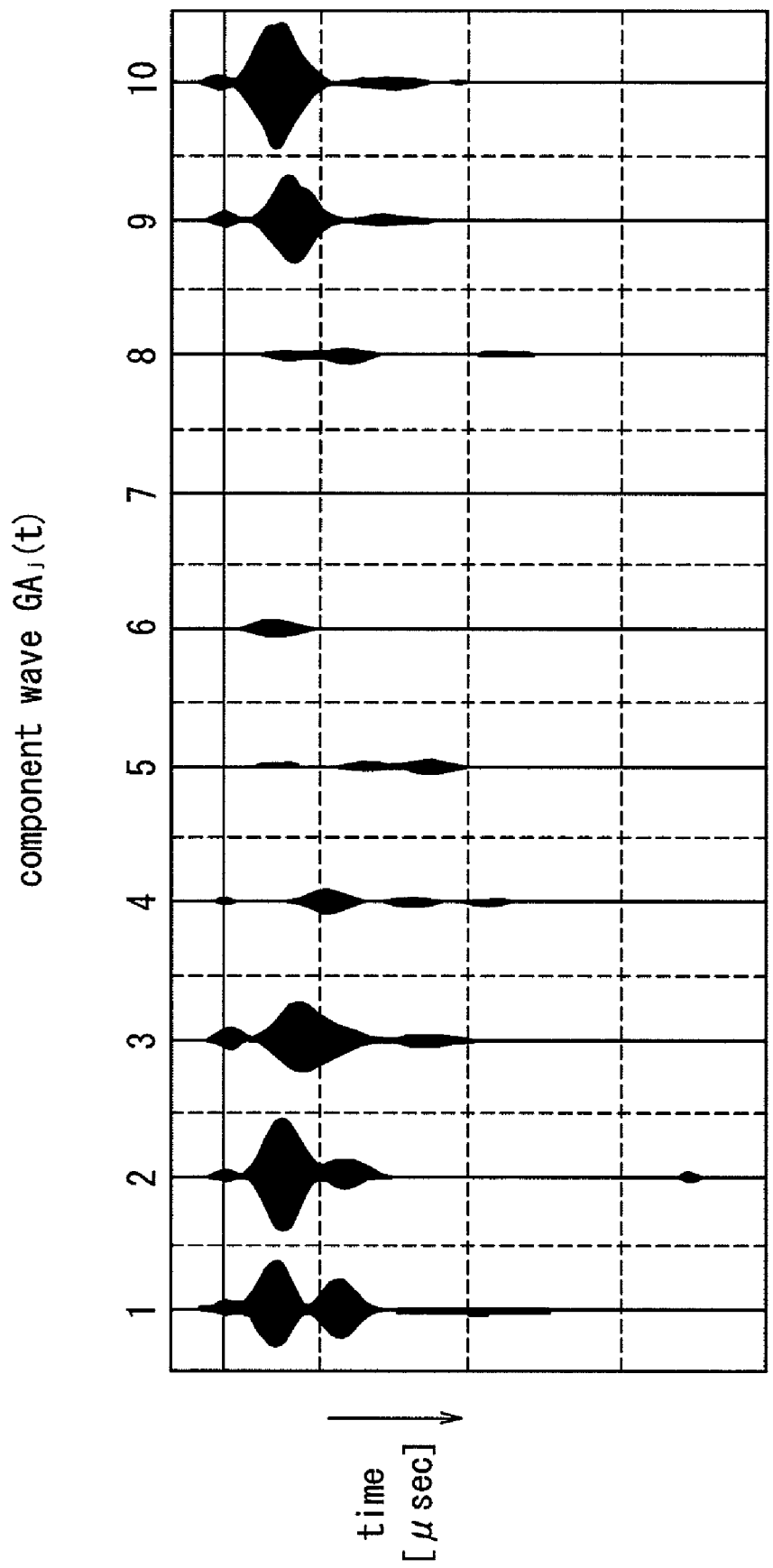
[FIG. 14] A comparative display of a component wave.
Figure 15:
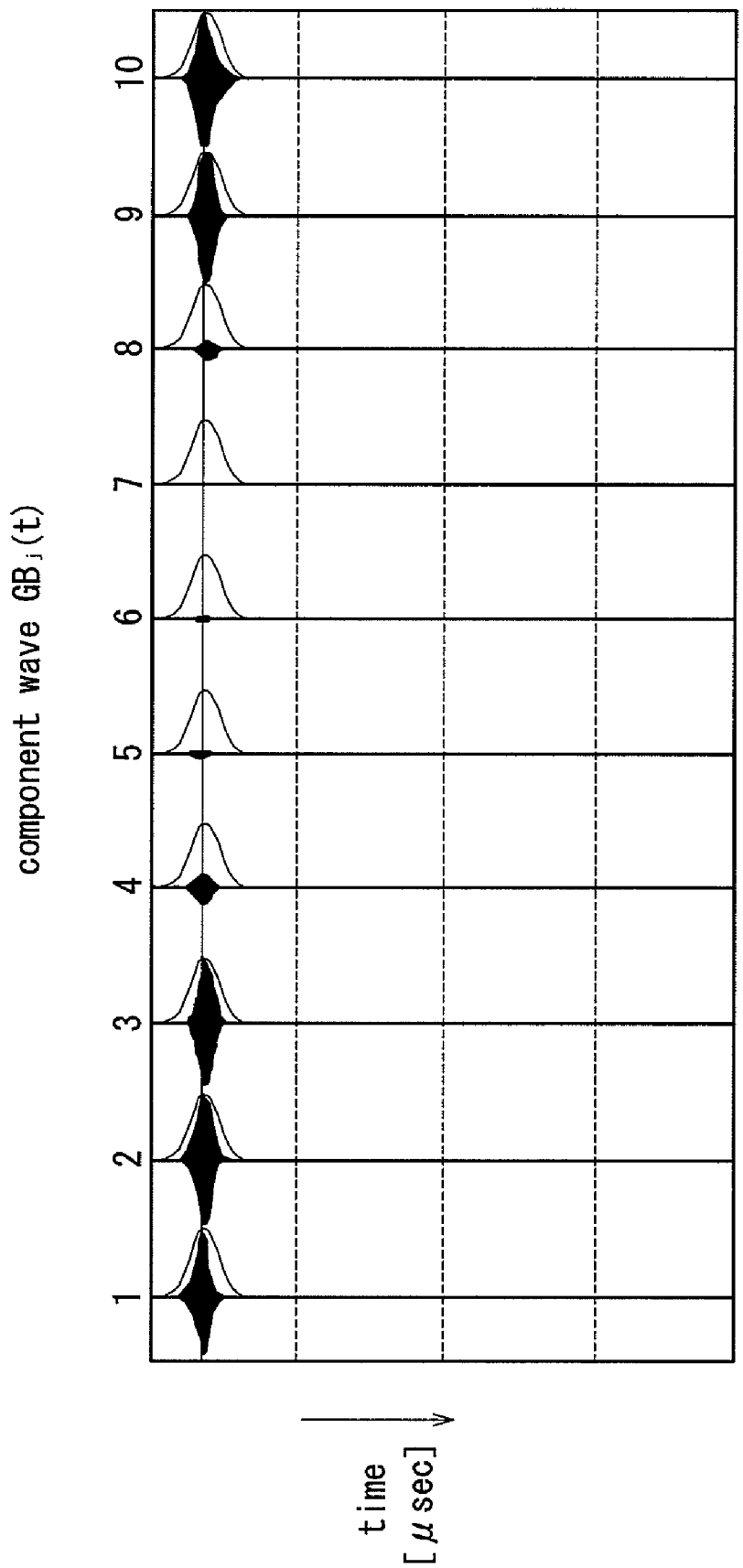
[FIG. 15] A comparative display of a component wave obtained by using a time history filter.
Figure 16:
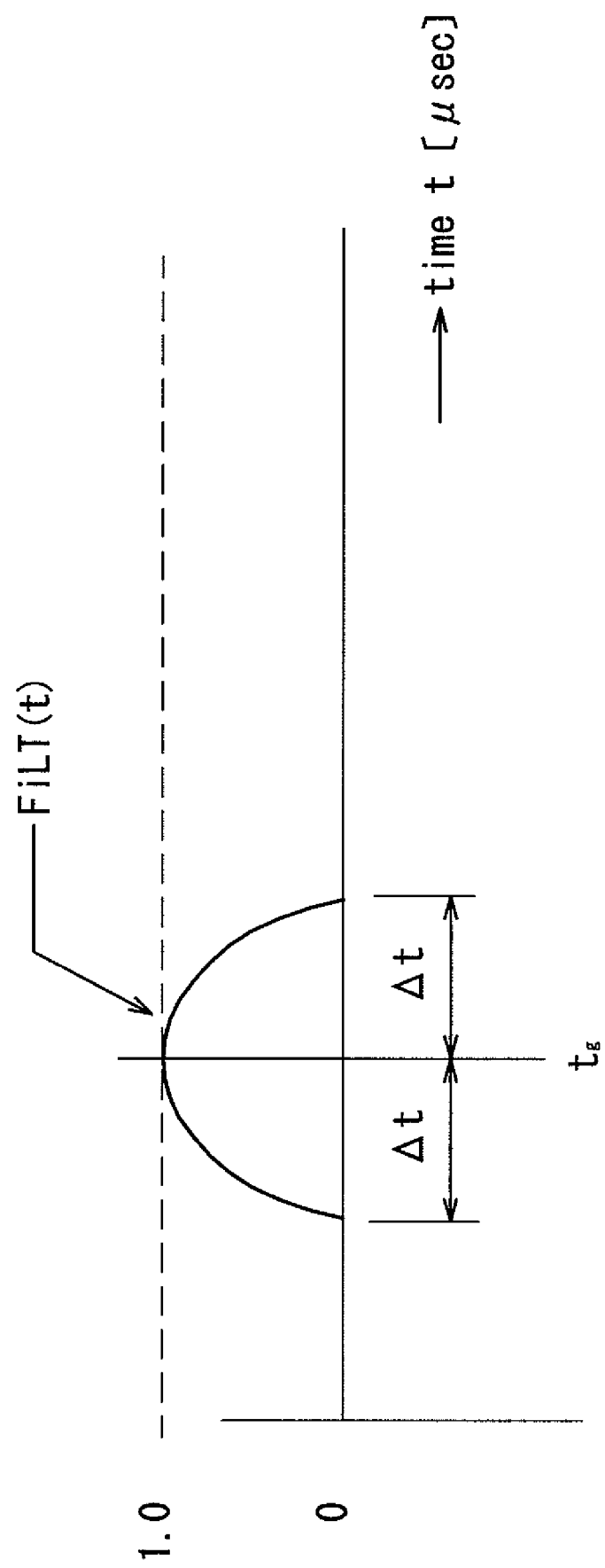
[FIG. 16] A view illustrating a time history filter.
Figure 17:
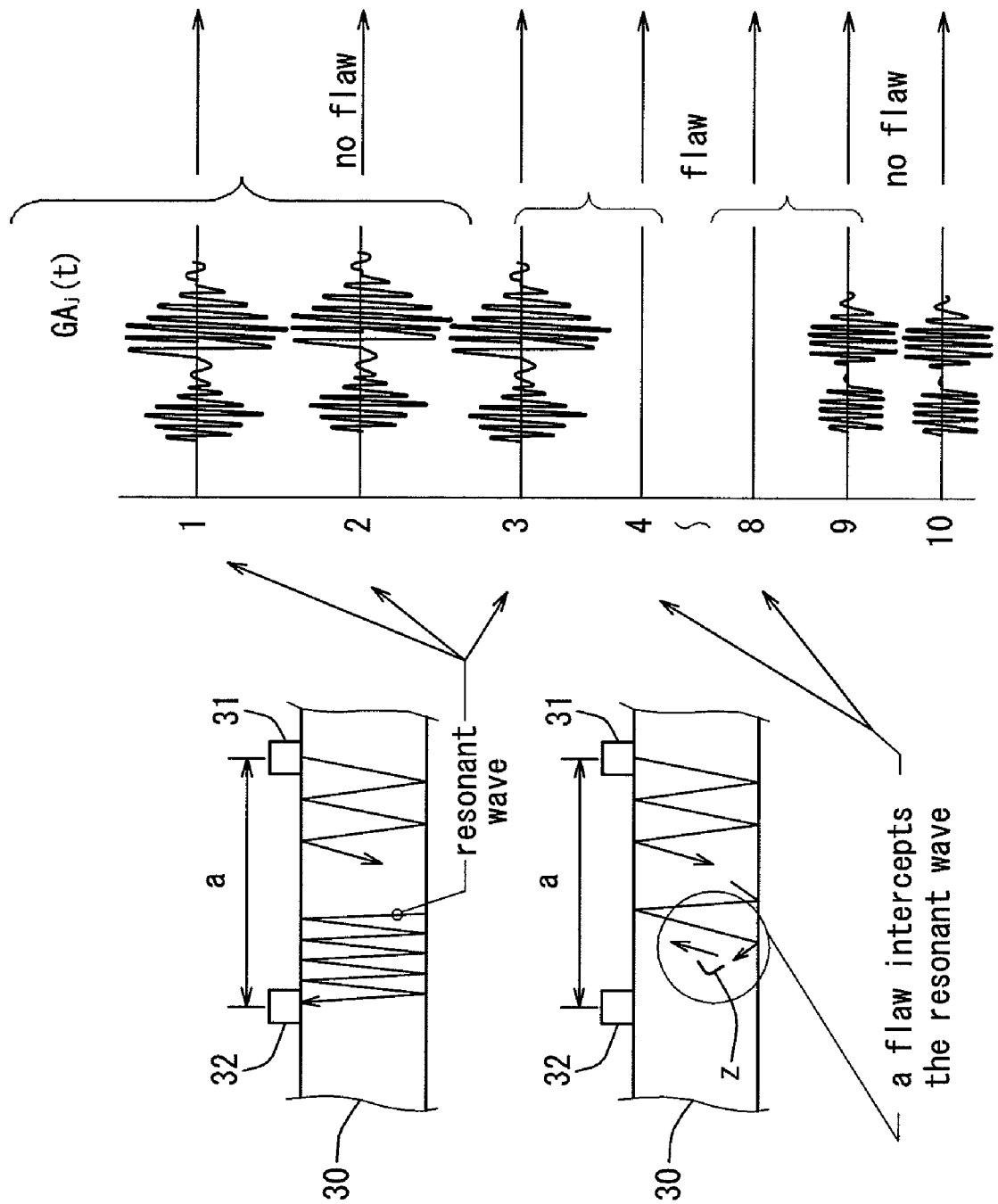
[FIG. 17] A view illustrating the difference in the component wave due to the presence/absence of a flaw.
Figure 18:
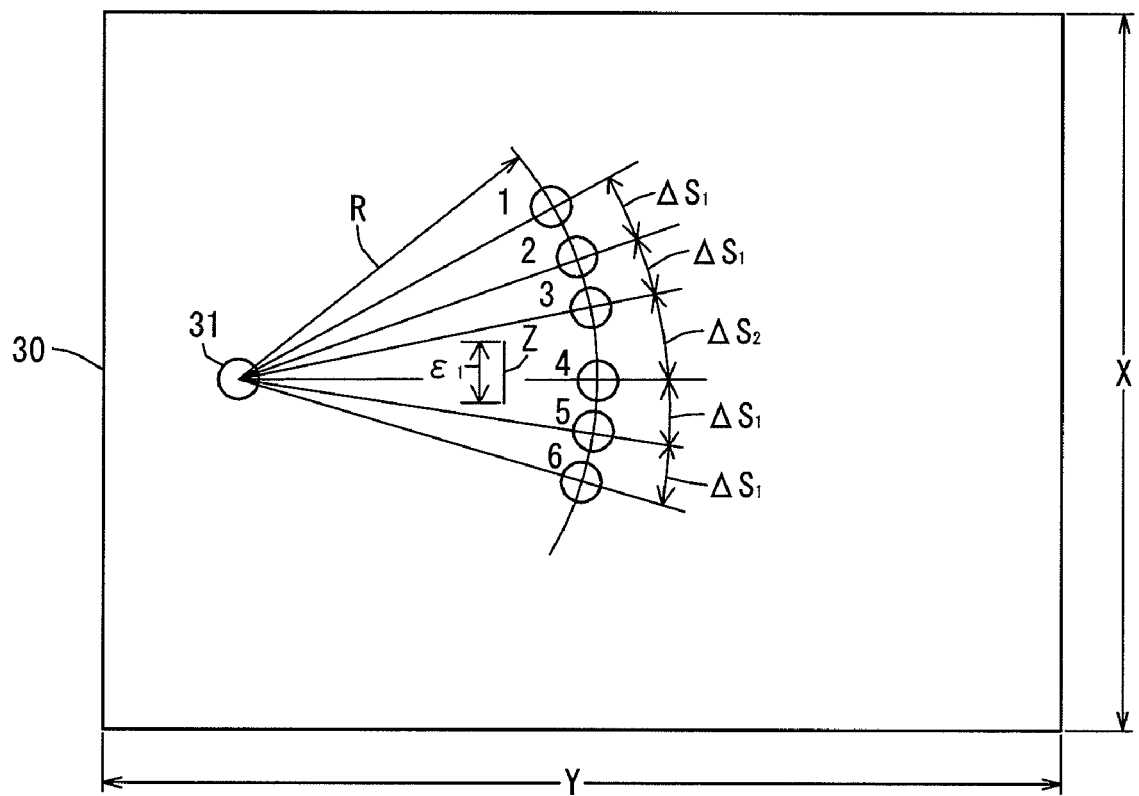
[FIG. 18] A view illustrating another example of moving a probe.
Figure 19:
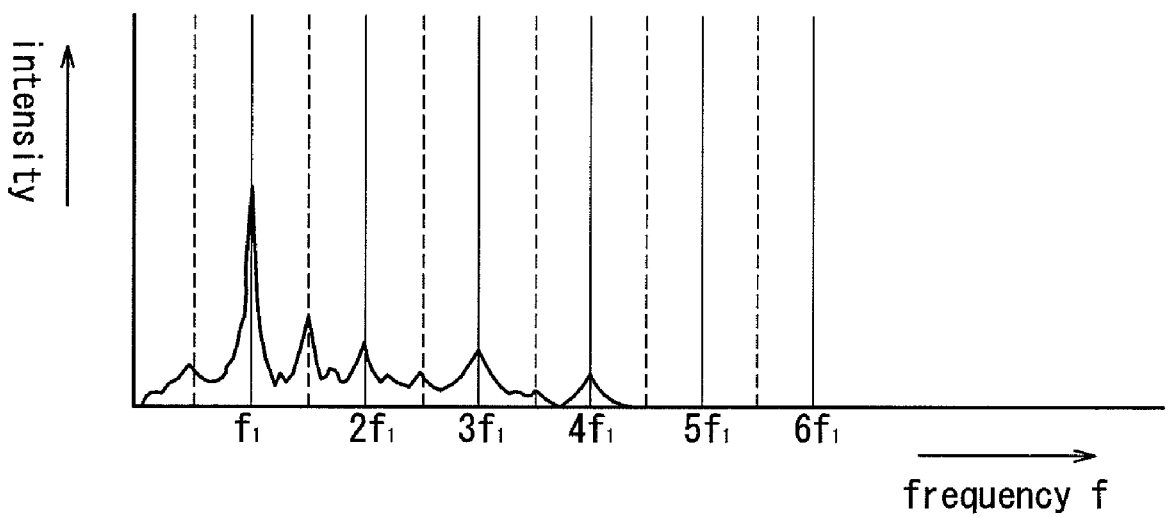
[FIG. 19] A comparative display of a spectrum $F_j(f)$
[FIG. 20] A comparative display of a narrowband spectrum and a component wave.
Figure 20:
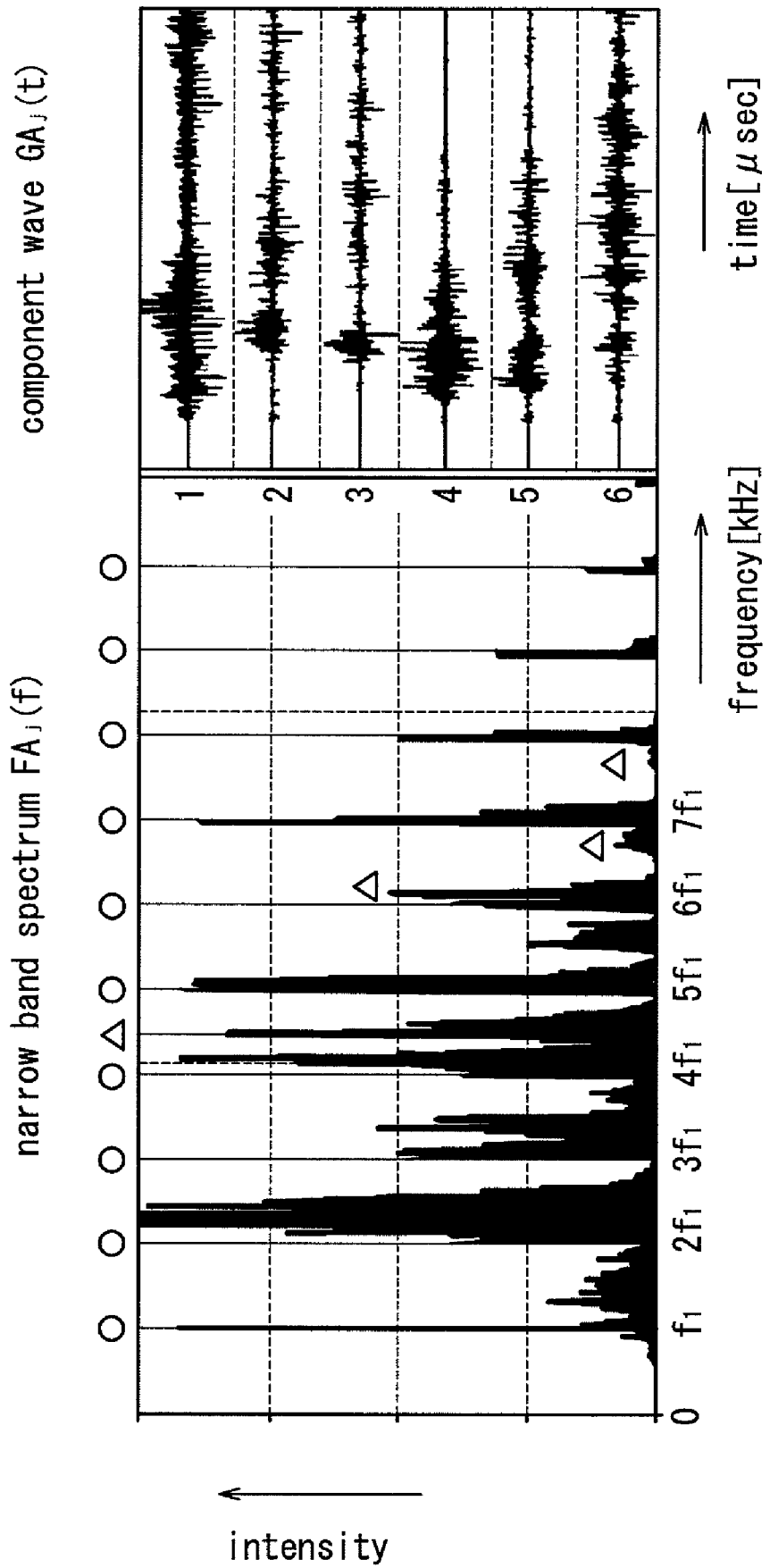
Figure 21:
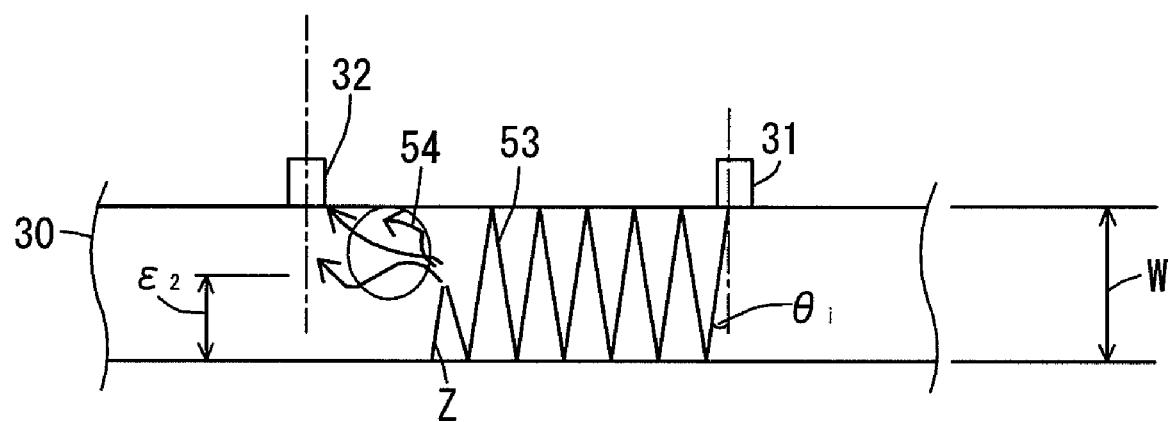
[FIG. 21] A schematic view of ultrasonic wave propagation.
Figure 22:
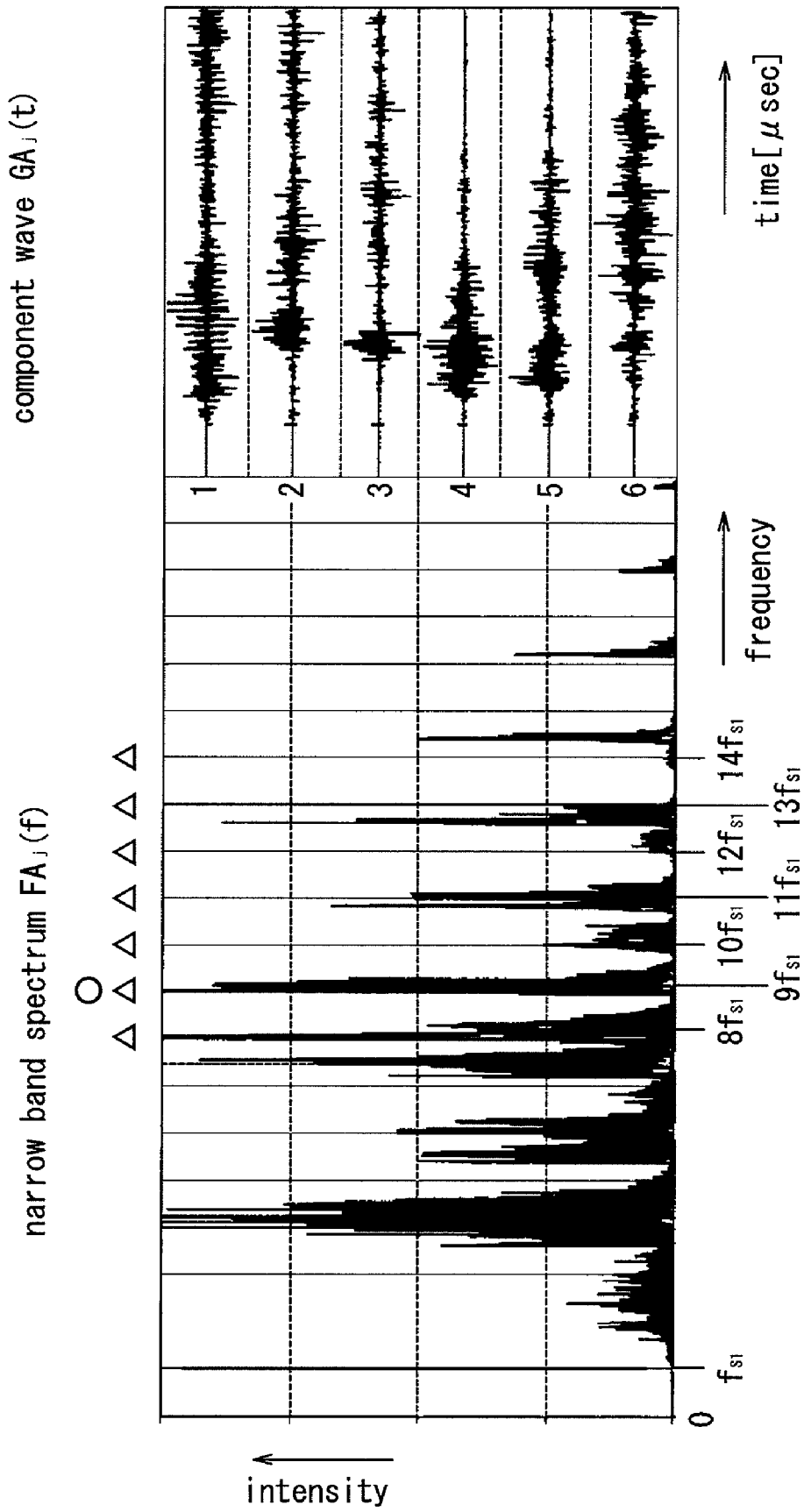
[FIG. 22] A comparative display of a narrowband spectrum and a component wave.
Figure 23:
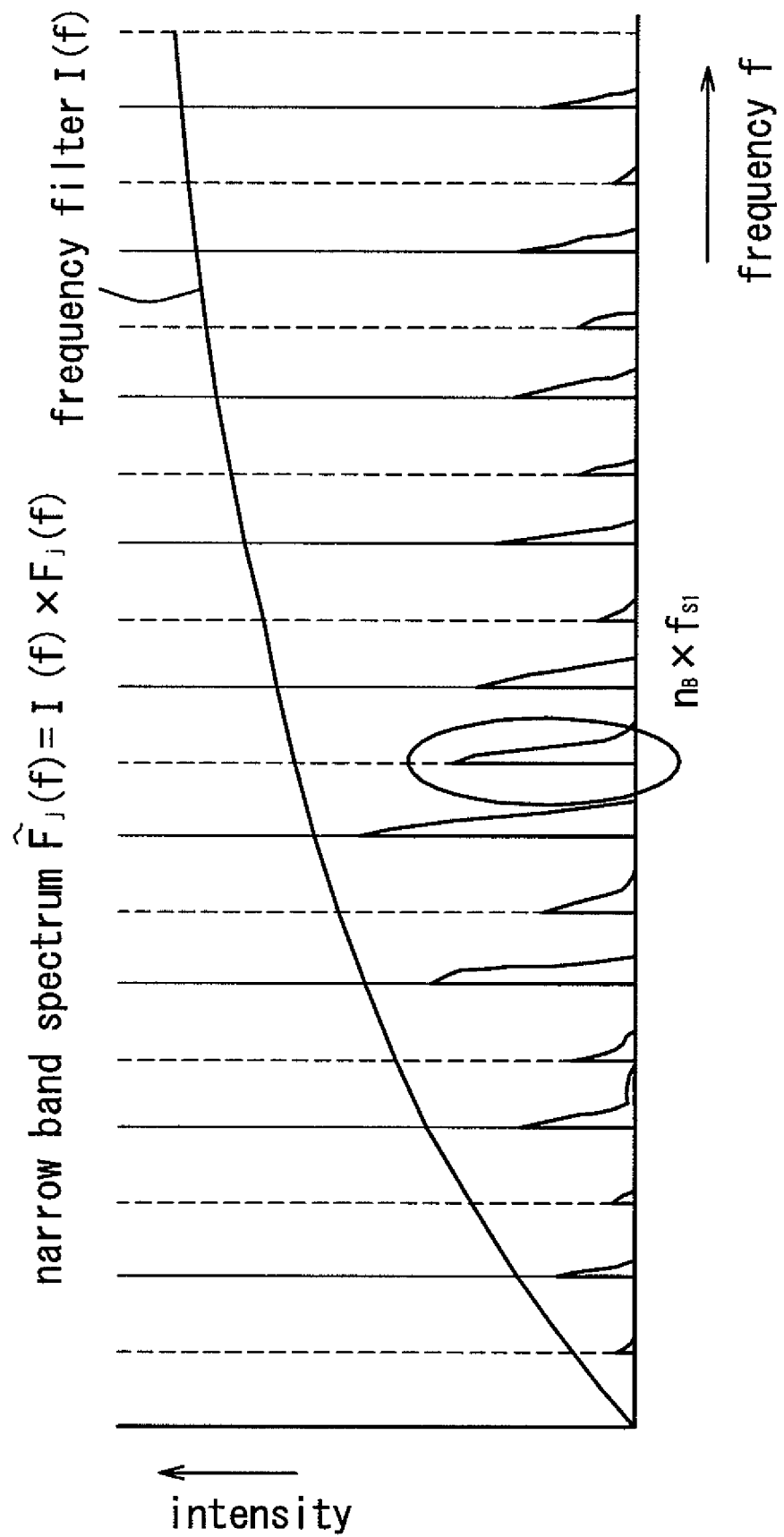
[FIG. 23] A comparative display of a narrow band spectrum.
Figure 24:
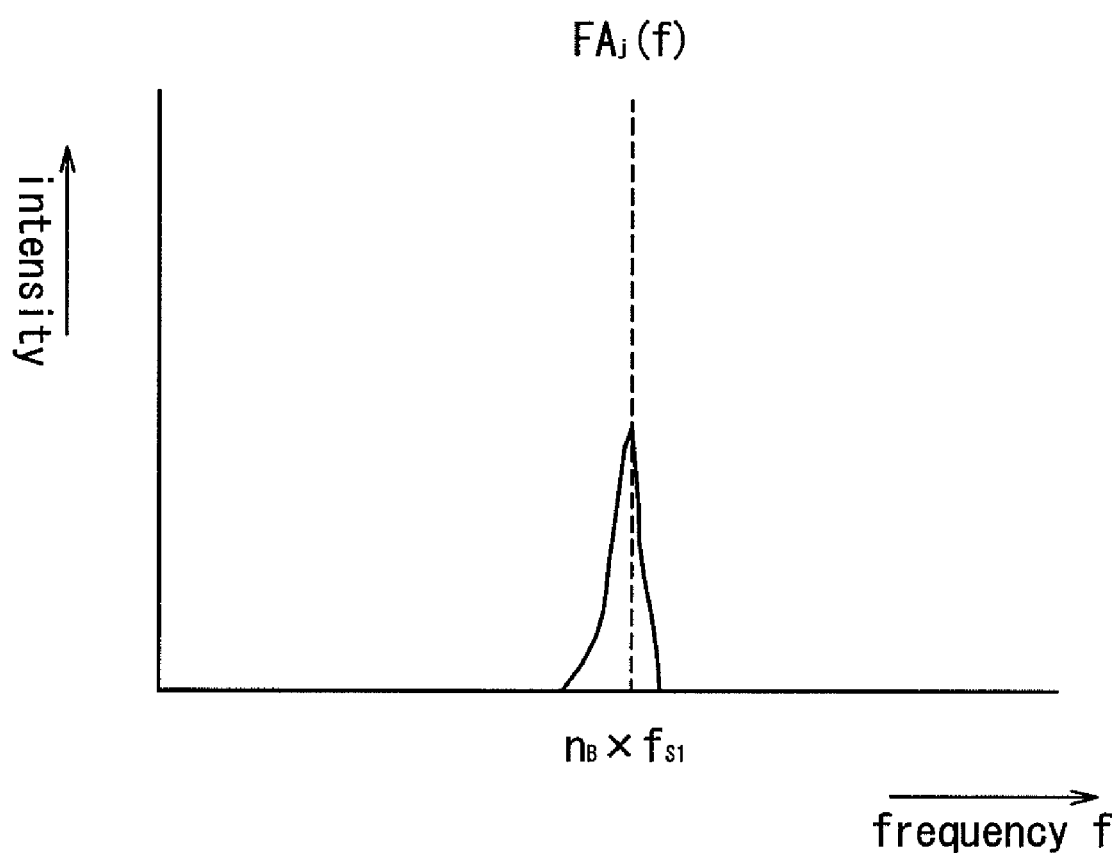
[FIG. 24] A view illustrating a sampled out narrow band spectrum.
Figure 25:
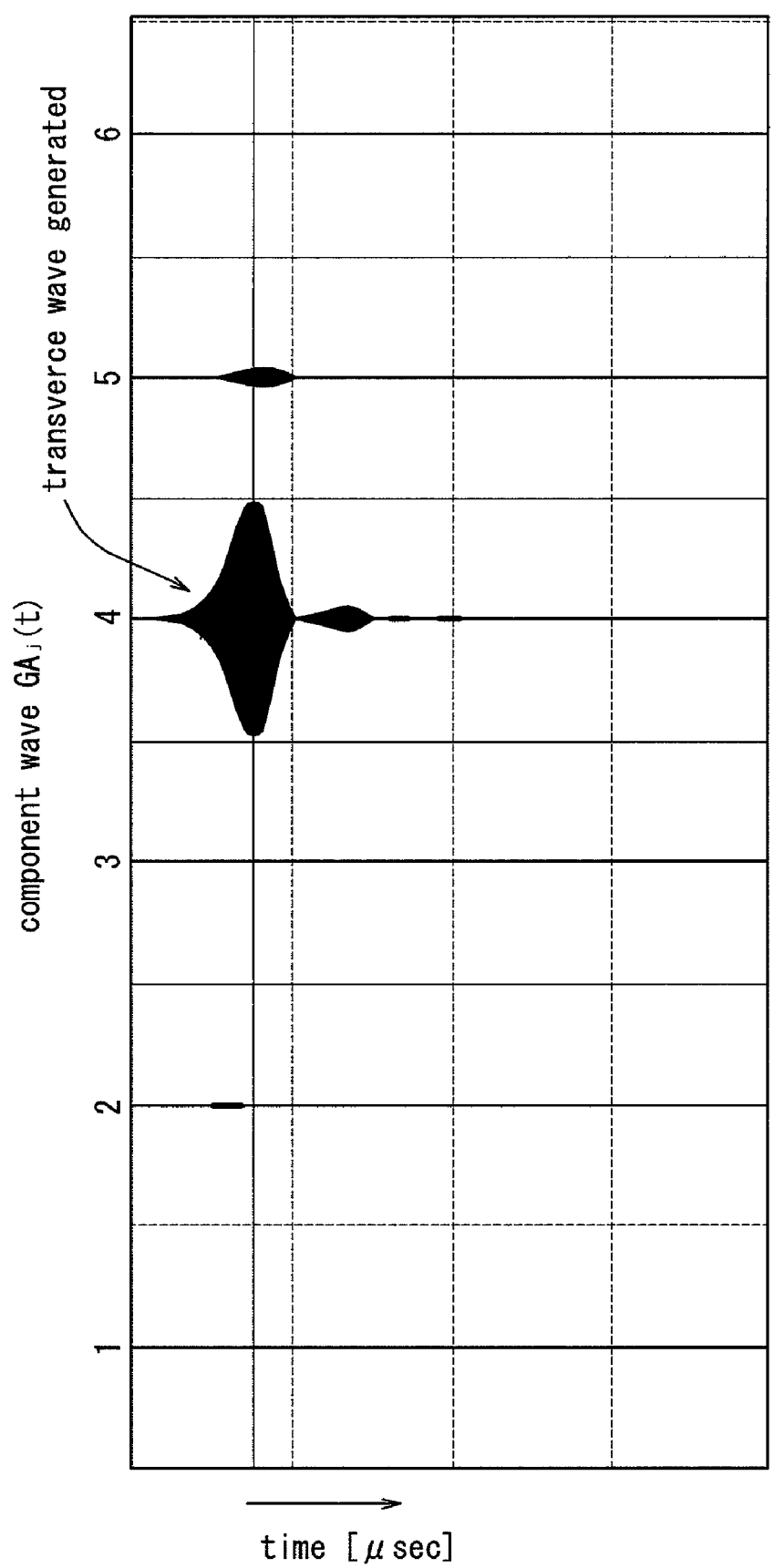
[FIG. 25] A comparative display of a component wave.
Figure 26:
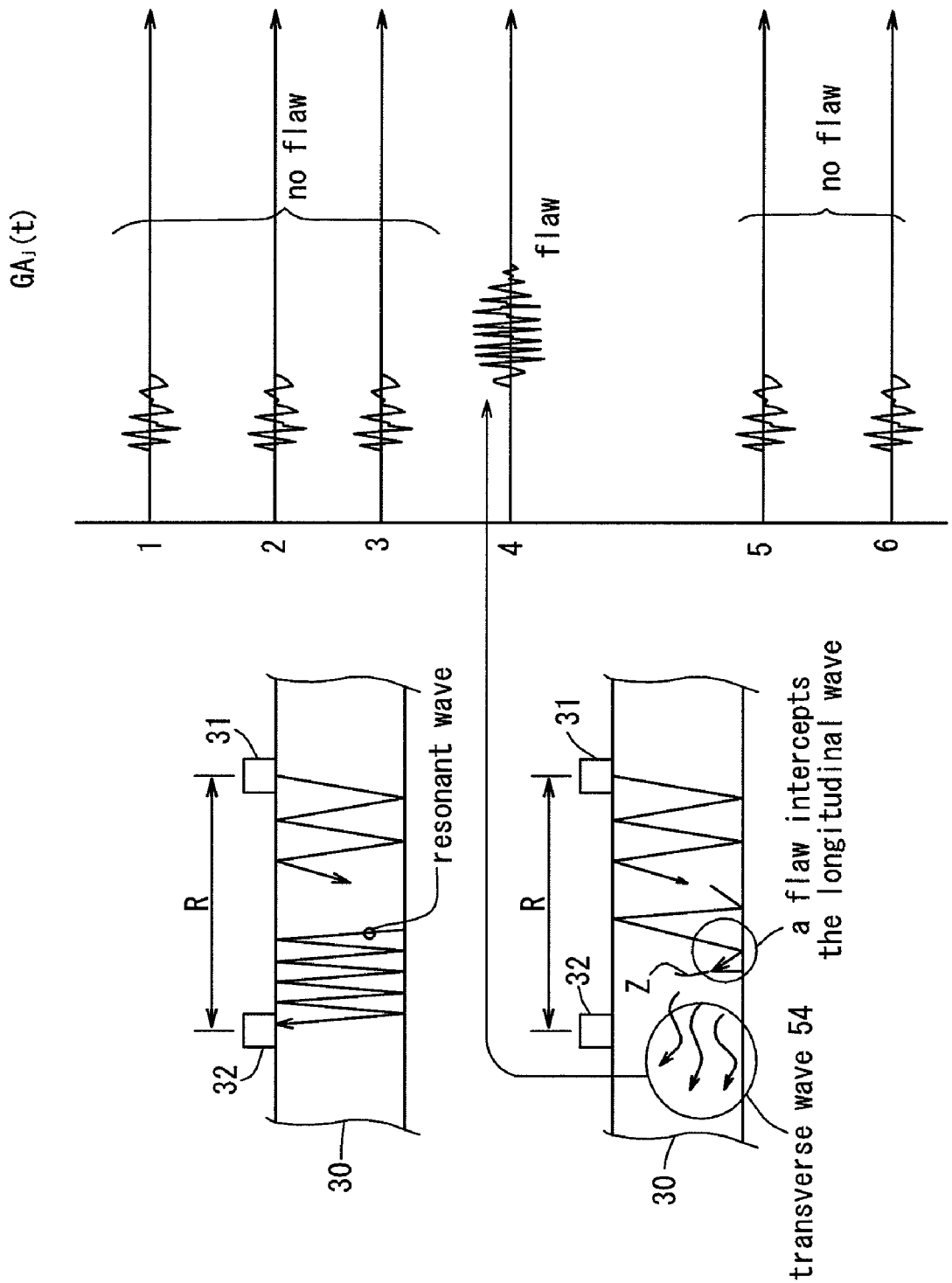
[FIG. 26] A view illustrating the difference in the component wave due to the presence/absence of a flaw.
Figure 27:
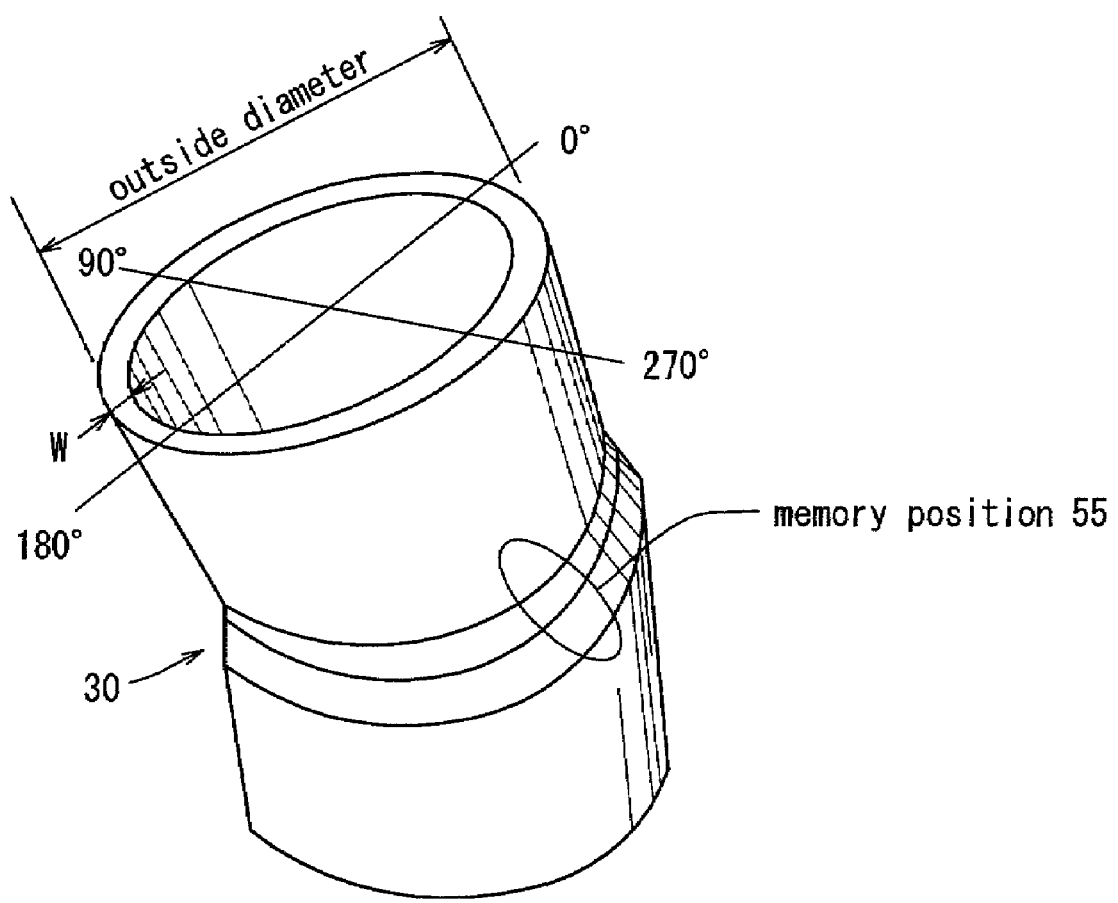
[FIG. 27] A perspective view illustrating another example of the probe.
Figure 28:
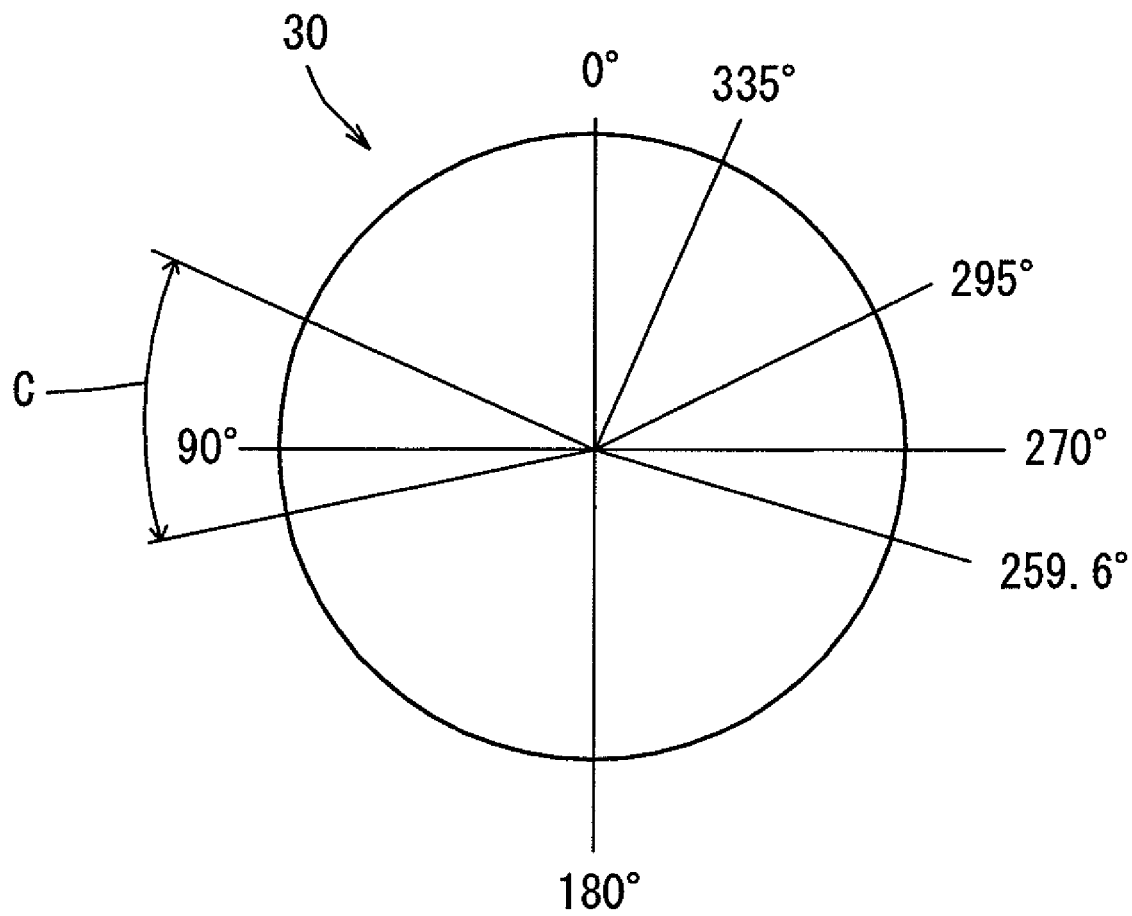
[FIG. 28] A view illustrating a measurement range.
Figure 29:
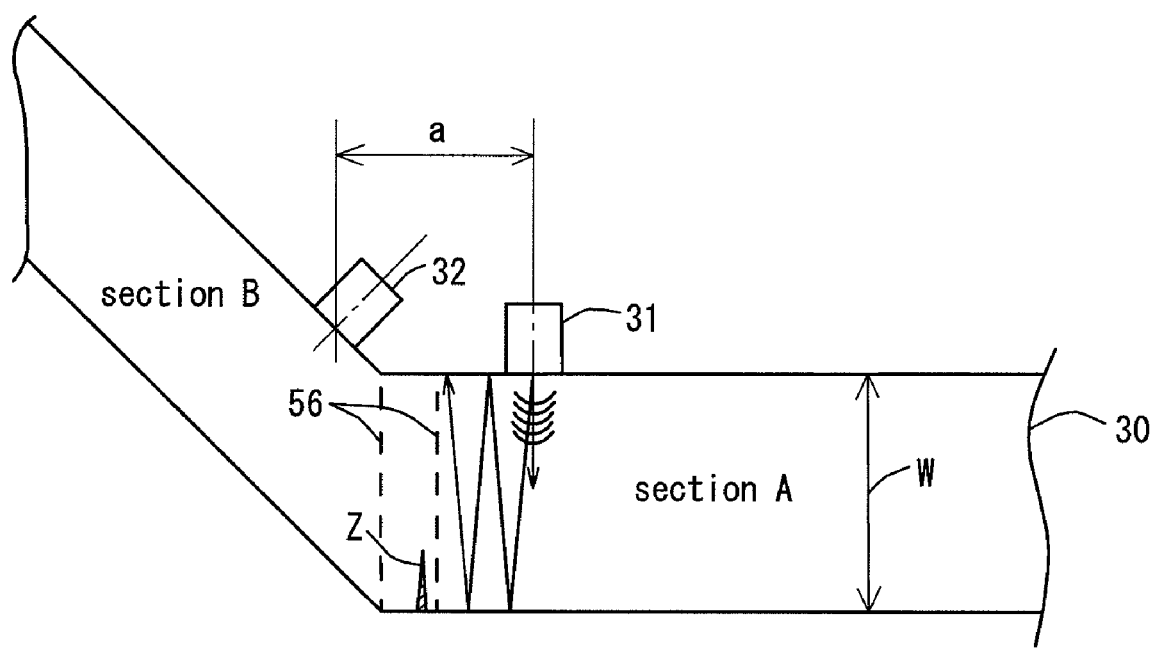
[FIG. 29] A schematic view of ultrasonic wave propagation.
Figure 30:
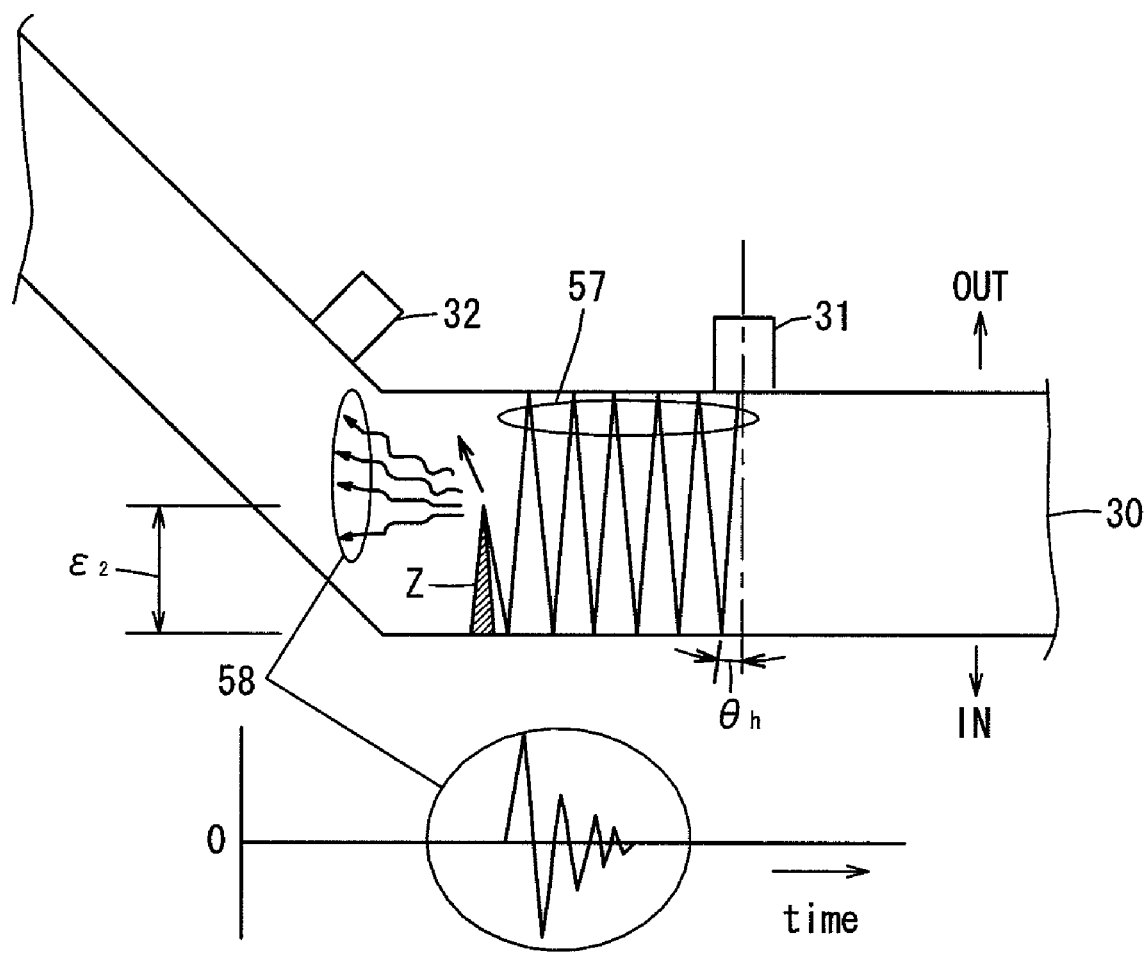
[FIG. 30] A view illustrating the generation characteristics of longitudinal and transverse waves.
Figure 32:
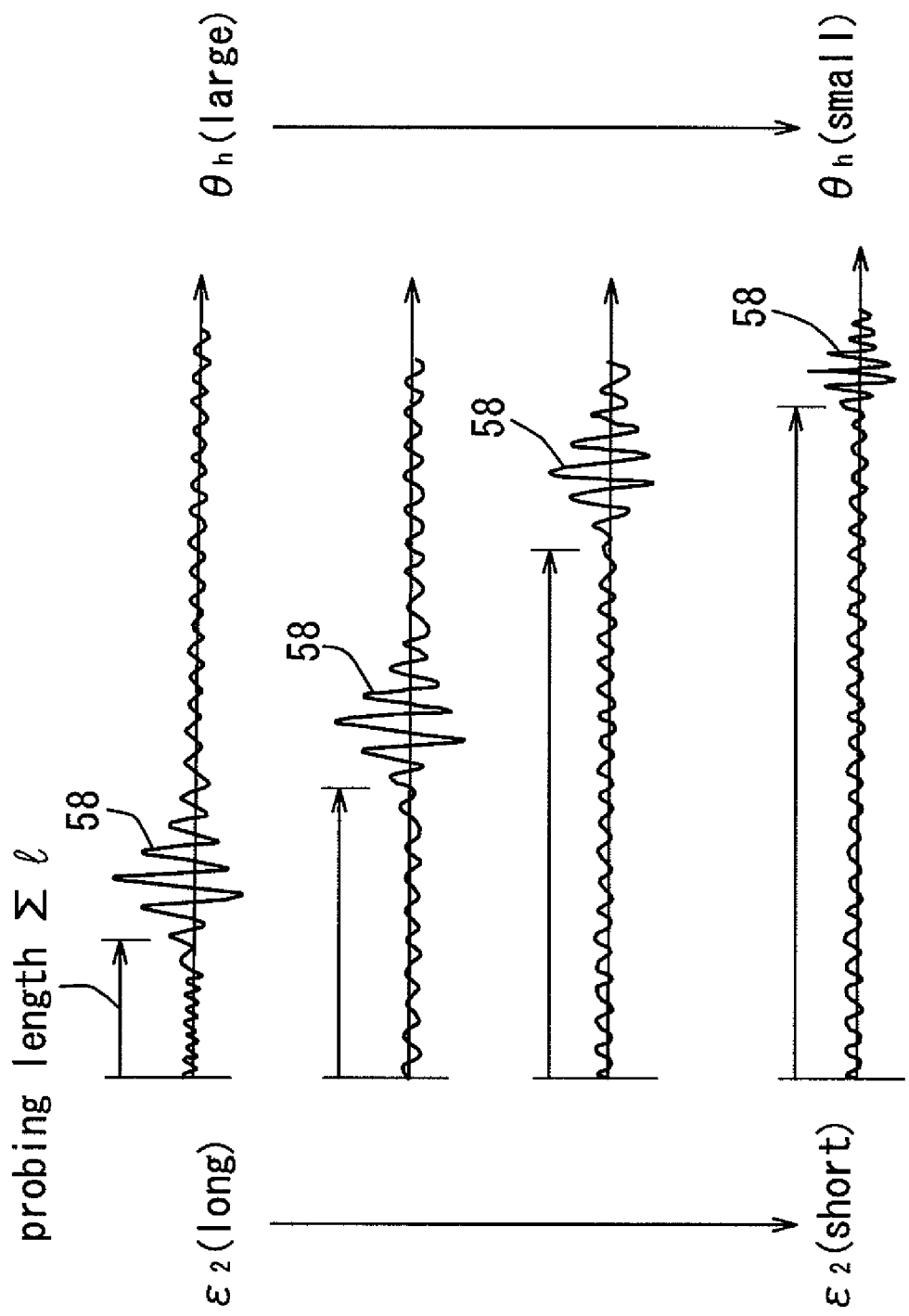
[FIG. 32] A view illustrating the generation of a transverse wave changing in accordance with the flaw height.
Figure 33:
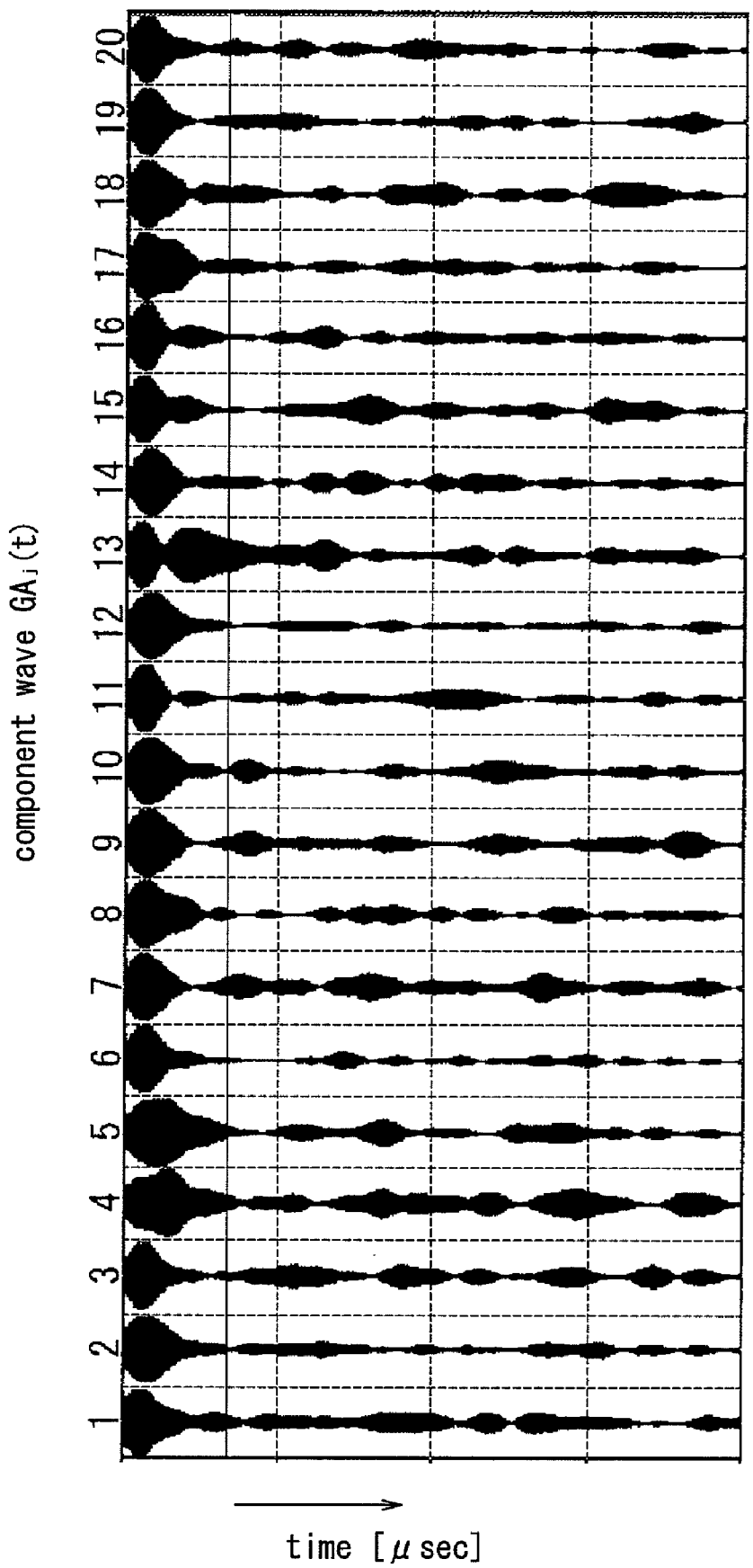
[FIG. 33] A comparative display of a component wave illustrating a state where analysis is impossible due to the presence of a scattering phenomenon.
Figure 34:
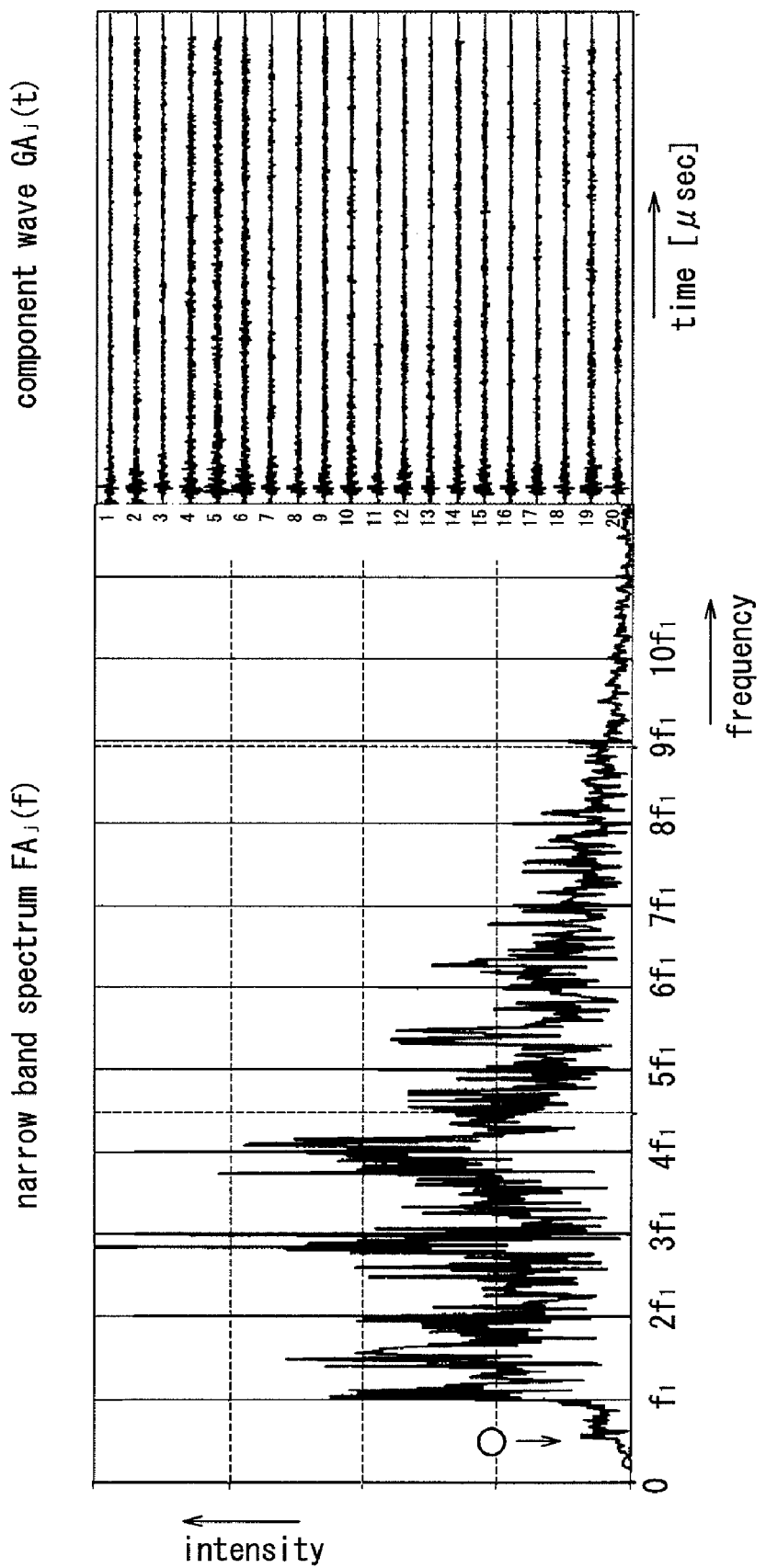
[FIG. 34] A comparative display of a narrowband spectrum and a component wave.
Figure 35:
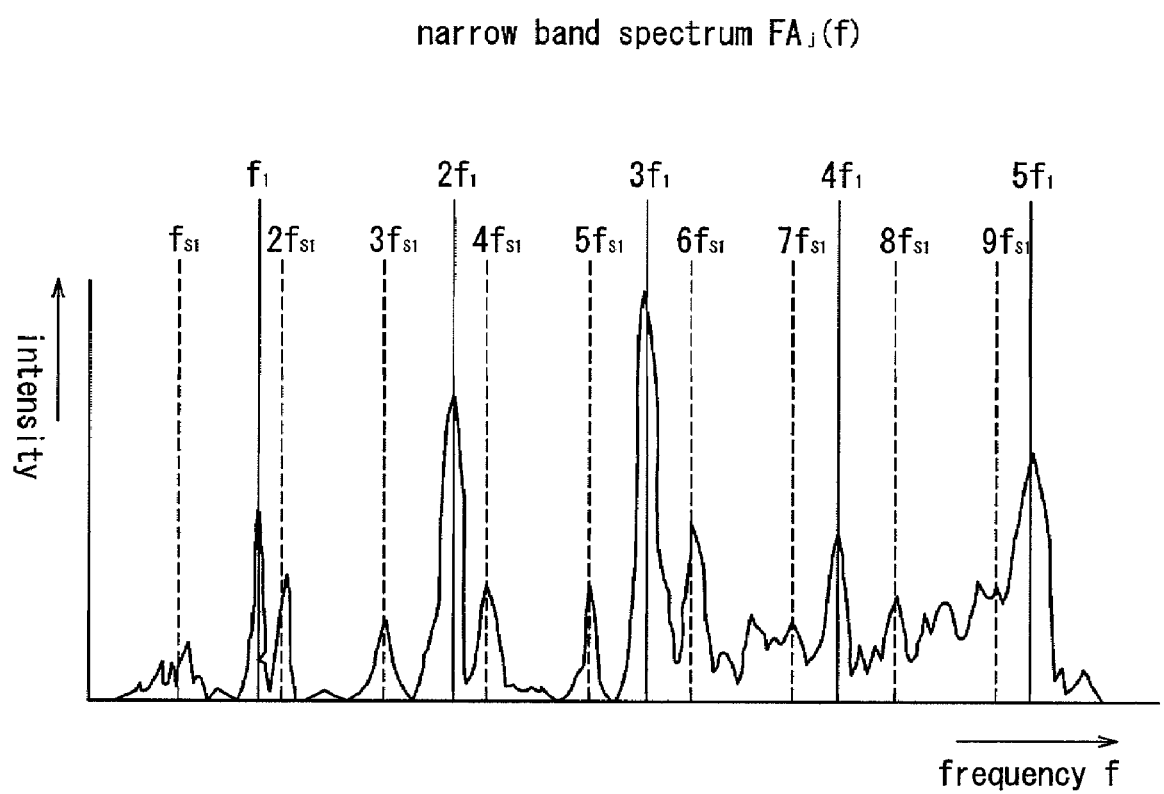
[FIG. 35] A schematic view of the comparative display of FIG. 34.
Figure 36:
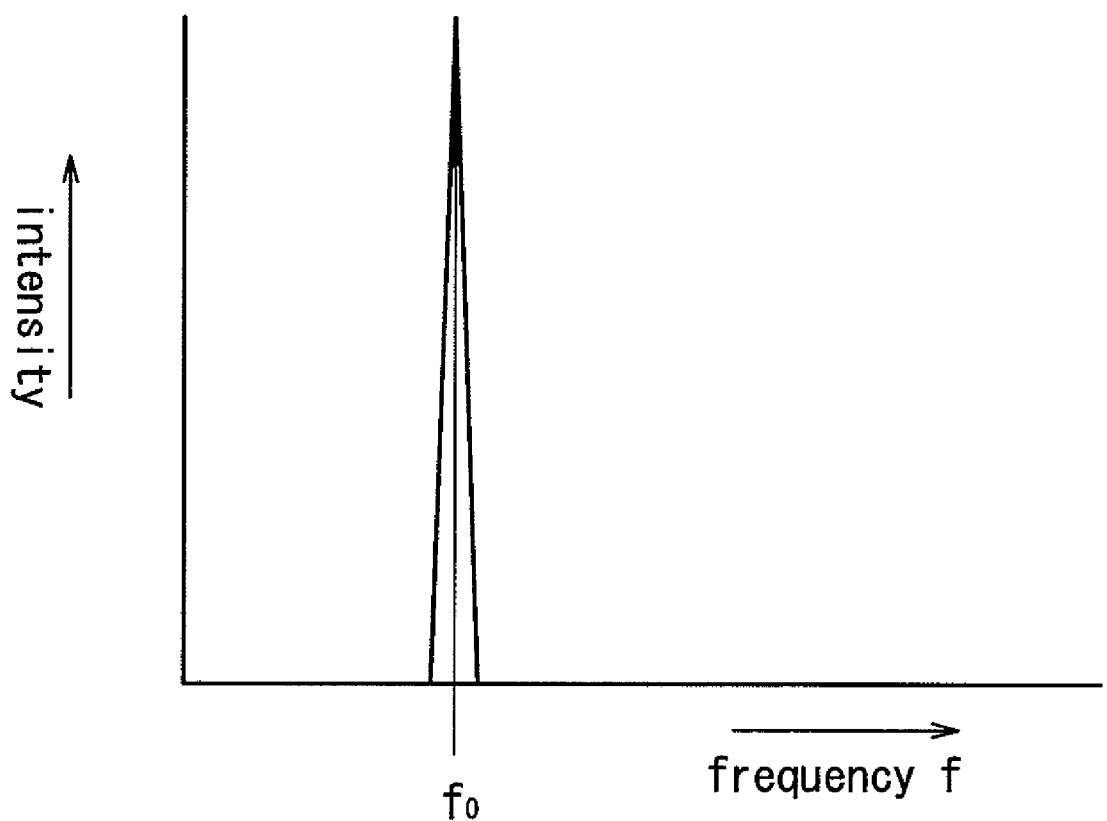
[FIG. 36] A view illustrating a sampled out narrow band spectrum.
Figure 37:
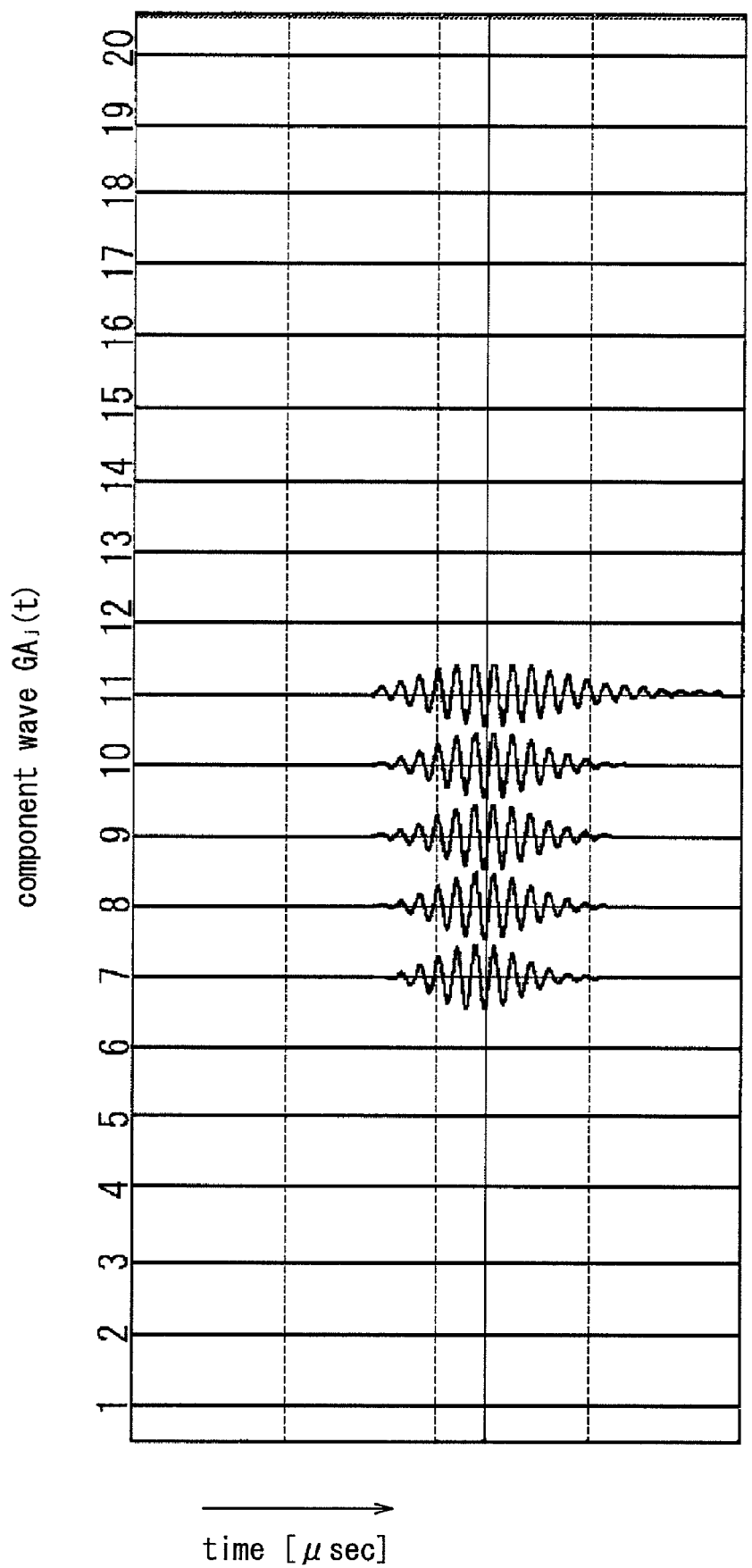
[FIG. 37] A comparative display of a component wave.
Figure 38:
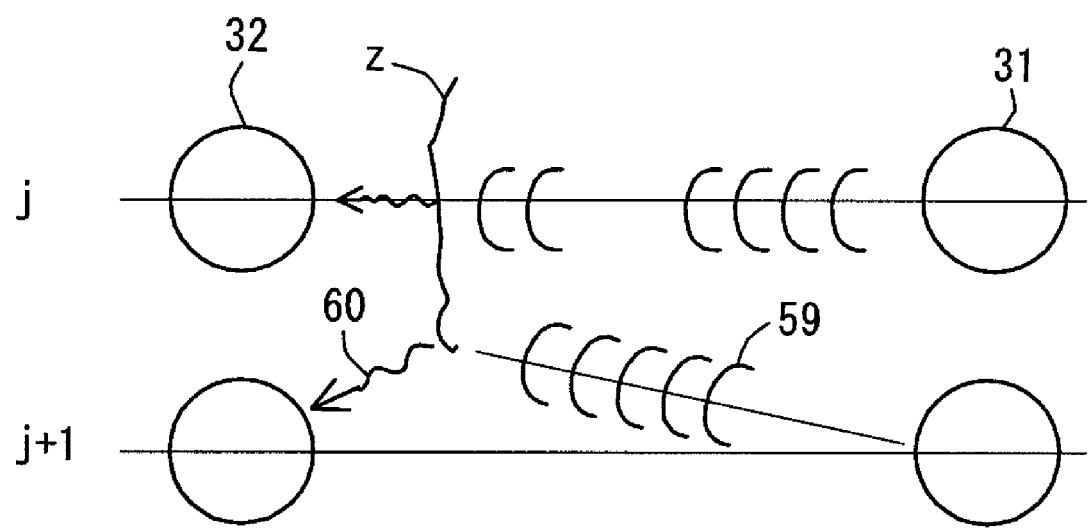
[FIG. 38] A schematic view of ultrasonic wave propagation under a low frequency condition.
Figure 39:
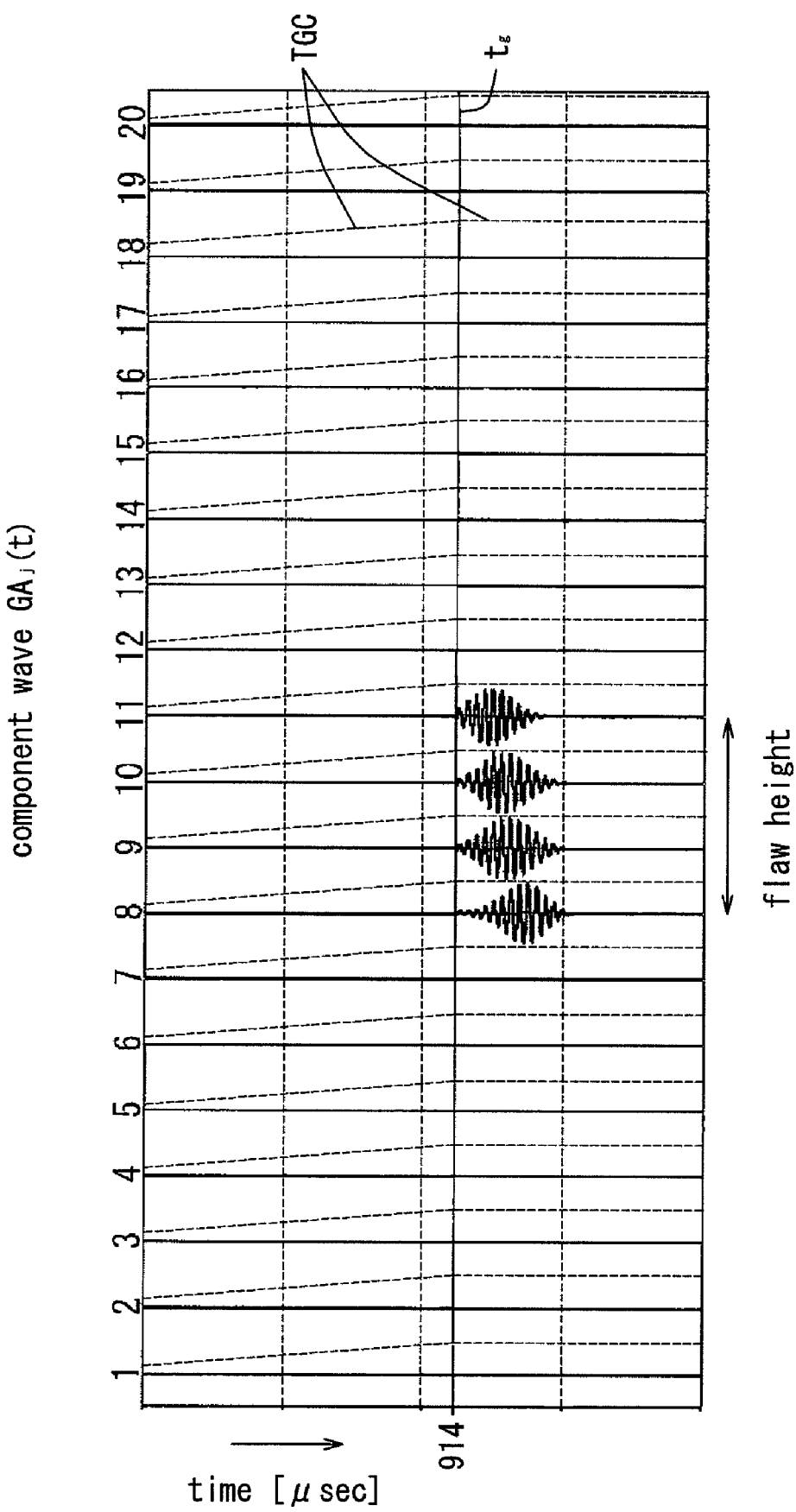
[FIG. 39] A comparative display of a component wave.
Figure 40:
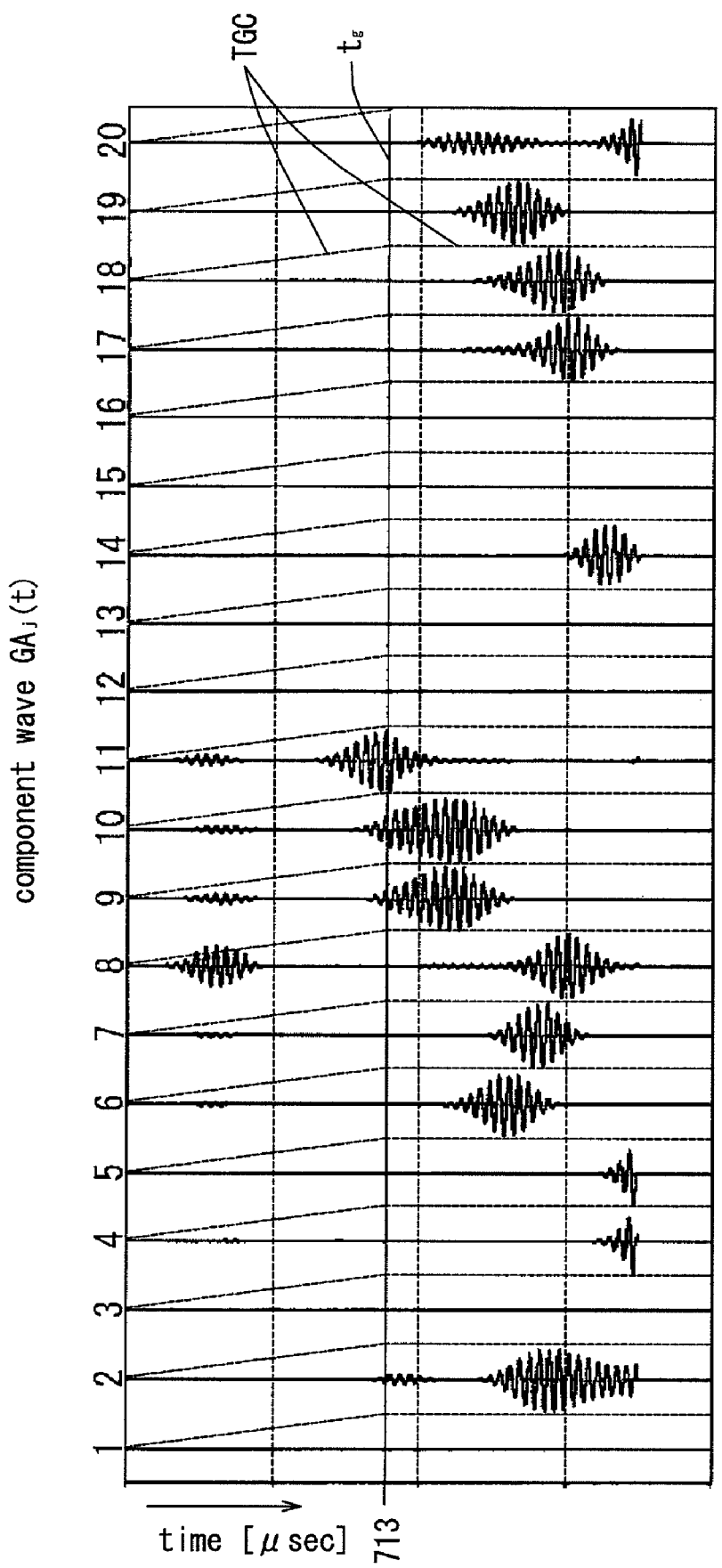
[FIG. 40] A comparative display of a component wave by an inappropriate $f_0$ value.
Figure 41:
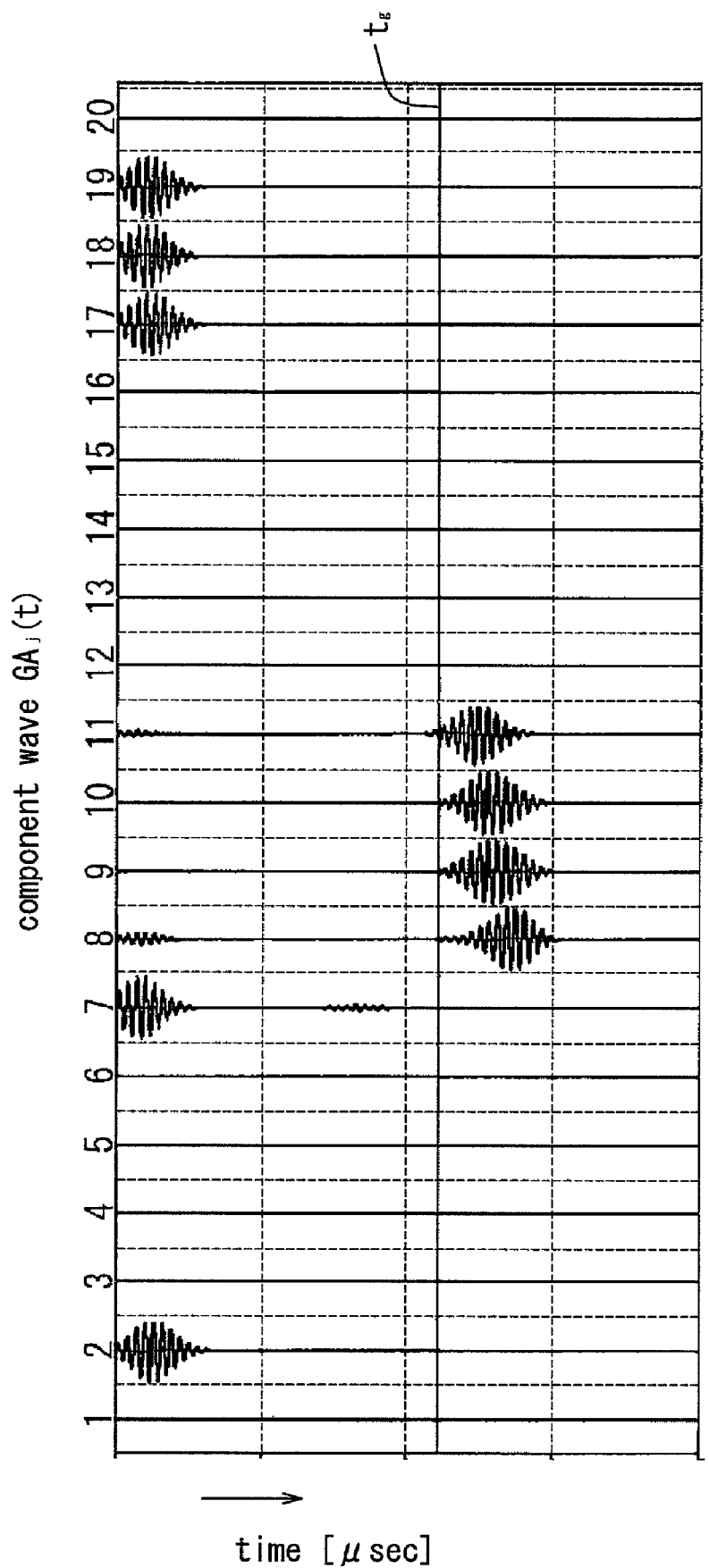
[FIG. 41] A comparative display of a component wave obtained when TGC processing is not performed.
Figure 42:
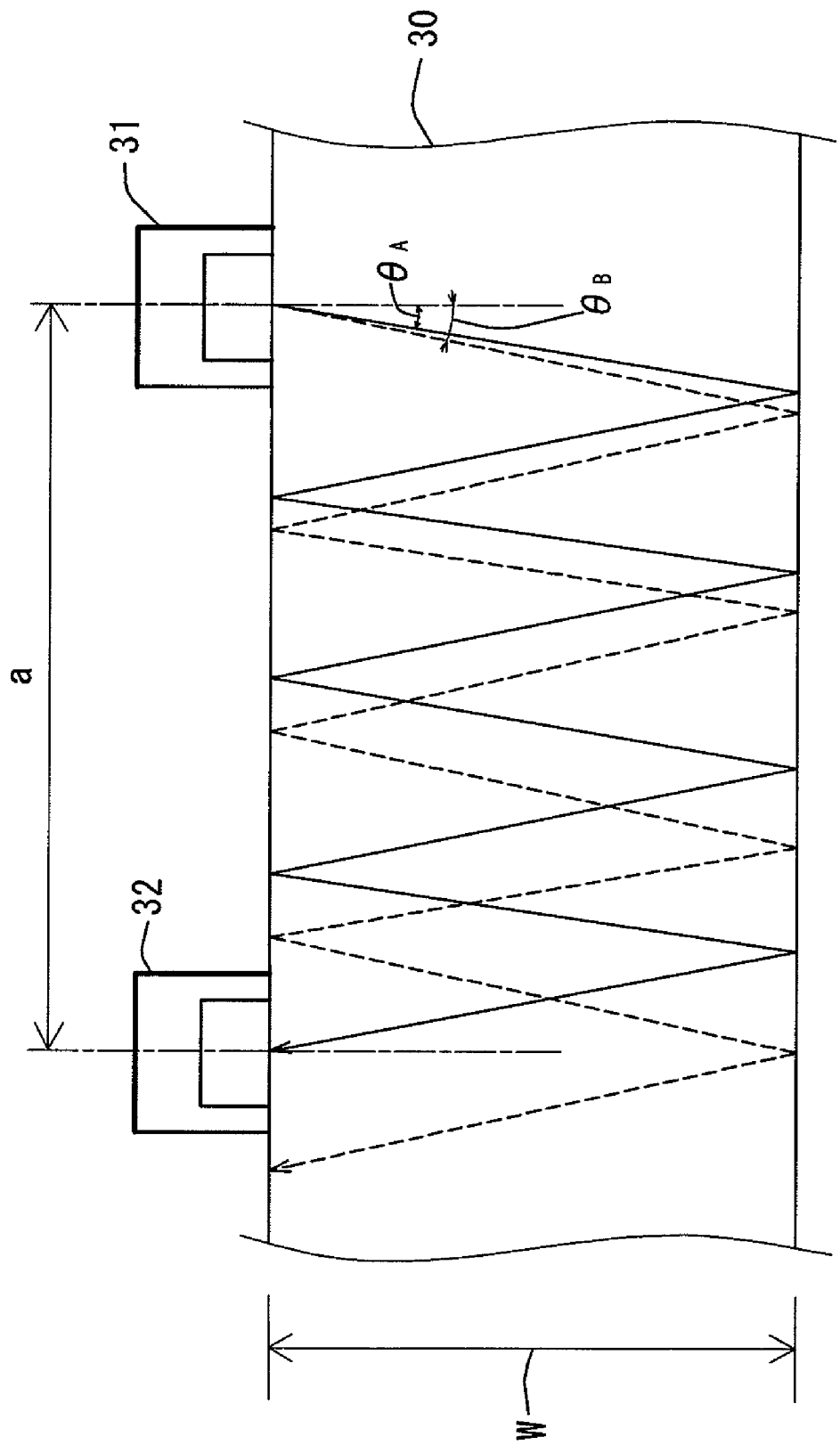
[FIG. 42] A schematic view of longitudinal wave propagation.
Figure 43:
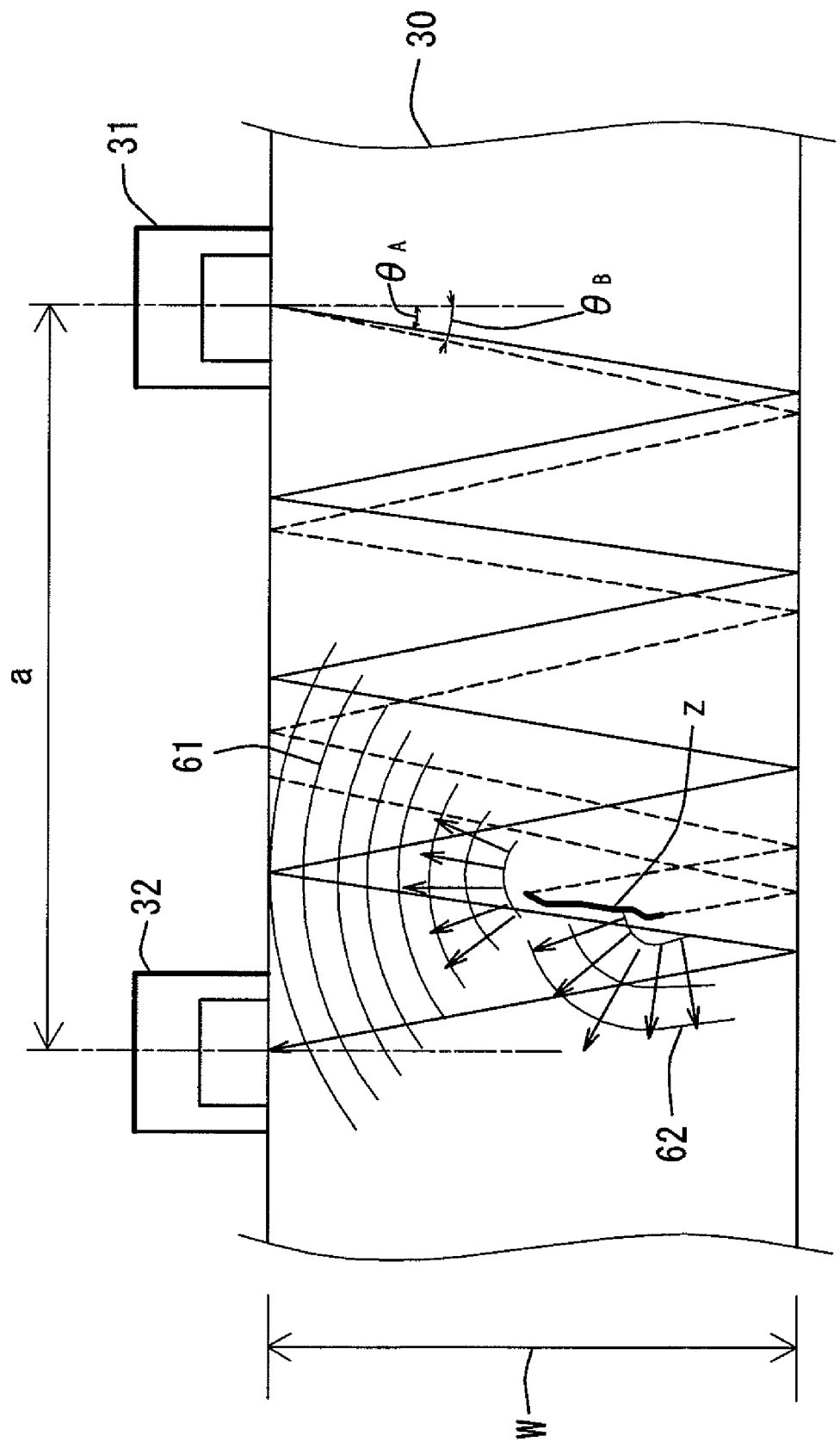
[FIG. 43] A schematic view of the generation states of a longitudinal scattering wave and a transverse scattering wave due to a flaw.
Figure 44:
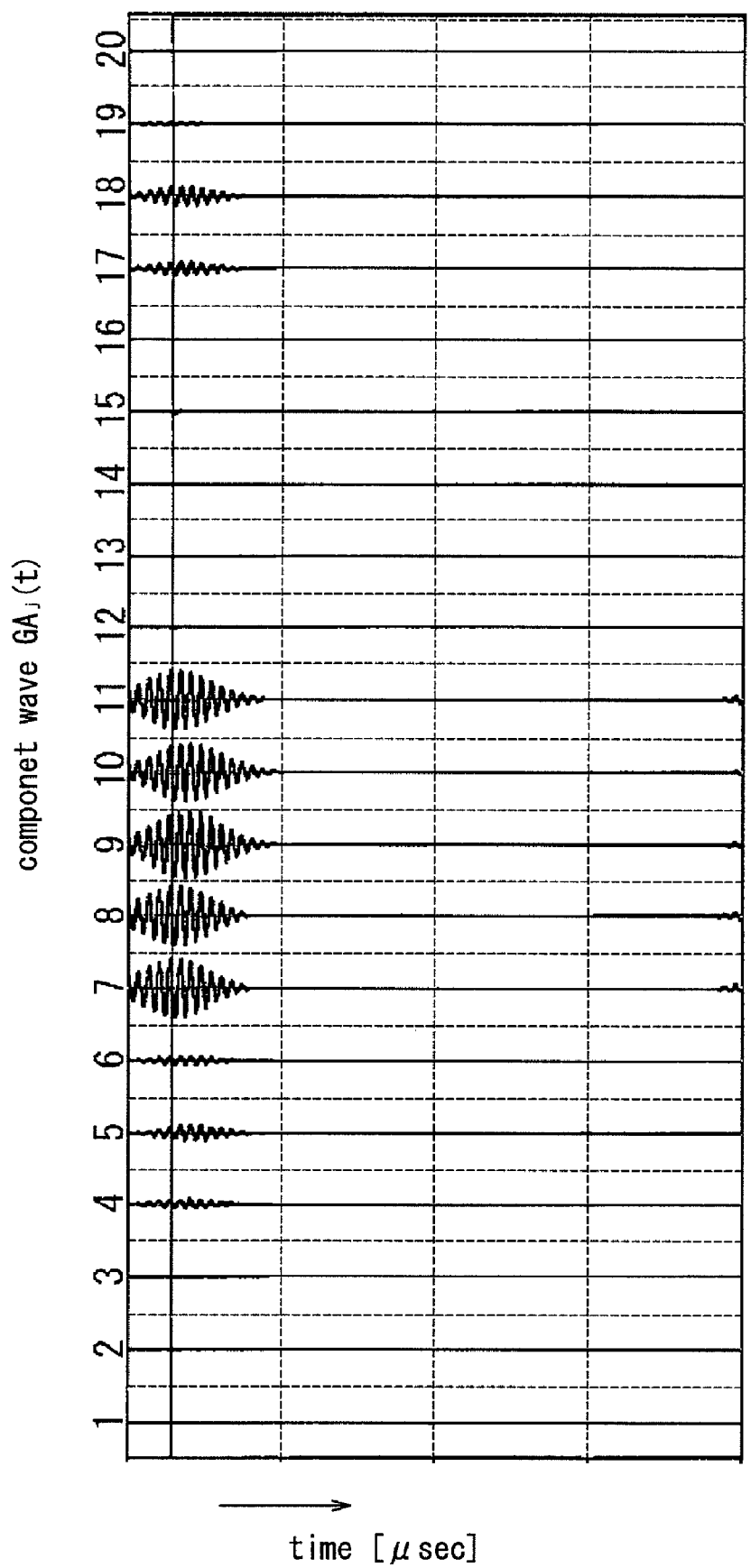
[FIG. 44] A comparative display of a component wave.
Figure 45:
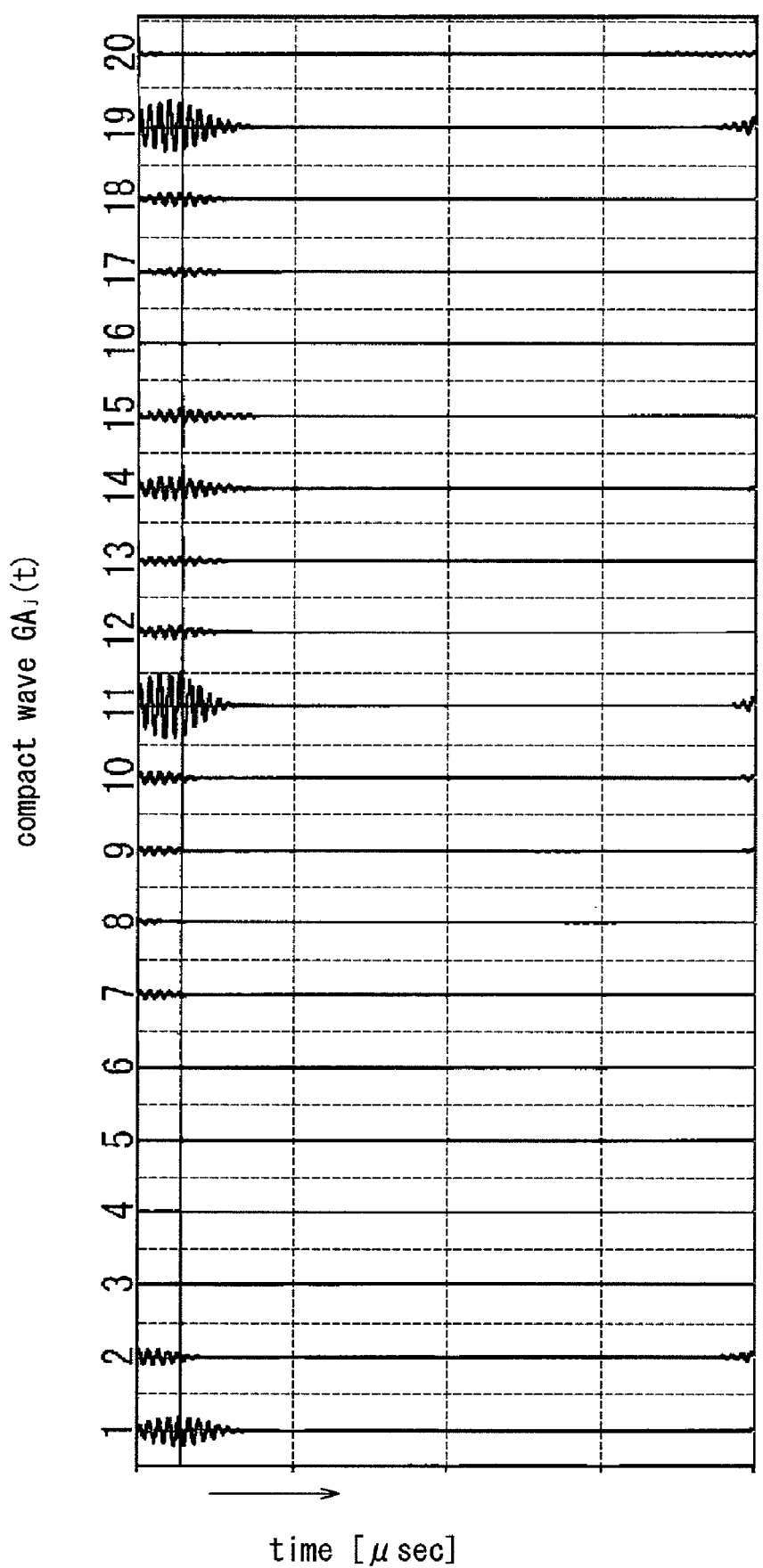
[FIG. 45] A comparative display of a component wave by an inappropriate $f_0$ value.

30 Probing target
31 Transmission probe
32 Receiving probe
40 CPU (inverse transformation section)
41 Display device (comparative display section, determination section)
47 Vibrator
Z Flaw

The invention claimed is:

1. An ultrasonic probing method utilizing a resonance phenomenon, by which:
   a step function voltage is applied to a vibrator in a transmission probe; and
   a wide band ultrasonic wave is continuously transmitted from the transmission probe and a wide band ultrasonic wave from the probing target is received by a receiving probe;
   wherein a measurement is performed in the state where the transmission probe and the receiving probe are located away from each other on a surface of the probing target, the method having:
   a receiving function of obtaining a received wave $G_j(t)$ each time the position of each of the probes is changed;
   an arithmetic operation function of obtaining a spectrum $F_j(f)$ corresponding to the received wave $G_j(t)$ by Fourier transformation;
   a display function of providing a comparative display of the received wave $G_j(t)$ and the spectrum $F_j(f)$ at measurement points j;
   a function of generating longitudinal cursors $f_1$, $2f_1$, $3f_1$, ..., $n_A f_1$ on a screen of the comparative display of the spectrum $F_j(f)$, and changing the positions of the longitudinal cursors to match each of all the cursors to a rising spectrum peak having a large value;
   a function of performing an arithmetic operation/display of a thickness W of the probing target from the values of the longitudinal cursors and a sonic velocity $V_P$ of the probing target; and
   a function of obtaining a longitudinal cursor $f_{S1}$ by an arithmetic operation of $f_{S1}=\gamma_1 \cdot f_1$ using a sonic ratio $\gamma_1$ between a transverse wave and a longitudinal wave of the probing target, generating longitudinal cursors $f_{S1}$, $f_{S2}$, $f_{S3}$, ..., $n_A f_{S1}$ on the screen of the comparative display of the spectrum $F_j(f)$, and changing the positions of the longitudinal cursors by a small amount to match the cursors, which are obtained by multiplying the longitudinal cursor $f_{S1}$ by an integer, to a rising spectrum peak having a relatively small value;

the method comprising:
a first step of extracting a narrow band spectrum $FA_j(f)$ of a frequency of $n_B \cdot f_{S1}$ from the spectrum $F_j(f)$ using an integer $n_B$ of 1 or greater, and obtaining a component wave $GA_j(t)$ corresponding to the narrow band spectrum $FA_j(f)$ by inverse Fourier transformation;
a second step of providing a comparative display of the component wave $GA_j(t)$ using predetermined sizing coefficients $n_{S1}$, $n_{S2}$ and $n_{S3}$; and
a third step of determining the position of a flaw inside the probing target right below a line segment connecting the center of the transmission probe and the center of the receiving probe, based on at which of the measurement points a wave can be confirmed to be generated on the screen of the comparative display of the component wave $GA_j(t)$.

2. An ultrasonic probing method utilizing a resonance phenomenon, by which:
a step function voltage is applied to a vibrator in a transmission probe; and
a wide band ultrasonic wave is continuously transmitted from the transmission probe and a wide band ultrasonic wave from the probing target is received by a receiving probe;
wherein a measurement is performed in the state where the transmission probe and the receiving probe are located away from each other on a surface of the probing target, the method having:
a receiving function of obtaining a received wave $G_j(t)$ each time the position of each of the probes is changed;
an arithmetic operation function of obtaining a spectrum $F_j(f)$ corresponding to the received wave $G_j(t)$ by Fourier transformation;
a display function of providing a comparative display of the received wave $G_j(t)$ and the spectrum $F_j(f)$ at measurement points j;
a function of generating longitudinal cursors $f_1$, $2f_1$, $3f_1$, ..., $n_A f_1$ on a screen of the comparative display of the spectrum $F_j(f)$, and changing the positions of the longitudinal cursors to match each of all the cursors to a rising spectrum peak having a large value; and
a function of performing an arithmetic operation/display of a thickness W of the probing target from the values of the longitudinal cursors and a sonic velocity $V_P$ of the probing target;
the method comprising:
a first step of extracting a narrow band spectrum $FA_j(f)$ of a frequency of $n_B \cdot f_1$ from the spectrum $F_j(f)$ using an integer $n_B$ of 1 or greater, and obtaining a component wave $GA_j(t)$ corresponding to the narrow band spectrum $FA_j(f)$ by inverse Fourier transformation;
a second step of providing a comparative display of the component wave $GA_j(t)$ using predetermined sizing coefficients $n_{S1}$, $n_{S2}$ and $n_{S3}$; and
a third step of determining the position of a flaw inside the probing target right below a line segment connecting the center of the transmission probe and the center of the receiving probe, based on at which of the measurement points a wave is generated on the screen of the comparative display of the component wave $GA_j(t)$.

3. An ultrasonic probing method utilizing a resonance phenomenon according to claim 2, wherein the positions of the transmission probe and the receiving probe are changed by translating the positions in units of a predetermined amount in a direction perpendicular to the line segment connecting the centers of the probes, or by fixing the position of either one probe and moving the other probe by a predetermined amount in a circumferential direction with the fixed position as the center.

4. An ultrasonic probing method utilizing a resonance phenomenon according to claim 2, wherein:
a function $\sin\{(\pi/2)(f/f_{HL})\}$ defined by the spectrum $F_j(f)$ and a predetermined $f_{HL}$ is used to calculate $$\tilde{F}_j(f) = \sin\frac{\pi}{2}\left(\frac{f}{f_{HL}}\right) \times F_j(f);$$

$$\tilde{G}_j(t) = \int_{-\infty}^{\infty} (F_j(f) \cdot e^{i\omega t})\,df$$

is calculated by Fourier transformation;
$F_j(f)$ is replaced with $\tilde{F}_j(f)$; and
$G_j(f)$ is replaced with $\tilde{G}_j(f)$
(where $F_j$ and $G_j$ represent a state where "~" is provided above $F_j$ and $G_j$ in the expression; i is an imaginary number; the same is applied to the following).

5. An ultrasonic probing method utilizing a resonance phenomenon according to claim 2, wherein the narrow band spectrum $FA_j(f)$ is extracted by:
obtaining a combination function $S(f)$ of an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater;
setting the frequency $f_0$ to a value of $n_B \times f_1$ or a value of $n_B \times f_{S1}$; and
obtaining $FA_j(f)$ by an arithmetic operation of:

$$FA_j(f) = S(f)^{n_{S4}} \times F_j(f),$$

using the function $S(f)$ and a sizing coefficient $n_{S4}$.

6. An ultrasonic probing method utilizing a resonance phenomenon according to claim 2, wherein the narrow band spectrum $FA_j(f)$ is extracted by performing an arithmetic operation of:

$$FA_j(f) = S(f) \cdot F_j(f),$$

or band pass processing,
in the state where:
a predetermined value $\Delta f_a$ which is preset or an externally input is used;
the longitudinal cursor $f_1$ or $f_{S1}$ is represented as $\tilde{f}_1$ (where $\tilde{f}_1$ represents a state where "~" is provided above $f_j$ in the expression; the same is applied to the following); and
a function $S(f)$ which is:
0.0 at a frequency of $0 \leq f < \tilde{f}_1 - \Delta f_a$,
1.0 at a frequency of $\tilde{f}_1 - \Delta f_a \leq f \leq \tilde{f}_1 + \Delta f_a$, and
0.0 at a frequency of $f > \tilde{f}_1 + \Delta f_a$,
and the spectrum $F_j(f)$ are used.

7. An ultrasonic probing method utilizing a resonance phenomenon according to claim 2, wherein the component wave $GA_j(t)$ is provided for the comparative display using the predetermined sizing coefficients $n_{S1}$, $n_{S2}$ and $n_{S3}$ by:
setting the maximum amplitude of each of the measurement points j of the component wave $GA_j(t)$ to $A_j$;
setting the maximum value in $A_j$ to $A_{max}$;
replacing $A_j$ which is $A_j = (1/n_{S1})A_{max}$ with $A_{max}$ using the sizing coefficient $n_{S1}$;
obtaining $\tilde{GA}_j(t)$ by an arithmetic operation of $\tilde{G}A_j(t) = (A_j/A_{max})GA_j(t)$;
replacing $GA_j(t)$ with $\tilde{GA}_j(t)$;
then creating a wave of $n_{S3} \times GA_j^{n_{S2}}(t)$ using the other sizing coefficients $n_{S2}$ and $n_{S3}$; and providing a comparative display of $n_{S3} \times GA_j^{nS2}(t)$ as the comparative display of the component wave $GA_j(t)$ (where G represents a state where "~" is provided above G in the expression; the same is applied to the following).

8. An ultrasonic probing method utilizing a resonance phenomenon according to claim 2, wherein the narrow band spectrum $FA_j(f)$ is extracted by:

obtaining the narrow band spectrum $FA_j(f)$ by the arithmetic operation of:

$$FA_j(f) = S(f)^{nS4} \times F_j(f)$$

each time the calculation of:

$$f_0 = f_0 + \Delta f_H$$

is performed;

repeating the first through third steps each time $FA_j(f)$ is obtained; and stopping the arithmetic operation of $f_0 = f_0 + \Delta f_H$, the arithmetic operation of $FA_j(f) = S(f)^{nS4} \times F_j(f)$, and the first through third steps by an external instruction or automatically, in the state where:

a combination function $S(f)$ is obtained by an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater;

the function $S(f)$, a sizing coefficient $n_{S4}$, and a predetermined value $\Delta f_0$ are used; and where the longitudinal cursor $f_1$ or $f_{S1}$ is represented as $f_1$, the initial value of the frequency $f_0$ is $f_0 = n_B \cdot f_1 - \Delta f_0$, the final value of the frequency $f_0$ is $f_0 = n_B \cdot f_1 + \Delta f_0$; the change amount of the frequency is $\Delta f_H$.

9. An ultrasonic probing method utilizing a resonance phenomenon according to claim 2, wherein the narrow band spectrum $FA_j(f)$ is extracted by:

obtaining the narrow band spectrum $FA_j(f)$ by the arithmetic operation of:

$$FA_j(f) = S(f) \times F_j(f),$$

or band pass processing each time the calculation of:

$$f_0 = f_0 + \Delta f_H$$

is performed;

repeating the first through third steps each time $FA_j(f)$ is obtained; and stopping the arithmetic operation of $f_0 = f_0 + \Delta f_H$, the arithmetic operation of $FA_j(f) = S(f) \cdot F_j(f)$, and the first through third steps by an external instruction or automatically, in the state where:

the predetermined value $\Delta f_a$ is used;

a function $S(f)$ which is 0.0 at a frequency of $0 \leq f < f_0 - \Delta f_a$, 1.0 at a frequency of $f_0 - \Delta f_a \leq f \leq f_0 + \Delta f_a$, and 0.0 at a frequency of $f > f_0 + \Delta f_a$, is used, and the predetermined value $\Delta f_0$ is used; and where the longitudinal cursor $f_1$ or $f_{S1}$ is represented as $f_1$, the initial value of the frequency $f_0$ is $f_0 = n_B \cdot f_1 - \Delta f_0$, the final value of the frequency $f_0$ is $f_0 = n_B \cdot f_1 + \Delta f_0$, and the change amount of the frequency is $\Delta f_H$.

10. An ultrasonic probing method utilizing a resonance phenomenon according to claim 2, wherein:

either one of a combination function FiLT(t) obtained by combining a sin function which is 0.0 at time 0, 1.0 at time $t_g$, and 0.0 at time $2t_g$, and a function which is 0.0 at time $2 t_g$ or greater;

a combination function FiLT(t) obtained by combining a function which is 0.0 at time 0 to $t_g - \Delta t$, a sin function which is 0.0 at time $t_g - \Delta t$, 1.0 at time $t_g$, and 0.0 at time $t_g + \Delta t$, and a function which is 0.0 at time $t_g + \Delta t$ or greater using the predetermined value $\Delta t$; and a combination function FiLT(t) obtained by combining an increase function which is 0.0 at time 0 and 1.0 at time $t_g$ and a function which is 1.0 at time $t_g$ or greater is selected;

a predetermined value $\Delta t_g$ and a predetermined coefficient $n5$ are used;

the initial value of time $t_g$ is set to 0.0;

each time the arithmetic operation of:

$$t_g = t_g + \Delta t_g$$

is performed, a component wave $GB_j(t)$ is obtained by the arithmetic operation of:

$$GB_j(t) = FiLT^{n5}(t) \cdot GA_j(t);$$

each time $GB_j(t)$ is obtained, $GA_j(t)$ in the second and third steps is replaced with $GB_j(t)$; and the arithmetic operation of $t_g = t_g + \Delta t_g$, the arithmetic operation of $GB_j(t) = FiLT^{n5}(t) \cdot GA_j(t)$, and the second and third steps are stopped by an external instruction or automatically.

11. An ultrasonic probing apparatus utilizing a resonance phenomenon, in which:

a step function voltage is applied to a vibrator in a transmission probe; and a wide band ultrasonic wave is continuously transmitted from the transmission probe and a wide band ultrasonic wave from the probing target is received by a receiving probe;

wherein a measurement is performed in the state where the transmission probe and the receiving probe are located away from each other on a surface of the probing target, the apparatus having:

a receiving function of obtaining a received wave $G_j(t)$ each time the position of each of the probes is changed;

an arithmetic operation function of obtaining a spectrum $F_j(f)$ corresponding to the received wave $G_j(t)$ by Fourier transformation;

a display function of providing a comparative display of the received wave $G_j(t)$ and the spectrum $F_j(f)$ at measurement points j;

a function of generating longitudinal cursors $f_1$, $2f_1$, $3f_1$, . . . , $n_A f_1$ on a screen of the comparative display of the spectrum $F_j(f)$, and changing the positions of the longitudinal cursors to match each of all the cursors to a rising spectrum peak having a large value;

a function of performing an arithmetic operation/display of a thickness W of the probing target from the values of the longitudinal cursors and a sonic velocity $V_P$ of the probing target; and a function of obtaining a longitudinal cursor $f_{S1}$ by an arithmetic operation of $f_{S1} = \gamma_1 \cdot f_1$ using a sonic ratio $\gamma_1$ between a transverse wave and a longitudinal wave of the probing target, generating longitudinal cursors $f_{S1}$, $f_{S2}$, $f_{S3}$, . . . , $n_A f_{S1}$ on the screen of the comparative display of the spectrum $F_j(f)$, and changing the positions of the longitudinal cursors by a small amount to match the cursors, which are obtained by multiplying the longitudinal cursor $f_{S1}$ by an integer, to a rising spectrum peak having a relatively small value;

the apparatus comprising:

an inverse transformation section for extracting a narrow band spectrum $FA_j(f)$ of a frequency of $n_B \cdot f_{S1}$ from the spectrum $F_j(f)$ using an integer $n_B$ of 1 or greater, and obtaining a component wave $GA_j(t)$ corresponding to the narrow band spectrum $FA_j(f)$ by inverse Fourier transformation;

a comparative display section for providing a comparative display of the component wave $GA_j(t)$ using predetermined sizing coefficients $n_{S1}$, $n_{S2}$ and $n_{S3}$; and a determination section for determining the position of a flaw inside the probing target right below a line segment connecting the center of the transmission probe and the center of the receiving probe, based on at which of the measurement points a wave can be confirmed to be generated on the screen of the comparative display of the component wave $GA_j(t)$.

12. An ultrasonic probing apparatus utilizing a resonance phenomenon, in which:

a step function voltage is applied to a vibrator in a transmission probe; and a wide band ultrasonic wave is continuously transmitted from the transmission probe and a wide band ultrasonic wave from the probing target is received by a receiving probe;

wherein a measurement is performed in the state where the transmission probe and the receiving probe are located away from each other on a surface of the probing target, the apparatus having:

a receiving function of obtaining a received wave $G_j(t)$ each time the position of each of the probes is changed;

an arithmetic operation function of obtaining a spectrum $F_j(f)$ corresponding to the received wave $G_j(t)$ by Fourier transformation;

a display function of providing a comparative display of the received wave $G_j(t)$ and the spectrum $F_j(f)$ at measurement points j;

a function of generating longitudinal cursors $f_1$, $2f_1$, $3f_1$, ..., $n_A f_1$ on a screen of the comparative display of the spectrum $F_j(f)$, and changing the positions of the longitudinal cursors to match each of all the cursors to a rising spectrum peak having a large value; and a function of performing an arithmetic operation/display of a thickness W of the probing target from the values of the longitudinal cursors and a sonic velocity $V_P$ of the probing target;

the apparatus comprising:

an inverse transformation section for extracting a narrow band spectrum $FA_j(f)$ of a frequency of $n_B \cdot f_1$ from the spectrum $F_j(f)$ using an integer $n_B$ of 1 or greater, and obtaining a component wave $GA_j(t)$ corresponding to the narrow band spectrum $FA_j(f)$ by inverse Fourier transformation;

a comparative display section for providing a comparative display of the component wave $GA_j(t)$ using predetermined sizing coefficients $n_{S1}$, $n_{S2}$ and $n_{S3}$; and a determination section for determining the position of a flaw inside the probing target right below a line segment connecting the center of the transmission probe and the center of the receiving probe, based on at which of the measurement points a wave is generated on the screen of the comparative display of the component wave $GA_j(t)$.

13. An ultrasonic probing apparatus utilizing a resonance phenomenon according to claim 12, wherein the positions of the transmission probe and the receiving probe are changed by translating the positions in units of a predetermined amount in a direction perpendicular to the line segment connecting the centers of the probes, or by fixing the position of either one probe and moving the other probe by a predetermined amount in a circumferential direction with the fixed position as the center.

14. An ultrasonic probing apparatus utilizing a resonance phenomenon according to claim 12, wherein:

a function $\sin\{(\pi/2)(f/f_{HL})\}$ defined by the spectrum $F_j(f)$ and a predetermined $f_{HL}$ is used to calculate $$\tilde{F}_j(f) = \sin\frac{\pi}{2}\left(\frac{f}{f_{HL}}\right) \times F_j(f);$$

$$\tilde{G}_j(t) = \int_{-\infty}^{\infty} (F_j(f) \cdot e^{i\omega t}) df$$

is calculated by Fourier transformation;

$F_j(f)$ is replaced with $\tilde{F}_j(f)$; and $G_j(f)$ is replaced with $\tilde{G}_j(f)$ (where $\tilde{F}_j$ and $\tilde{G}_j$ represent a state where "~" is provided above $F_j$ and $G_j$ in the expression; i is an imaginary number; the same is applied to the following).

15. An ultrasonic probing apparatus utilizing a resonance phenomenon according to claim 12, wherein the narrow band spectrum $FA_j(f)$ is extracted by:

obtaining a combination function $S(f)$ of an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater;

setting the frequency $f_0$ to a value of $n_B \times f_1$ or a value of $n_B \times f_{S1}$; and obtaining $FA_j(f)$ by an arithmetic operation of:

$FA_j(f) = S(f)^{nS4} \times F_j(f)$, using the function $S(f)$ and a sizing coefficient $n_{S4}$.

16. An ultrasonic probing apparatus utilizing a resonance phenomenon according to claim 12, wherein the narrow band spectrum $FA_j(f)$ is extracted by performing an arithmetic operation of:

$FA_j(f) = S(f) \cdot F_j(f)$, or band pass processing, in the state where:

a predetermined value $\Delta f_a$ which is preset or an externally input is used;

the longitudinal cursor $f_1$ or $f_{S1}$ is represented as $\tilde{f}_1$ (where $\tilde{f}_1$ represents a state where "~" is provided above $f_1$ in the expression; the same is applied to the following); and a function $S(f)$ which is:

0.0 at a frequency of $0 \leq f < \tilde{f}_1 - \Delta f_a$, 1.0 at a frequency of $\tilde{f}_1 - \Delta f_a \leq f \leq \tilde{f}_1 + \Delta f_a$, and 0.0 at a frequency of $f > \tilde{f}_1 + \Delta f_a$, and the spectrum $F_j(f)$ are used.

17. An ultrasonic probing apparatus utilizing a resonance phenomenon according to claim 12, wherein the component wave $GA_j(t)$ is provided for the comparative display using the predetermined sizing coefficients $n_{S1}$, $n_{S2}$ and $n_{S3}$ by:

setting the maximum amplitude of each of the measurement points j of the component wave $GA_j(t)$ to $A_j$;

setting the maximum value in $A_j$ to $A_{max}$;

replacing $A_j$ which is $A_j = (1/n_{S1})A_{max}$ with $A_{max}$ using the sizing coefficient $n_{S1}$;

obtaining $\tilde{G}A_j(t)$ by an arithmetic operation of $\tilde{G}A_j(t) = (A_j/A_{max})GA_j(t)$;

replacing $\tilde{G}A_j(t)$ with $GA_j(t)$;

then creating a wave of $n_{S3} \times GA_j^{nS2}(t)$ using the other sizing coefficients $n_{S2}$ and $n_{S3}$; and providing a comparative display of $n_{S3} \times GA_j^{nS2}(t)$ as the comparative display of the component wave $\tilde{GA}_j(t)$ (where $\tilde{G}$ represents a state where "~" is provided above G in the expression; the same is applied to the following).

18. An ultrasonic probing apparatus utilizing a resonance phenomenon according to claim 12, wherein the narrow band spectrum $FA_j(f)$ is extracted by:
  obtaining the narrow band spectrum $FA_j(f)$ by the arithmetic operation of:

$$FA_j(f) = S(f)^{nS4} \times F_j(f)$$

each time the calculation of:

$$f_0 = f_0 + \Delta f_H$$

is performed;
  repeating the processing by the inverse transformation section, the comparative display section and the determination section each time $FA_j(f)$ is obtained; and
  stopping the arithmetic operation of $f_0 = f_0 + \Delta f_H$, the arithmetic operation of $FA_j(f) = S(f)^{nS4} \times F_j(f)$, and the processing by the inverse transformation section, the comparative display section and the determination section by an external instruction or automatically,
  in the state where:
  a combination function $S(f)$ is obtained by an increase function which is 0.0 at a frequency of 0 and 1.0 at a frequency of $f_0$, a decrease function which is 1.0 at a frequency of $f_0$ and 0.0 at a frequency of $2f_0$, and a function which is 0.0 at a frequency of $2f_0$ or greater;
  the function $S(f)$, a sizing coefficient $n_{S4}$, and a predetermined value $\Delta f_0$ are used; and
  where the longitudinal cursor $f_1$ or $f_{S1}$ is represented as $f_1$,
  the initial value of the frequency $f_0$ is $f_0 = n_B \cdot f_1 - \Delta f_0$,
  the final value of the frequency $f_0$ is $f_0 = n_B \cdot f_1 + \Delta f_0$;
  the change amount of the frequency is $\Delta f_H$.

19. An ultrasonic probing apparatus utilizing a resonance phenomenon according to claim 12, wherein the narrow band spectrum $FA_j(f)$ is extracted by:
  obtaining the narrow band spectrum $FA_j(f)$ by the arithmetic operation of:

$$FA_j(f) = S(f) \times F_j(f),$$

or band pass processing each time the calculation of:

$$f_0 = f_0 + \Delta f_H$$

is performed;
  repeating the processing by the inverse transformation section, the comparative display section and the determination section each time $FA_j(f)$ is obtained; and
  stopping the arithmetic operation of $f_0 = f_0 + \Delta f_H$, the arithmetic operation of $FA_j(f) = S(f)^{nS4} \times F_j(f)$, and the processing by the inverse transformation section, the comparative display section and the determination section by an external instruction or automatically,
  in the state where:
  the predetermined value $\Delta f_a$ is used;
  a function $S(f)$ which is
  0.0 at a frequency of $0 \leq f \leq f_0 - \Delta f_a$,
  1.0 at a frequency of $f_0 - \Delta f_a \leq f \leq f_0 + \Delta f_a$, and
  0.0 at a frequency of $f > f_0 + \Delta f_a$,
  is used, and the predetermined value $\Delta f_0$ is used; and
  where the longitudinal cursor $f_1$ or $f_{S1}$ is represented as $f_1$,
  the initial value of the frequency $f_0$ is $f_0 = n_B \cdot f_1 - \Delta f_0$,
  the final value of the frequency $f_0$ is $f_0 = n_B \cdot f_1 + \Delta f_0$, and
  the change amount of the frequency is $\Delta f_H$.

20. An ultrasonic probing apparatus utilizing a resonance phenomenon according to claim 12, wherein:
  either one of a combination function $FiLT(t)$ obtained by combining a sin function which is 0.0 at time 0, 1.0 at time $t_g$, and 0.0 at time $2t_g$, and a function which is 0.0 at time $2 t_g$ or greater;
  a combination function $FiLT(f)$ obtained by combining a function which is 0.0 at time 0 to $t_g - \Delta t$, a sin function which is 0 at time $t_g - \Delta t$, 1.0 at time $t_g$, and 0.0 at time $t_g + \Delta t$, and a function which is 0.0 at time $t_g + \Delta t$ or greater using the predetermined value $\Delta t$; and
  a combination function $FiLT(t)$ obtained by combining an increase function which is 0.0 at time 0 and 1.0 at time $t_g$ and a function which is 1.0 at time $t_g$ or greater is selected;
  the predetermined value $\Delta t_g$ and the predetermined coefficient n5 are used;
  the initial value of time $t_g$ is set to 0.0;
  each time the arithmetic operation of:

$$t_g = t_g + \Delta t_g$$

is performed, the component wave $GB_j(t)$ is obtained by the arithmetic operation of:

$$GB_j(t) = FiLT^{n5}(t) \cdot GA_j(t);$$

each time $GB_j(t)$ is obtained, $GA_j(t)$ in the processing by the comparative display section and the determination section is replaced with $GB_j(t)$; and
  the arithmetic operation of $t_g = t_g + \Delta t_g$, the arithmetic operation of $GB_j(t) = FiLT^{n5}(t) \cdot GA_j(t)$, and the processing by the comparative display section and the determination section are stopped by an external instruction or automatically.

* * * * *